US012007376B2

(12) United States Patent
Lebedev et al.

(10) Patent No.: US 12,007,376 B2
(45) Date of Patent: Jun. 11, 2024

(54) METHOD FOR DETERMINING A CONCENTRATION OF A SYNTHESIS COMPONENT IN A RADIOPHARMACEUTICAL SAMPLE

(71) Applicant: Trace-Ability, Inc., Van Nuys, CA (US)

(72) Inventors: Artem Y. Lebedev, Santa Monica, CA (US); Arkadij M. Elizarov, Woodland Hills, CA (US)

(73) Assignee: Trace-Ability, Inc., Van Nuys, CA (US)

( * ) Notice: Subject to any disclaimer, the term of this patent is extended or adjusted under 35 U.S.C. 154(b) by 559 days.

(21) Appl. No.: 17/122,496

(22) Filed: Dec. 15, 2020

(65) Prior Publication Data
US 2021/0102929 A1    Apr. 8, 2021

Related U.S. Application Data

(60) Division of application No. 14/866,684, filed on Sep. 25, 2015, now Pat. No. 10,895,563, which is a continuation-in-part of application No. 14/191,293, filed on Feb. 26, 2014, now Pat. No. 10,309,947.

(60) Provisional application No. 62/171,183, filed on Jun. 4, 2015, provisional application No. 62/056,529, filed on Sep. 27, 2014.

(51) Int. Cl.
| | | |
|---|---|---|
| G01N 33/15 | (2006.01) | |
| C12M 1/34 | (2006.01) | |
| C12Q 1/02 | (2006.01) | |
| G01N 21/78 | (2006.01) | |
| G01N 21/82 | (2006.01) | |
| A61B 6/03 | (2006.01) | |
| G01N 21/25 | (2006.01) | |
| G01N 21/51 | (2006.01) | |
| G01N 21/75 | (2006.01) | |
| G01N 33/00 | (2006.01) | |

(52) U.S. Cl.
CPC ............. *G01N 33/15* (2013.01); *C12M 41/36* (2013.01); *C12Q 1/02* (2013.01); *G01N 21/78* (2013.01); *G01N 21/82* (2013.01); *A61B 6/037* (2013.01); *G01N 21/253* (2013.01); *G01N 21/51* (2013.01); *G01N 2021/752* (2013.01); *G01N 2033/0093* (2013.01)

(58) Field of Classification Search
CPC ....................... G01N 2033/0093; G01N 33/15
USPC .................................................. 436/542, 504
See application file for complete search history.

(56) References Cited

U.S. PATENT DOCUMENTS

| | | | |
|---|---|---|---|
| 4,871,674 A | 10/1989 | Matsui et al. | |
| 5,310,657 A | 5/1994 | Berzofsky | |
| 5,479,969 A | 1/1996 | Hardie et al. | |
| 7,329,538 B2 | 2/2008 | Wainwright et al. | |
| 8,021,611 B2 | 9/2011 | Roach et al. | |
| 8,980,184 B2 | 3/2015 | Mueller et al. | |
| 2002/0142301 A1 | 10/2002 | Hovig et al. | |
| 2004/0022696 A1 | 2/2004 | Zigler et al. | |
| 2004/0086437 A1 | 5/2004 | Jackson | |
| 2004/0126279 A1 | 7/2004 | Renzi et al. | |
| 2005/0052646 A1* | 3/2005 | Wohlstadter .............. B01L 9/50 356/311 |
| 2006/0245980 A1 | 11/2006 | Kiselev et al. | |
| 2009/0087924 A1 | 4/2009 | Bynum et al. | |
| 2010/0019157 A1 | 1/2010 | Furlan et al. | |
| 2010/0145630 A1 | 6/2010 | Ball et al. | |
| 2011/0070158 A1 | 3/2011 | Nutt et al. | |
| 2011/0070458 A1 | 3/2011 | Quan et al. | |
| 2012/0077429 A1 | 3/2012 | Wernimont et al. | |
| 2016/0228876 A1 | 8/2016 | Chu et al. | |
| 2018/0065103 A1 | 3/2018 | Schopf et al. | |
| 2020/0080979 A1 | 3/2020 | Blevins et al. | |

FOREIGN PATENT DOCUMENTS

| | | |
|---|---|---|
| CN | 1036078 A | 10/1989 |
| CN | 1249816 A | 4/2000 |
| CN | 1846136 A | 10/2006 |
| CN | 2898829 Y | 5/2007 |
| CN | 101000344 A | 7/2007 |
| CN | 101013137 A | 8/2007 |
| CN | 201935917 U | 8/2011 |
| CN | 102576007 A | 7/2012 |
| CN | 202433374 U | 9/2012 |
| CN | 103344464 A | 10/2013 |

(Continued)

OTHER PUBLICATIONS

PCT Search Report & Written Opinion dated Jan. 26, 2016 for PCT/US2015/052448 entitled Palette-Based Systems for Analyte Characterization filed on Sep. 25, 2015 (Applicant—Trace-ability, Inc.); 18 pages.

1st Office Action in related CNSN 2015800599311 dated Apr. 27, 2018.

European Search Report and Opinion in corresponding EPSN 15845167.4 dated Mar. 26, 2018.

J.H. Mecchia Ortiz, A.M. Peyrot, F. Fagalde, N.E. Katz; "Trans-kinetic effects in ligand substitution processes of rutheniumpolypyridyl complexes", journal homepage: www.elsevier.com/locate/inoche, Inorganic Chemistry Communications 98, (2018), 44-47.

(Continued)

*Primary Examiner* — Natalia Levkovich
(74) *Attorney, Agent, or Firm* — Harness, Dickey & Pierce, P.L.C.

(57) ABSTRACT

A method for determining a concentration of a synthesis component in a radiopharmaceutical sample comprises providing an indicator, a metal or a metal complex, contacting the radiopharmaceutical sample with the indicator, metal or metal complex for a period of time sufficient to obtain an interaction, measuring an optical characteristic of the interacted components, and determining a concentration of the synthesis component in the radiopharmaceutical sample based on the measured optical characteristic.

19 Claims, 20 Drawing Sheets

(56) References Cited

FOREIGN PATENT DOCUMENTS

| EP | 1940543 A2 | 7/2008 |
| WO | WO-2000062931 A1 | 10/2000 |
| WO | WO-2009153163 A1 | 12/2009 |

OTHER PUBLICATIONS

D.W. Blevins, G.H. Rigney, M.Y. Fang, M.R. Akula, D.R. Osborne; "Novel methods for the quantification of toxic, residual phase transfer catalyst in fluorine-18 labeled radiotracers", journal homepage: www.elsevier.com/locate/nucmedbio, Nuclear Medicine and Biology, 74-75, (2019), 41-48.

* cited by examiner

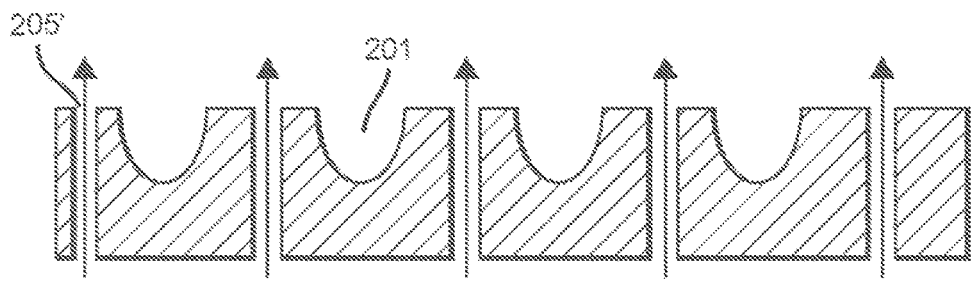
FIG. 2D
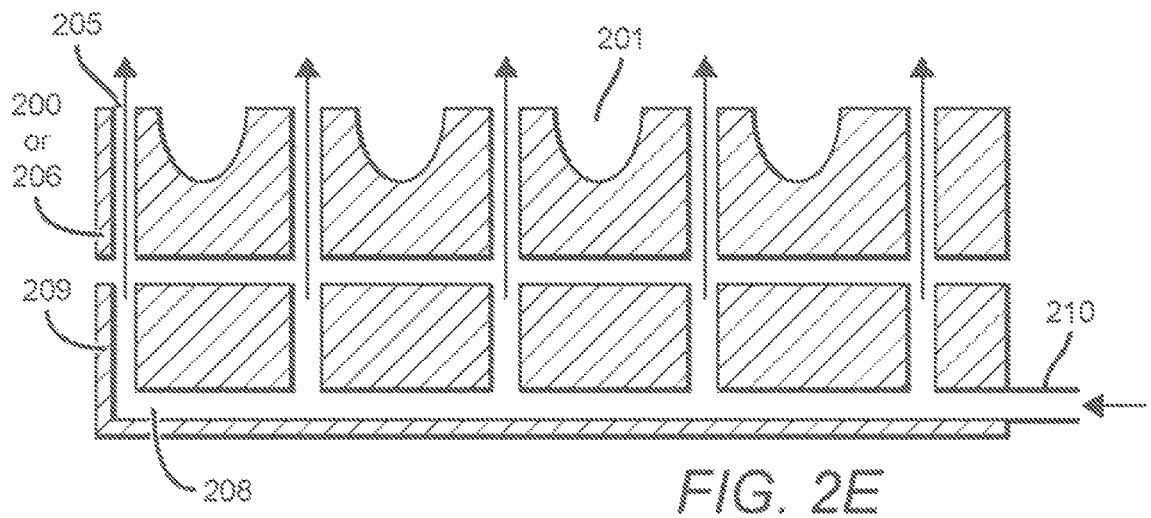
FIG. 2E
FIG. 2F
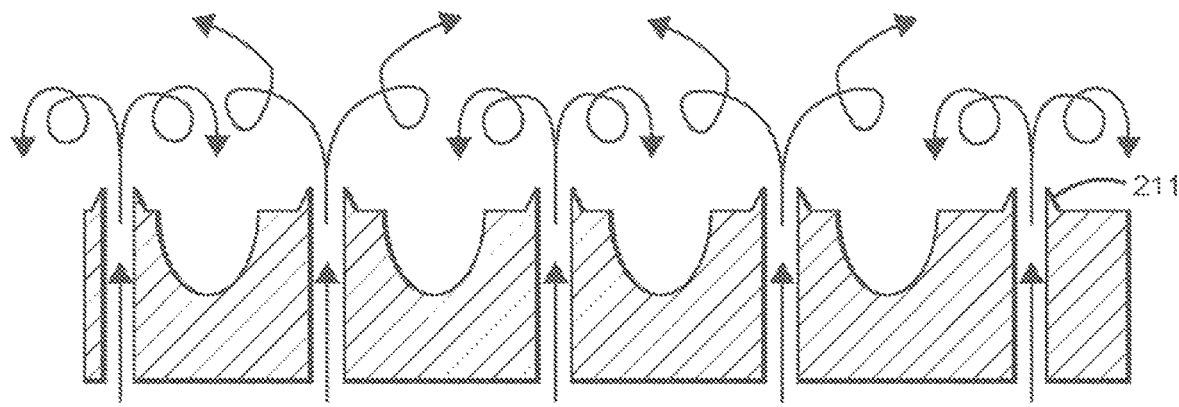

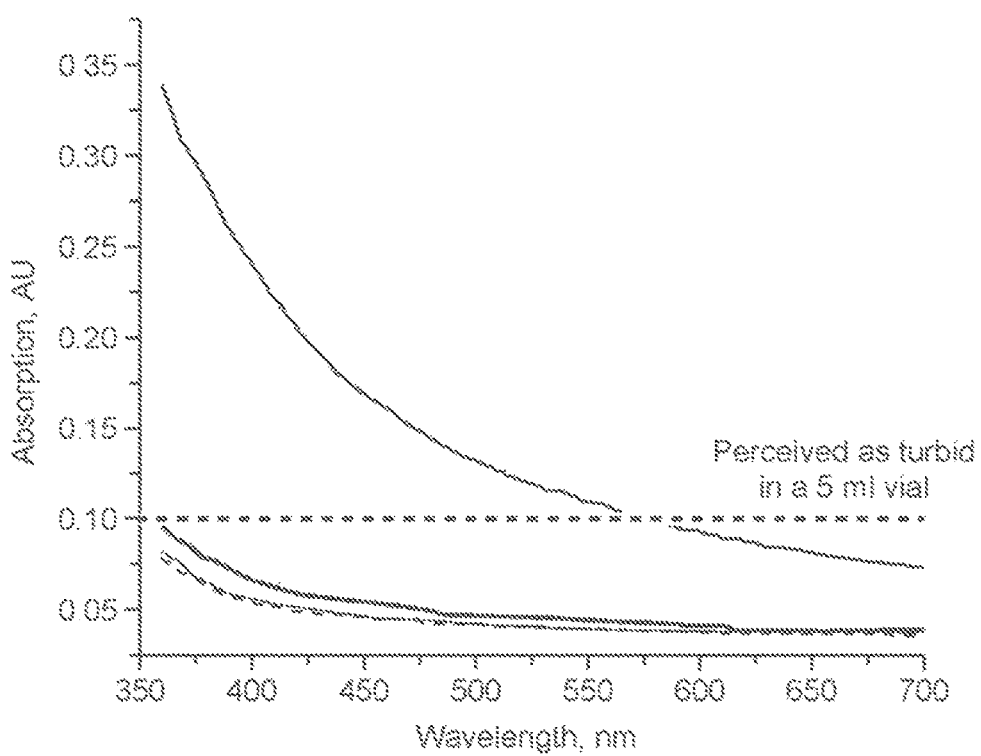
FIG. 7
FIG. 8A
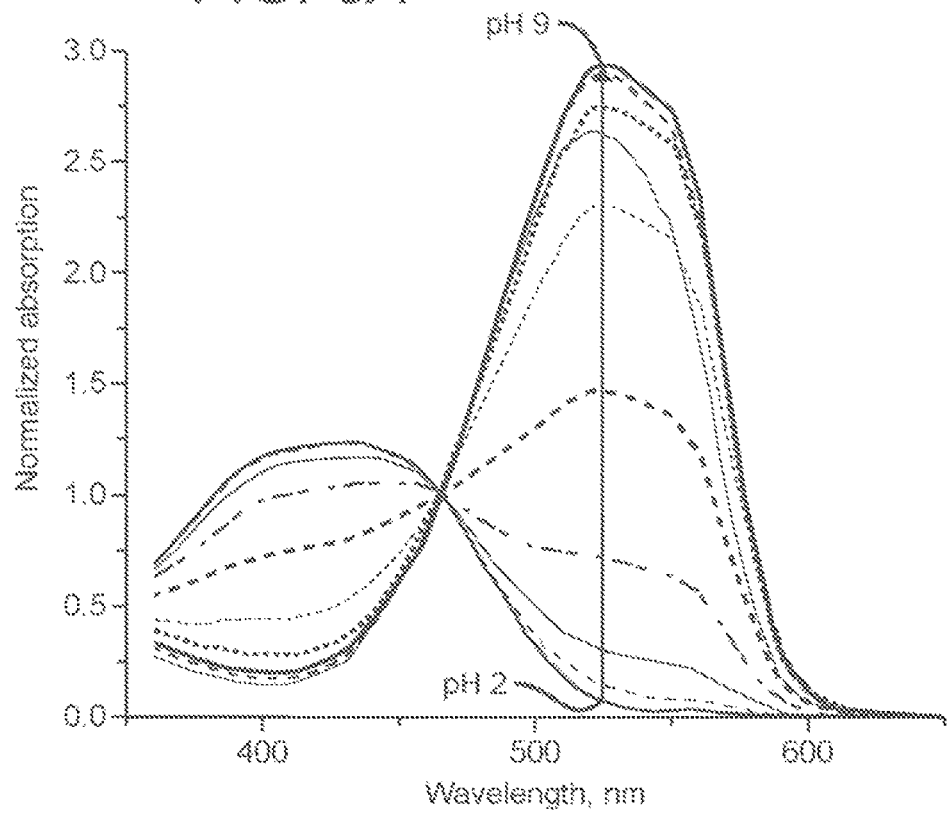

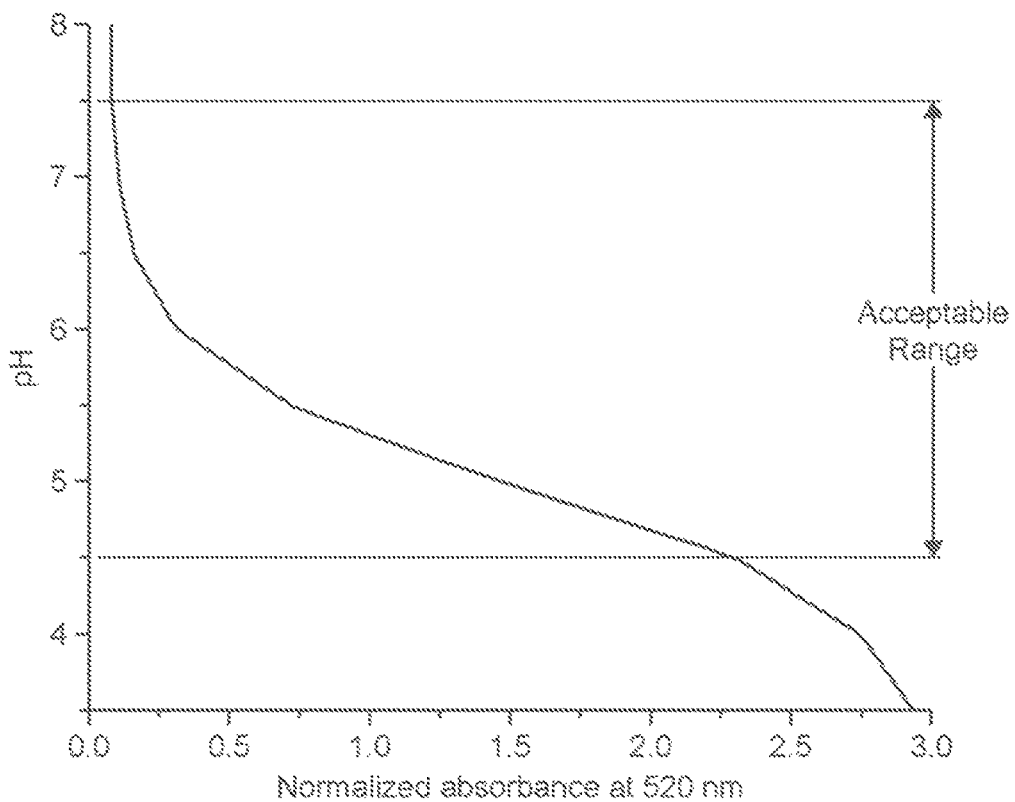
FIG. 8B
FIG. 9
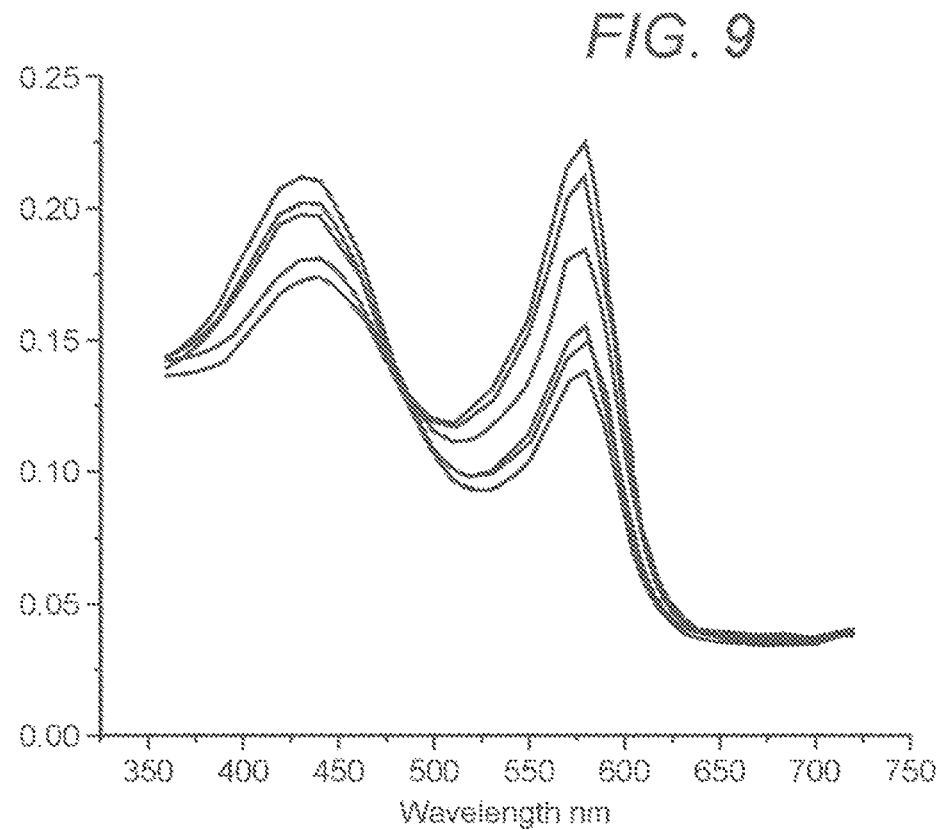

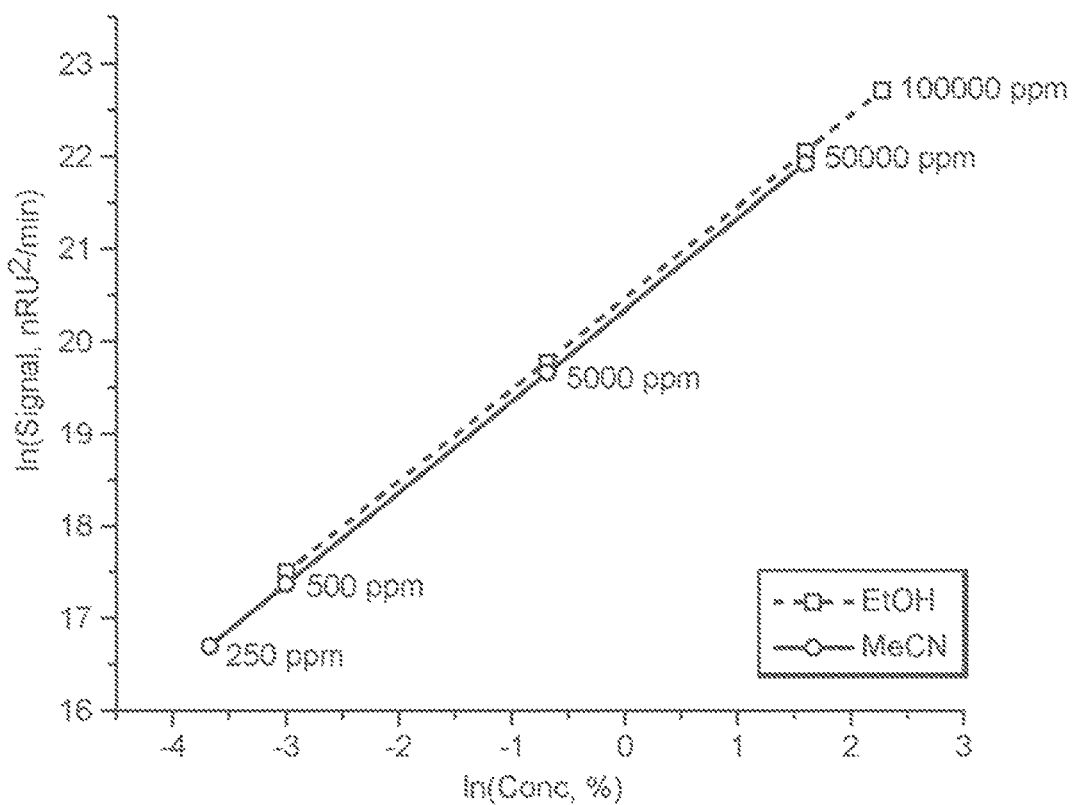
FIG. 12A
FIG. 12B
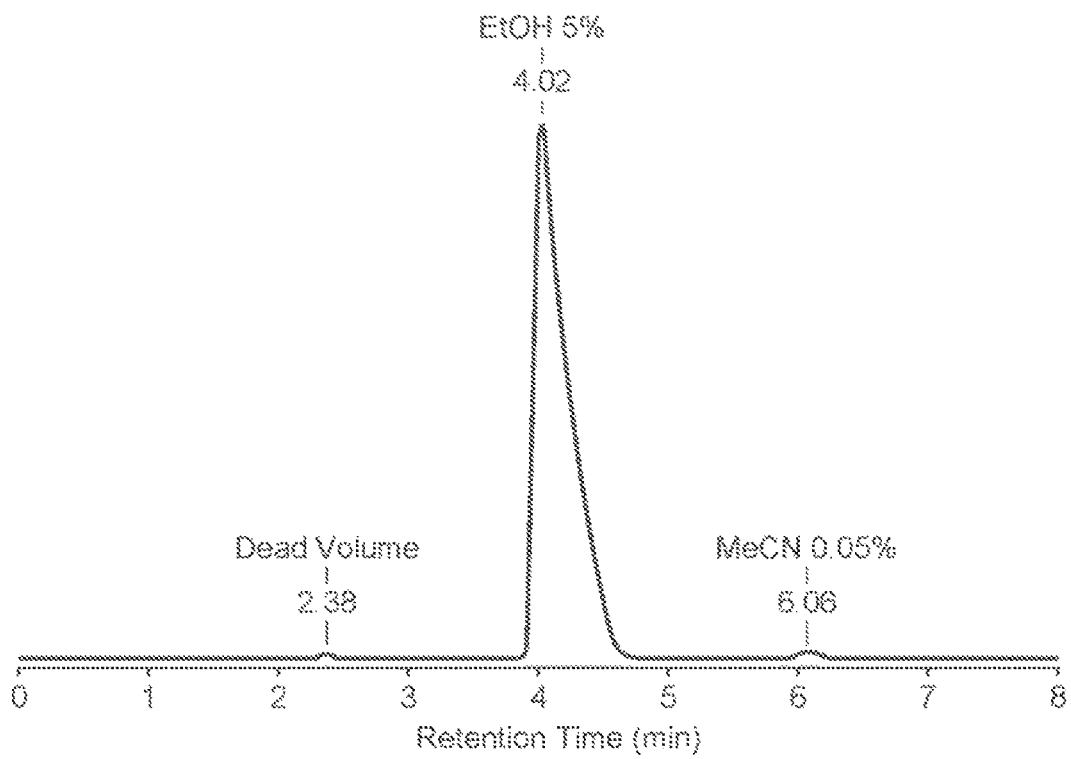

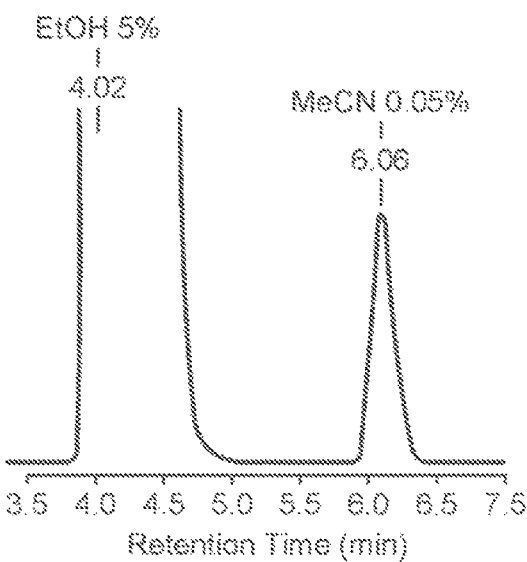
FIG. 12C
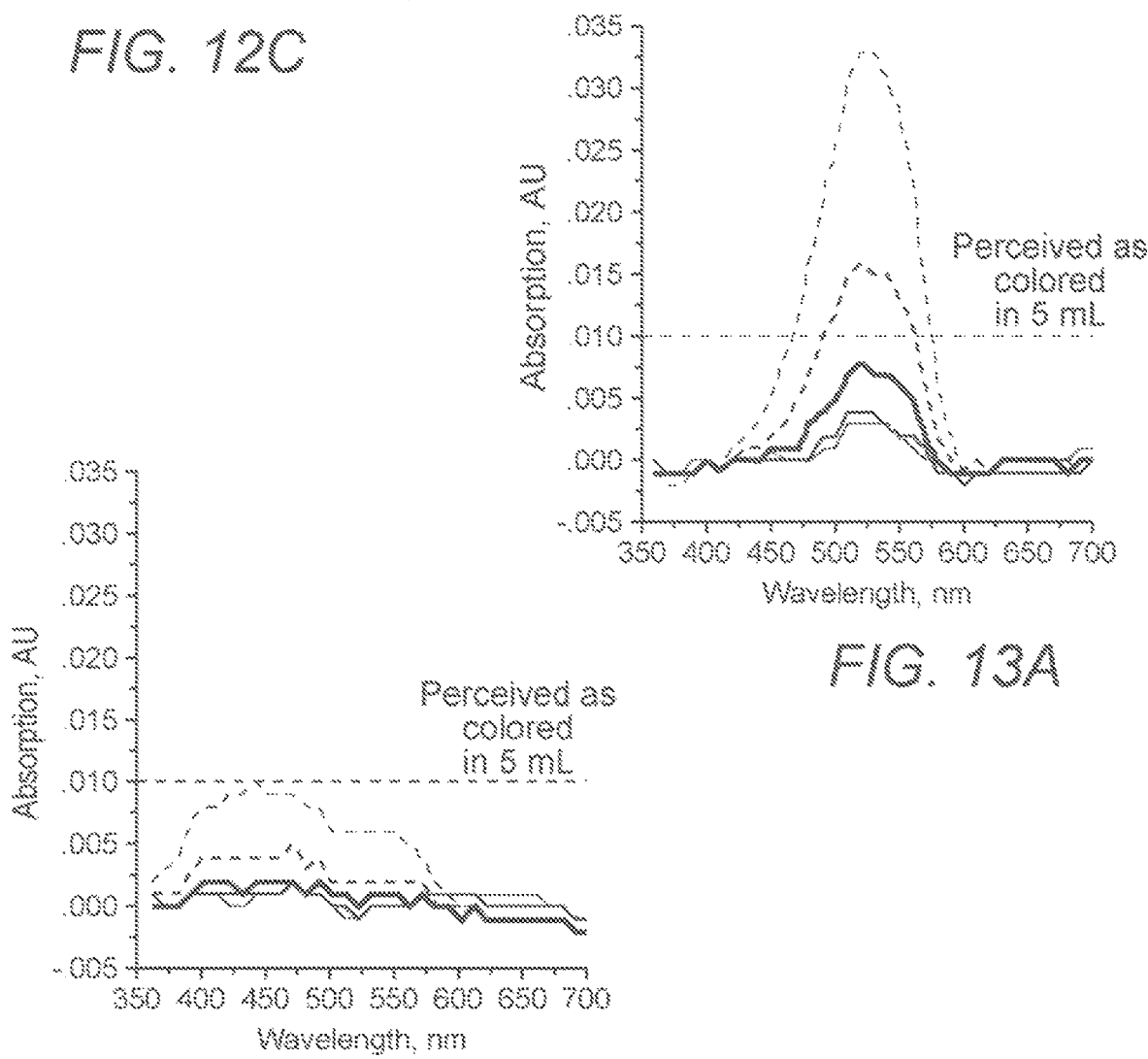
FIG. 13A
FIG. 13B

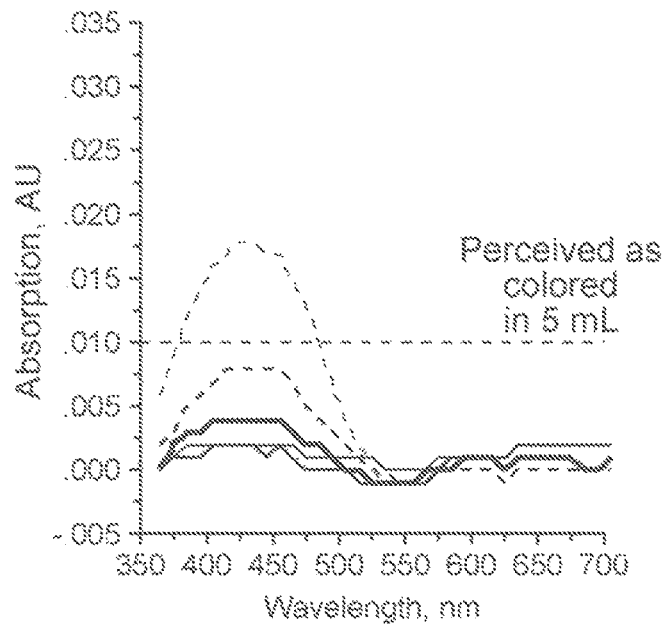

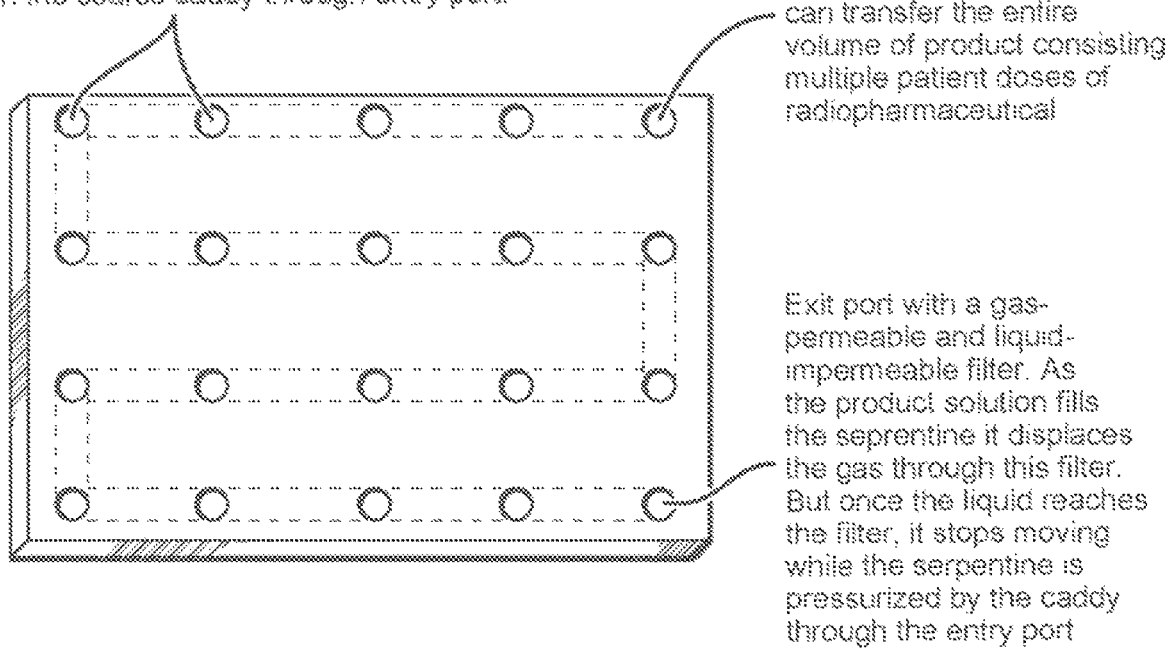

Openings in the serpentine (exit ports) that have septa pierce-able by caddies designed for aspiration of individual patient doses. As these caddies aspirate, the serpentine is refilled by the positive pressure behind liquid in the source caddy through entry port.

Entry point with a septum that may be pierced by a large volume caddy that can transfer the entire volume of product consisting multiple patient doses of radiopharmaceutical Exit port with a gas-permeable and liquid-impermeable filter. As the product solution fills the serpentine it displaces the gas through this filter. But once the liquid reaches the filter, it stops moving while the serpentine is pressurized by the caddy through the entry port

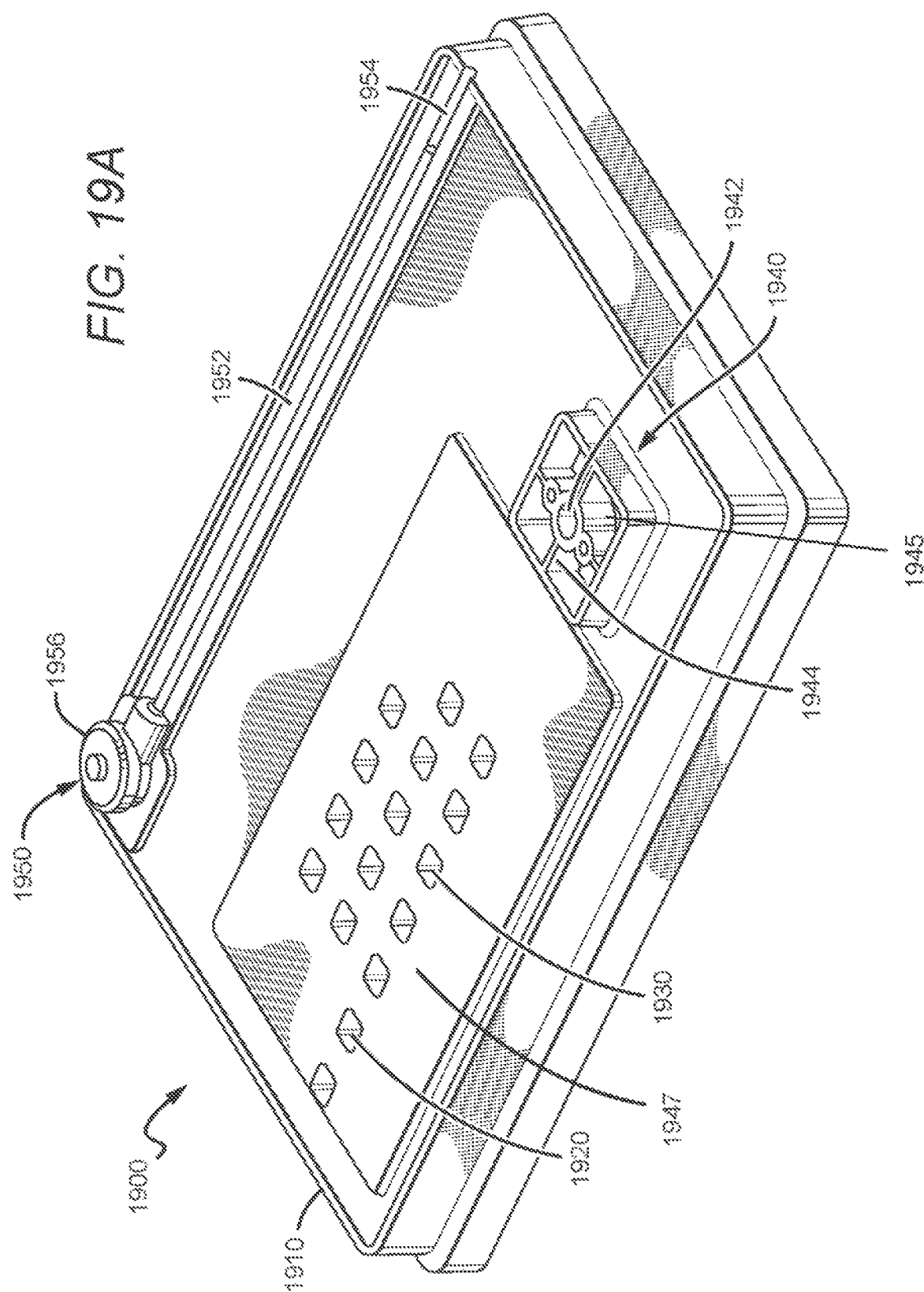

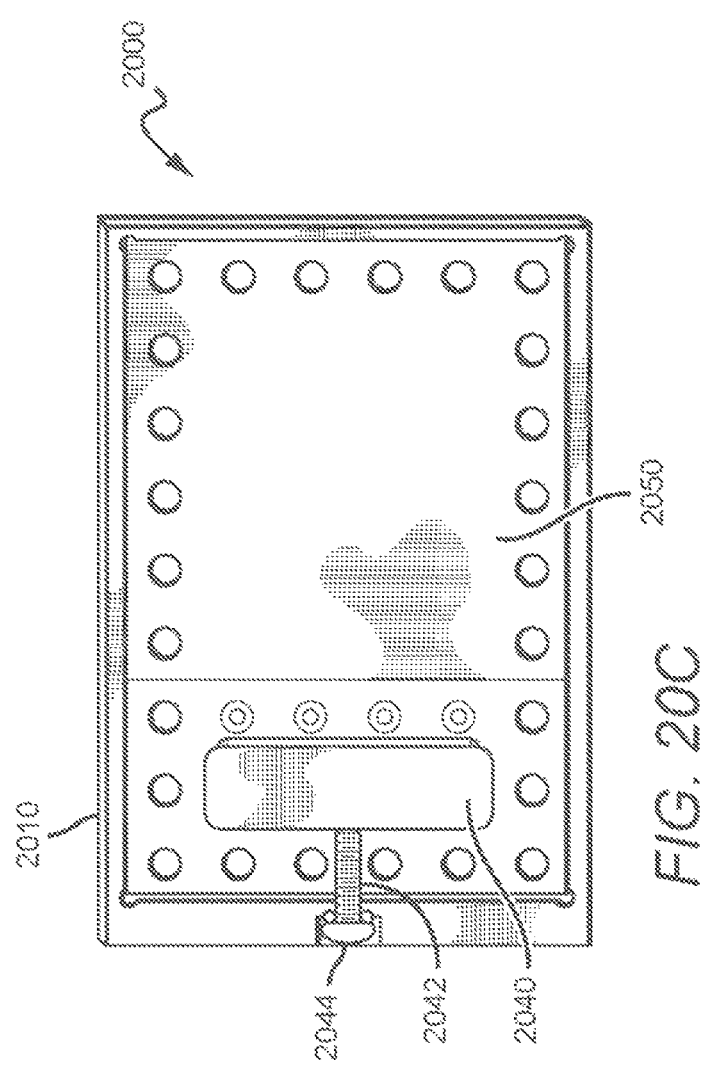
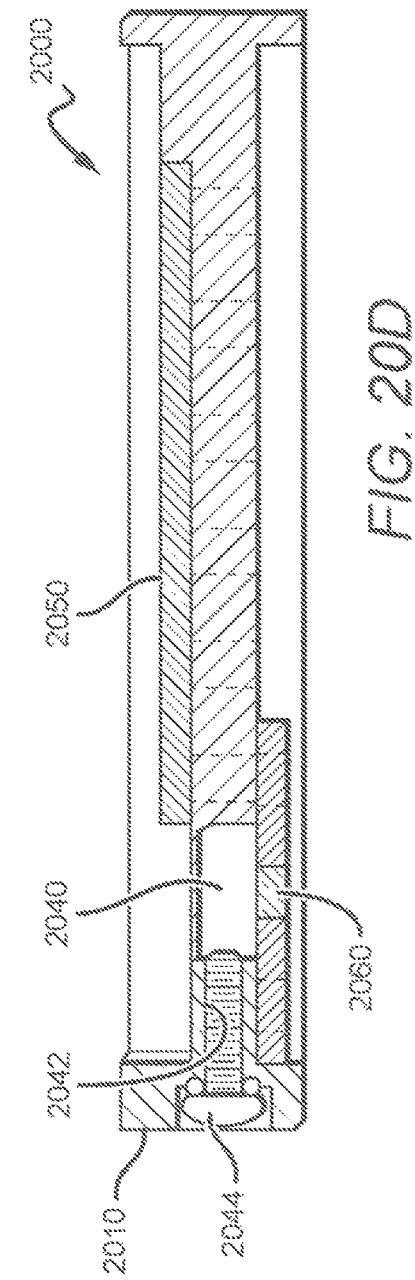
FIG. 20C
FIG. 20D

METHOD FOR DETERMINING A CONCENTRATION OF A SYNTHESIS COMPONENT IN A RADIOPHARMACEUTICAL SAMPLE

CROSS-REFERENCE TO RELATED APPLICATIONS

This application is a divisional of U.S. patent application Ser. No. 14/866,684, filed Sep. 25, 2015, which claims the benefit of U.S. Provisional Application No. 62/056,529 filed on Sep. 27, 2014, and U.S. Provisional Application No. 62/171,183 filed Jun. 4, 2015, and is a continuation-in-part of U.S. patent application Ser. No. 14/191,293 filed on Feb. 26, 2014. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

GOVERNMENT LICENSE RIGHTS

This invention was made with government support under R43CA192499 awarded by the National Institutes of Health and IIP-1446677 awarded by the National Science Foundation. The government has certain rights in the invention.

FIELD OF THE INVENTION

The following description relates to systems and devices for chemical synthesis and/or analysis, and methods of using the same, in particular radiopharmaceuticals utilized in medical imaging such as Positron Emission Tomography (PET), or Single-Photon Emission Computed Tomography (SPECT); and/or therapy with such radioactive compounds.

BACKGROUND

The following description includes information that can be useful in understanding the inventive concept. It is not an admission that any of the information provided herein is prior art or relevant to the presently claimed invention, or that any publication specifically or implicitly referenced is prior art.

Practice in the field of radiopharmaceuticals is often reliant on the presence of a radiopharmaceutical production facility located at or near the site of use. This is particularly true in the case of radiopharmaceuticals utilized in imaging technologies (for example, positron emission tomography or PET scans), which often utilize relatively short lived isotopes. The short half-life of commonly used isotopes (for example, $^{18}F$) provides significant challenges to both synthesis of the desired radiopharmaceutical compound and quality testing of the resulting product that insures that it is both effective and safe prior to use. For example, at least twelve different tests can need to be performed on a synthesized radiopharmaceutical to verify that chemical identity, purity, specific activity, endotoxin concentration, etc. are suitable for use in a patient. Performing such testing on a radiopharmaceutical with a half-life that is measured in hours or minutes, therefore, requires a significant investment in testing equipment, appropriate laboratory space, and highly trained staff in order to complete characterization manually within the time constraints imposed by the isotope.

The chemical transformations needed for production and analysis of radioactive medical materials are preferably done using automated systems. Such modules provide for automatic handling of radioactive materials in a reproducible manner, and thus can both reduce personnel exposure to radiation and improve reliability of production and analysis. In typical radiochemical synthesis/analysis systems, raw materials and reagents are transferred from one location to another via valves and tubing, which require a "motive force" (e.g., provided by vacuum, peristaltic pumps, piston pumps, etc.). These can be installed at the time of the system manufacturing (with replacement during repair or maintenance (i.e. permanent devices), or can be incorporated into a module or cartridge used for a single production or analysis run (i.e. disposable devices). While such systems can greatly simplify production and/or analysis of PET and SPECT radiopharmaceuticals, several decades of practice have revealed a number of drawbacks to these systems.

Transfer of the liquid reagents can result in considerable loss of the liquid material on transfer surfaces (particularly at low volumes) due to small droplets that are retained on the inner walls of such surface and the necessity of including "dead volumes" to insure accurate volume dispensing. This fundamental limitation directly impacts handling of small quantities of liquid. Synthesis of the radiopharmaceuticals is therefore limited to relatively diluted solutions, as milliliter scale volumes of solvents are needed for complete transfer of a certain amount of reagent. Similarly, analytical systems that rely conventional pumps and tubing for distribution of the samples have to use no less than hundreds of microliters of samples for reliable and quantitative transfer.

In addition, lines and/or valves can clog (particularly when used infrequently) and become pinched or leak upon wear. Such operational problems are not generally immediately evident and can be very hard to detect, as it is nearly impossible to inspect every inch of a complex liquid handling system.

Compared to conventional, manual "wet" chemistry, such automated system represent a fixed architecture that provides very little to no operational flexibility to chemists. The fixed scheduling, volume ranges, and reagent selections provided by dedicated synthesis and analysis systems necessitate that all functions of the system be fixed at the development stage. As a result introduction of new tasks, or improvement of existing methods, can require changes in fluid handling and processing capabilities that require redesign and redevelopment of all or part of such a system. Such changes can necessitate changes in hardware, electrical, electronic, and software components, and can lead to a need to recertify such systems with regulatory agencies. Attempts to design systems that can accommodate new functionalities have inevitably led to complicated schemes as all functionality, whether it is needed or not at the time the system is developed, must be anticipated. Therefore, most of the existing radiochemistry systems can only perform a limited number of predefined operations; i.e., they lack operational flexibility.

The limited operational flexibility of these machines also results in an inability to recover from an error. Generally, if one operation within a run is not performed as expected, the entire run has to be abandoned and the synthesis or analysis has to be reinitialized, for example by performing a cleaning cycle or by inserting a new cassette. That is because most systems execute tasks in a pre-defined sequence, with no option or intelligence to repeat, skip, or change the order of individual steps in order to accommodate errors. As a result, current systems have only one chance to complete their task, with no option to recover from minor errors (such as incomplete liquid delivery).

In addition, systems that rely on permanent liquid handing devices will require complex cleaning procedures after each liquid transfer in order to prevent contaminants in the subsequent procedure. In some instances the need for this can be reduced by using a disposable component to contact the liquid (for example, a disposable pipette tip). In the case of systems based on permanent pumps, lines, and valves a complex cleaning/drying cycle is generally performed following each run in order to ensure that no contaminants are left in the lines. Extensive cleaning validations are required. This problem was mitigated in synthesis systems by the use of disposable cassettes where a new set of lines is used for each run. However, some lines in the cassette are often used for several consecutive transfers and the operation protocol has to incorporate interim cleaning steps in order to eliminate carryover.

A large number of systems for radio-synthesis and/or analysis of radiopharmaceuticals have been reported and patented, which rely on plumbing and valves to route liquids. Those using disposable cassettes still contain liquid handling lines and valves, and still must conform to the rigid and inflexible design of the host system. In such implementation the complexity of the overall system is increased by the mechanical interface between the valves and their actuators, and the electronic and liquid connections between the disposable and the permanent parts of the system.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for systems and methods that facilitate rapid, accurate, and flexible synthesis and/or analysis of compounds, particularly radiopharmaceuticals.

SUMMARY OF THE INVENTION

The inventive subject matter provides apparatus, systems and methods in which enable synthesis and/or analysis of chemical compounds on a palette-based platform. Suitable compounds include radiopharmaceuticals. Palettes utilized for analysis can include both test wells and separation devices, and can include low thermal mass, thermally isolated portions that equilibrate rapidly to external temperatures. Methods are preferably selected to provide optically readable results, which facilitates obtaining all test results from a single reader.

One embodiment of the inventive concept is a test fixture for analyte characterization that includes a first testing region comprising a test well and a second testing region comprising a separation device, wherein the separation device comprises a separation medium and an observation region. Such a test fixture can include a reagent-containing well, such as a reagent-containing well that includes a reagent utilized in a test performed on the test fixture. Typical tests include color, clarity, pH, 4,7,13,16,21,24-hexaoxa-1,10-diazabicyclo-(8.8.8)-hexacosane concentration, radionuclidic purity, radioactivity concentration, pyrogen concentration, radiochemical identity, radiochemical purity, specific activity, organic solvent concentration, and sterility. Suitable separation devices include a capillary tube, a microcolumn, a channel, a trough, and a coated plate, which in turn can include a separation medium such as silica, anion exchange media, cation exchange media, size exclusion chromatography media, reverse phase media, hydrophobic interaction chromatography media, affinity chromatography media, pseudo-affinity chromatography media, agarose, polyacrylamide, and agarose/polyacrylamide mixtures. Such a test fixture can include a loading region configured to direct at least a portion of a sample to the separation device. In some embodiments the test fixture includes a third testing region, where the third testing region is thermally isolated from the first testing region and has a low thermal mass.

Another embodiment of the inventive concept is a test fixture for analyte characterization that includes a first testing region that includes a first test well and a second testing region that includes a second test well, where the second testing region is thermally isolated from the first testing region and the second test well has a low thermal mass. Such a test fixture can include reagent-containing wells.

Another embodiment of the inventive concept is a method for performing a first test and a second test having different temperature requirements, where a test fixture is provided that includes a body, a first testing region, and a second testing region, where the first testing region is in thermal communication with the body and the second testing region is thermally isolated from the body. A first test reagent for performing a first test is added to a first well of the first testing region and a second test reagent for performing a second test is added to a second well of the second testing region, where the first test is tolerant of temperature change and the second test is intolerant of temperature change. While at a first temperature, a first portion of a sample is brought into contact with the first test reagent and a second portion of the sample is brought in to contact with the second test reagent. The test fixture is then transferred to a temperature controlled environment that is held at a second temperature that is different from the first temperature. The test fixture is incubated in the temperature controlled environment for a period of time in excess of that necessary for the second testing region to reach the second temperature, then a test result is determined from the first well and from the second well. The second test region can reach the second temperature more rapidly than the first region and thus has a longer period (for example, 50% or more of the total incubation time) where it is in thermal equilibrium with the temperature controlled environment. The first temperature can be lower or higher than the second temperature. In some embodiments the second testing reagent includes a reagent for determining pyrogen content.

Another embodiment of the inventive concept is a test fixture that includes a first testing region that includes a test well and a second testing region that includes a separation device, where the separation device includes a separation medium and an observation region. Such a system also includes an optical reader, which can be configured to retrieve optical data such as optical density data, optical scatter data, nephelometry data, refractive index data, optical polarization data, fluorescence data, phosphorescence data, and luminescence data. Such an optical reader can transmit data to a computer system, and can be configured to collect a series of measurements in real time. Such a test system can include one or more fluid handling devices.

Another embodiment of the inventive concept is a method for characterizing an analyte, where a test fixture is provided that includes a first testing region (which includes a test well) and a second testing region that includes a separation device, where the separation device includes a separation medium and an observation region. A first part of a sample is dispensed into the test well and a first reagent are transferred to the test well. A second part of the sample is transferred to the second test region. A first result is read from the test well and a second result is read from the observation region. This second result can be obtained without the use of a fluorophore or a scintillant, for example by a measurement of Cherenkov radiation. In a preferred embodiment the first result and the second result are obtained from the same reader. In such a method the first result can be one or more of color, clarity, pH, 4,7,13,16, 21,24-hexaoxa-1,10-diazabicyclo-(8.8.8)-hexacosane concentration, radionuclidic purity, radioactivity concentration, pyrogen concentration, organic solvent concentration, and sterility. The second can be one or more of radiochemical identity, radiochemical purity, and specific activity. In some embodiments a series of results are gathered from the observation region in real time.

Another embodiment of the inventive concept is a kit for characterizing an analyte that includes a test fixture that includes a first testing region which has a test well and also includes a second testing region that includes a separation device, which has a separation medium and an observation region. The kit also include a reagent storage device that includes reagents for performing a test, and instructions for use. In such a kit the test fixture or the reagent storage device are configured to be consistent with the ANSI/SLAS 1-2004: Microplates Footprint Dimensions standard. In a preferred embodiment the test fixture is a unitary, single use device.

Another embodiment of the inventive concept is a device for testing microbial contamination, which includes a body that includes an access channel where the access channel has a first aperture, a second aperture, and a lumen. The lumen lies between and allows fluid to pass between the first aperture and the second aperture. The device includes an incubation chamber that has an observation window, and is in fluid communication with the second aperture of the access channel. The device also includes a gas collection chamber that is in fluid communication with the incubation chamber. At least a portion of the gas collection chamber can be displaced both vertically and horizontally from the incubation chamber. The incubation chamber of the device can include a growth medium, which can have a volume that is selected to fill the incubation chamber and not fill the gas collection chamber. In preferred embodiments, the volume of the growth medium is selected so that the growth medium/gas interface is not observable through the observation window. In some embodiments the device includes a sealing device that can block the first aperture of the access channel.

Another embodiment of the inventive concept is a test fixture for analyte characterization that includes a test well that has a central axis and a top opening that has a first diameter. The test well also has a side wall that extends downwards from the top opening, having a lower edge and a curvilinear portion that subtends towards the central axis. The test well also includes an observation window that is joined to to the lower edge of the side wall and has a second diameter, where the second diameter is less than the first diameter (for example. 25% or less of the measurement of the first diameter). In some embodiments the test well includes a loading region, where the side wall extends downwards vertically from the top opening. In a preferred embodiment the test well has a circular cross section.

Another embodiment of the inventive concept is a test fixture for characterizing a radiopharmaceutical that includes a single use, unitary test palette that includes two or more test regions, wherein each of the test regions includes an optically transparent region utilized for data collection, and further includes one or more flow regions, where each of the one or more flow regions is configured to support unencumbered flow of a fluid (i.e. flow that can encounter separation media but does not encounter a valve or similar device). Such a single use, unitary test palette is configured to retain a sample (or any portion thereof) that include a radiopharmaceutical and that has been applied to the single use, unitary test palette. The flow region of such a palette can include a separation medium.

Another embodiment of the inventive concept is a method for optical characterization of 4,7,13,16,21,24-hexaoxa-1, 10-diazabicyclo-(8.8.8)-hexacosane. In such a method a sample comprising 4,7,13,16,21,24-hexaoxa-1,10-diazabicyclo-(8.8.8)-hexacosane is provided and contacted with a metal ion or metal ion complex for a period of time sufficient to form a heavy metal complex that absorbs visible or ultraviolet light. An optical density measurement is then obtained. In such a method the metal can be one or more of Aluminium, Barium, Beryllium, Bismuth, Cadmium, Calcium, Cerium, Cesium, Chromium, Cobalt, Copper, Dysprosium, Erbium, Europium, Gadolinium, Gallium, Gold, Hafnium, Holmium, Iridium, Iridium, Iron, Lanthanum, Lead, Lithium, Lutetium, Magnesium, Manganese, Mercury, Molybdenum, Neodymium, Nickel, Niobium, Osmium, Palladium, Platinum, Potassium, Praseodymium, Rhenium, Rhodium, Rubidium, Ruthenium, Samarium, Scandium, Silver, Sodium, Strontium, Tantalum, Technetium, Terbium, Thallium, Thulium, Tin, Titanium, Tungsten, Uranium, Vanadium, Ytterbium, Yttrium, Zinc, and Zirconium.

Another embodiment of the inventive concept is a method for optical characterization of acetonitrile in a sample, that includes providing a metal complex with a first optical behavior, contacting a sample that includes acetonitrile with the metal complex for a period of time sufficient to form a modified metal complex that has a second optical behavior, and measuring the second optical behavior. The first behavior and the second optical behavior can be one or more of fluorescence, absorbance, and luminescence. In some embodiments the step of contacting the sample includes reacting acetonitrile with a reactive amine or thiol. Metals suitable for use in the metal complex include one or more of Aluminium, Barium, Beryllium, Bismuth, Cadmium, Calcium, Cerium, Cesium, Chromium, Cobalt, Copper, Dysprosium, Erbium, Europium, Gadolinium, Gallium, Gold, Hafnium, Holmium, Iridium, Iridium, Iron, Lanthanum, Lead, Lithium, Lutetium, Magnesium, Manganese, Mercury, Molybdenum, Neodymium, Nickel, Niobium, Osmium, Palladium, Platinum, Potassium, Praseodymium, Rhenium, Rhodium, Rubidium, Ruthenium, Samarium, Scandium, Silver, Sodium, Strontium, Tantalum, Technetium, Terbium, Thallium, Thulium, Tin, Titanium, Tungsten, Uranium, Vanadium, Ytterbium, Yttrium, Zinc, Zirconium in any oxidation state.

Another embodiment of the inventive concept is a method of characterizing a radioactive substance. Such a method includes providing a single, unitary test fixture that has a first test site that includes a first radioactive sample, where the test fixture also has a second test site that includes a second radioactive sample. In such a test fixture the first test site and the second test site are positioned within the single, unitary test fixture such that radiation emitted by the first radioactive sample impinges on the second test site. In the method, a first optical signal is obtained from the first test site and a second optical signal is obtained from the second test site, however the radiation from the first test site does not contribute to the second optical signal. In a preferred embodiment either or both of the first optical signal and/or the second optical signal is a result of Cherenkov radiation.

Another embodiment of the inventive concept is a method of characterizing a radiopharmaceutical, where a single, unitary test fixture is provided that includes two or more test sites. A set of reagents suitable for performing at least four, 6, 8, or 10 tests selected from color, clarity, pH, 4,7,13,16, 21,24-hexaoxa-1,10-diazabicyclo-(8.8.8)-hexacosane concentration, radionuclidic purity, radioactivity concentration, pyrogen concentration, radiochemical identity, radiochemical purity, specific activity, organic solvent concentration, and sterility. In the method, at least 4, 6, 8, or 10 (respectively) tests selected from color, clarity, pH, 4,7,13,16,21, 24-hexaoxa-1,10-diazabicyclo-(8.8.8)-hexacosane concentration, radionuclidic purity, radioactivity concentration, pyrogen concentration, radiochemical identity, radiochemical purity, specific activity, organic solvent concentration, and sterility are performed on the single, unitary test fixture.

Still another embodiment of the inventive concept is a system for synthesis of a radiopharmaceutical that includes a synthesis apparatus used in radiopharmaceutical synthesis and a vial for collecting a product of radiopharmaceutical synthesis. A fluid path that includes a flow cell connects the apparatus and the vial, and provides fluid communication for transfer at least a portion of the product of radiopharmaceutical synthesis from the apparatus to the vial. In such a system the flow cell can be positioned such that at least 90% of the volume of the radiopharmaceutical product passes through it. Such a flow cell can an optical flow cell and/or an electrical flow cell. The flow cell can be connected to or integrated with tubing utilized for transferring the radiopharmaceutical product. Alternatively, the flow cell can be attached to or part of the vial. In some embodiments the flow cell is attached to or is part of a cap associated with the vial. In some embodiments the flow cell can be assessed by a device that is not permanently attached to the flow cell. The flow cell or subsystem containing the flow cell can be single use or disposable.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIGS. 2A to 2H depict various designs of embodiments of a palette with gas flow capabilities. FIG. 2A is a schematic illustration of a palette with a plurality of containers and an inlet for gas to flow through the palette and around the containers, but not through the containers. FIG. 2B is a cross-section view of a palette of FIG. 2A. FIG. 2C is a top view of the palette of FIG. 2A. FIG. 2D depicts gas flow through vertical channels of a palette of the inventive concept. FIG. 2E depicts an embodiment where channels of a palette are connected to channels of a fixture of an instrument to which the palette docks. FIG. 2F depicts a turbulent flow pattern of a gas flow associated with a palette. FIG. 2G depicts a laminar flow pattern of gas flow associated with a palette. FIG. 2H depicts a manifold associated with a palette to provide laminar flow over the top of the containers.

FIG. 7 shows UV-Vis absorbance versus wavelength spectra for a turbidity standard sample with various dilutions measured in a plate reader.

FIGS. 8A and 8B depict aspects of pH determination by methods of the inventive concept. FIG. 8A shows a normalized UV-Vis absorption versus pH value of a sample with Methyl Red pH indicator. FIG. 8B shows the pH value of a sample with Methyl Red pH indicator versus normalized absorption at 520 nm.

FIG. 9 shows UV-Vis absorbance versus wavelength for various concentrations of Kryptofix™.

FIGS. 12A and 12B depict detection methods for organic solvents. FIG. 12A shows a typical result measured using a refractive index detector versus the concentration of ethanol and acetonitrile. FIG. 12B shows an HPLC peak versus retention time for ethanol FIG. 12C shows an HPLC peak versus retention time for acetonitrile.

FIG. 13A, FIG. 13B and FIG. 13C depict typical UV-Vis absorbance versus wavelength results for a set of colored samples with various dilutions measured in a plate reader.

FIG. 14 illustrates an example system for parallel multiple dose dispensing according to an embodiment of the inventive concept.

FIGS. 19A to 19C depict various views of an exemplary test palette of the inventive concept, having both test wells and a separation device. FIG. 19A shows an orthogonal view that displays a top surface of the palette. FIG. 19B shows a side view of the palette. FIG. 19C shows an orthogonal view that displays a lower surface of the palette.

FIGS. 20A to 20D depict various views of an exemplary palette of the inventive device that s configured for sterility testing. FIG. 20A shows a front view of the palette. FIG. 20B shows a similar top view of the palette with a cover removed in order to display interior structures. FIG. 20C shows a horizontal cross section of the palette. FIG. 20D shows a vertical cross section of the palette.

FIG. 21A shows a vertical cross section of the test well. FIG. 21B shows a top-down view through the interior of the test well.

DETAILED DESCRIPTION

Figure 1:
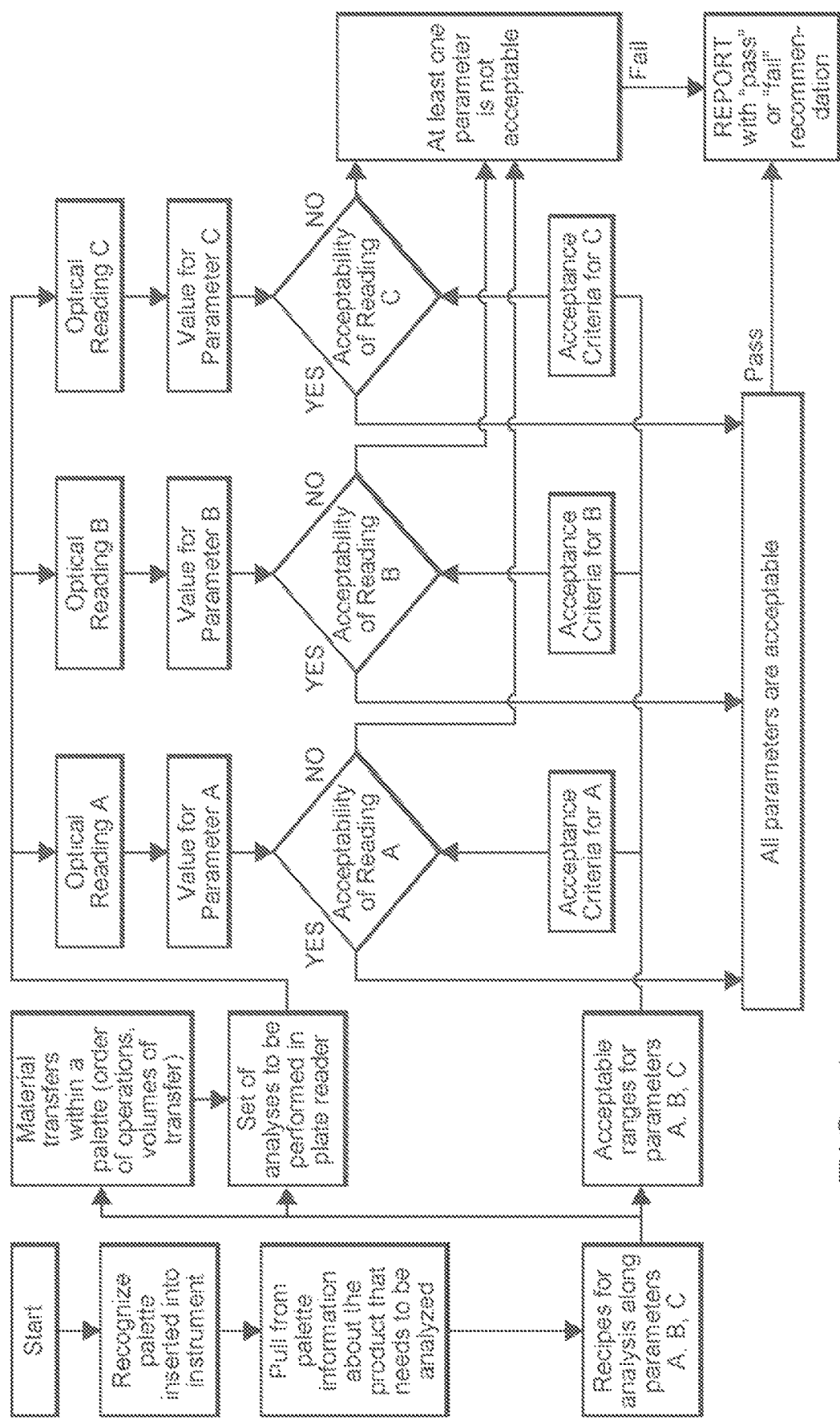
FIG. 1 is a flowchart of steps to implement an embodiment of the present invention.

Devices, systems, and methods of the inventive concept are directed towards simplified and efficient synthesis of radiopharmaceuticals and towards simplified and efficient testing or characterization of such radiopharmaceuticals prior to use. This can be implemented through the use of single use devices capable of performing a multitude of tasks involved in radiopharmaceutical synthesis and/or characterization. Such single use devices can be unitary, and in some embodiments can have or approximate dimensions corresponding to the ANSI/SLAS 1-2004: Microplates—Footprint Dimensions for microplate dimensions. In preferred embodiments, all tests utilized for characterization of radiopharmaceuticals produce results that can be determined optically.

Throughout the following discussion, references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

One should appreciate that the devices, systems, and methods of the inventive concept that are related to synthesis of radiopharmaceuticals provide rapid and efficient synthesis while minimizing exposure of laboratory personnel and utilizing minimal dedicated laboratory space, while also providing compact and secure containment of radioactive products and waste that greatly reduce the volume of radioactive waste while reducing the possibility of accidental release to the environment. Similarly, one should appreciate that devices, systems, compositions, and methods of the inventive concept related to characterization of radiopharmaceuticals provide rapid and accurate characterization of radiopharmaceuticals, while reducing the need for highly trained personnel in the performance of such tests and also reducing the amount of radiopharmaceutical required for testing purposes while providing containment and reducing the volume of radioactive waste products.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Some embodiments of the inventive concept are directed toward systems, devices, and methods for transferring materials including liquids, solids and gases, or a combination thereof. Such materials can be reagents for chemical reactions. The transfer can be used in systems and methods for carrying out chemical transformations, such as chemical reactions, synthesis, and/or analysis. One aspect according to one or more embodiments of the inventive concept is directed toward devices and methods utilizing one or more consumable/disposable components. Consumable or disposable means that the component, or module, can be disposed of, or recycled or refurbished following its role in the process. This recycling or refurbishing can occur at any time once the particular component has fulfilled its intended purpose. For example, one embodiment using consumable/disposable components includes a palette that carries everything needed for the analysis of the sample (except for the sample itself). The consumable can be discarded after the QC process is completed. For example, one can use a pipette with a disposable tip as a caddy to move liquids between wells/vials of the disposable palette.

The chemical transformation can be a synthesis and/or analysis of radiolabeled molecules. Such molecules can be used in nuclear medicine procedures such as PET scan, SPECT scan and/or therapeutic treatment using radionuclides. The system and device can also be used for quality control. An example of a synthesis (i.e., a synthesis procedure) of a radiolabeled compound, which can be performed by the inventive concept, is described in U.S. patent application Ser. No. 12/578,175, published on Apr. 15, 2010 as US2010/0093098 A1, and titled NONFLOW-THROUGH APPARATUS AND METHOD USING ENHANCED FLOW MECHANISMS, the entire content of which is incorporated by reference herein. Other transformations can be needed for analysis of samples containing radiolabeled molecules.

Such transformations can be facilitate through the use of a microfluidic system, a macrofluidic system or a combination of both. Such fluidic systems can be partially or totally automated. In one embodiment, the transformation utilizes or produces liquids of one microliter or greater. In another embodiment, the transformation utilizes or produces liquids of 100 milliliters or less. In yet another embodiment, the transformation utilizes or produces liquids of more than 100 milliliters, for example, one liter or greater. In yet another embodiment, the transformation utilizes or produces liquids less than one microliter, for example, 900 nanoliters or less.

A system according to one or more embodiments of the inventive concept can include a set of disposable components (for example a probe, needle, pipette, or pipette tip) for the transfer of materials (such as reagents or radiopharmaceuticals) from one location to another. Such a disposable component can be "simple", that is, made of only one piece of homogeneous material and at some point performs its function such that the material to be transferred inside this disposable component does not come into physical contact with other disposable components of the system (i.e., the fluid and/or solid inside one of the disposable components is isolated from other disposable components or the fluid or solid inside another one of the disposable components). Such disposable components can also have no direct liquid connection or electronic connection with a permanent parts or fixed portion of a device or system of the inventive concept. For example, a system according to one or more embodiments of the inventive concept can include a palette-caddy system.

Palette-Caddy System

In some embodiments, the system and/or device can use a "Caddy" and "Palette" system, in place of conventional tubing, valves for all or part of the system and/or device, and can additionally provide a motive force for transferring materials.

A "caddy" is a disposable and/or single use container used in material transfer. For example, a caddy can be used to transfer a liquid (such as a chemical solution) between two or more locations, i.e., from one location to another. When a liquid needs to be transferred, it is "picked up" by being pulled into a caddy at one original location. The caddy is then moved to the new location and its contents are delivered and "dropped off". As such, a liquid sample is transferred via "pick-up" and "drop-off" mechanism via a caddy. The caddies are designed to be easily disposed of or exchanged after every transfer operation. Examples of a caddy include (but are not limited to) a movable vial, a pipette tip, a disposable syringe, a loop, a needle, or the like. Such a caddy can be easily (and automatically) removable and/or exchangeable after each operation performed. This advantageously reduces or eliminates any chances of contaminating the reagents involved in different transformations. Various means of moving materials in and out of a caddy can be used such as evaporation of liquid by heating, condensation of a gas by cooling, gravitational or electrostatic transfer of solids and fluids, gravitational transfer of liquids, vacuum, pneumatic or hydraulic operation, etc. The volume of a caddy can be nanoliters to liters, for example, a caddy can be able to transfer samples of microliters, milliliters, or liters in size.

A "palette" can be a device designed to include a plurality of functions and/or reaction or testing sites, for example a plurality of liquid containers accessible via one or more caddies. When more than one caddies are utilized, each of the caddies can operate independently of the others and can access different containers on one palette at the same time, or according to any desired sequence. A palette can be a structure (or device) suitable for containing multiple chemicals (solid, liquid, or gas) in fluidic isolation from one another. Here, the term "fluidic isolation" refers to a container without any connections to another container to allow the chemicals inside to flow out of its respective container. That is, the containers are not connected by any channels, tubing or valves to one another or another device. A palette can be designed to be disposable and can be used only for one production or analysis run. The container within the palette can be a well, a vial or other suitable means. For example, rather than having a physical wall that defines the boundaries of a container, the containers can be defined and separated by surface tension, electrostatic means or thermal control, such that materials deposited in one location of the palette are retained in that location and do not flow out of that location to mix with materials deposited in other locations. For example, the surface tension can be controlled by coating or depositing materials of different surface tensions in a desired pattern on a surface of the palette. For example, patches of high surface energy coating materials can be surrounded by a matrix of low surface energy coating materials.

A container can have a port accessible for the caddy. Such a port can include a reversible seal (for example, a septum, valve, or other reversible means of restricting fluid access) to be traversed by a caddy or otherwise docked by an inlet or outlet of the caddy. A palette can include containers of various volumes. For example, such containers can have a volume of 1 or more microliters, milliliters, or liters. Volume of the container can be adjusted, for example, can be reduced by using an insert of the appropriate volume. The container can be sealed, sealable, open, etc. One or more containers of a palette can be thermally isolated. Thermally isolated containers can be used to maintain low (or high) temperature inside the container or to prevent unwanted temperature fluctuations. Alternatively, such thermally isolated containers can have a low thermal mass that support rapid equilibration to a new temperature on changing the external temperature surrounding a palette.

Examples of suitable palettes include (but are not limited to) a multi-well plate, a rack of vials, or a custom piece of hardware designed to host one or more reagents (liquid, solid or gas) in a manner accessible to a caddy. In a preferred embodiment, a palette has dimensions (for example, external or outer dimensions that are consistent with the ANSI/SLAS 1-2004: Microplates—Footprint Dimensions standard for microplates. Such dimensions advantageously provide a compact footprint that is compatible with a wide variety of automated handling and liquid dispensing systems and with a wide variety of optical readers. The palette can be made of a single monolithic piece of material and have no movable parts. An example of such a palette can be a micro well plate. Alternatively, the palette can include inserts of other materials (for example, UV transparent materials) and/or include movable parts providing flexibility to the palette. An example of such a palette can be a chain holding a container in its links. Yet another alternative can be a modular palette containing disposable and reusable parts, where materials held in the containers are only exposed to the disposable parts. An example of such a palette can include a holder and a set of disposable inserts such as a drum with holes in a portion of the drum, a tray with a grid of holes, or a set of smaller racks transported on a conveyor belt.

As disclosed above, according to some embodiments, a palette can exclude any valves, tubing junctions, or moving parts and can have one or more of the following characteristics: any container on the palette can be accessible at any time to a user or a machine; all components on a palette are in fluidic isolation (fluidly isolated) from one another; processes conducted on a palette can happen in any order or in parallel, rather than follow a strict sequence; fluids can or can not be fully contained, for example, each container can or can not be completely filled up with a fluid; liquid losses are not dependent on the transfer distance, as the liquid is transferred through the movement of the caddy, and does not flow over any of the distance to be transferred; materials can be transferred from any one location to any other location in any volume; precise metering of specific amounts of liquid sample is enabled at any step in the process; fluid is not required to flow between two locations within a palette; each container has no electronic or fluidic connection with the instrument; and the topology of the container is fixed, no change of the shape is mechanically actuated by the instrument.

A distinction between palettes and cassettes (such as cassettes utilized in other systems) is that a palette need not include channels or conduits utilized solely for fluid transfer and/or valves. They can include liquid containers (either permanently fixed or removable, either sealed or open), which can be in fluidic isolation (i.e., not in fluid communication) with one another. Palettes do not necessarily contain fluid transfer paths. According to one or more embodiments of the inventive concept, palettes do not contain networks of channels, junctions or manifolds.

Palettes can be provided with solids and/or liquids or combinations of solids and liquids. This is another feature that makes them different from cassettes which can not be packaged or stored with liquids in them and require the addition of liquids to be done shortly before their use (due to the presence of movable components that can easily create leaking points).

In some embodiments of the inventive concept, palettes do not contain any components that can move relative to one another. No moving or movable parts are included within a palette. However, the inventive concept is not limited thereto. For example, one or more moving parts can be included within a palette.

Figure 2A:
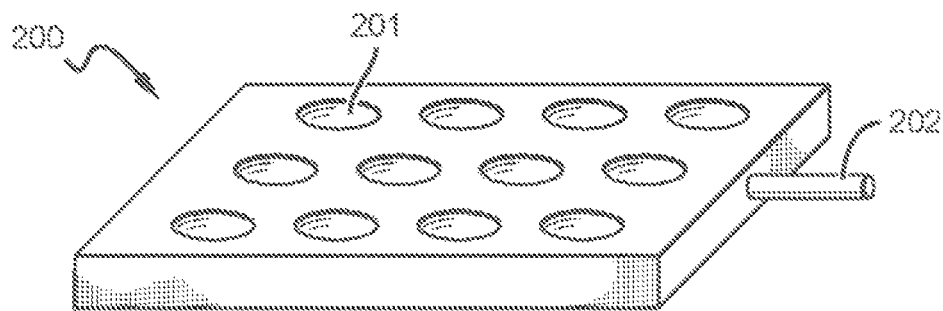

All containers with liquids inside can be sealed individually and/or permanently within a palette. These reagents can be accessible by a caddy traversing a respective individual seal during the process. In some embodiments a palette can further include a gas blanket to provide a bio-safety environment and thereby reduce or eliminate the need to install a complete device (e.g., the palette, an analytical instrument, etc.) in a laminar flow hood or clean room. Examples of such palettes can be designed according to FIGS. 2(A)-2(H), which illustrates various designs to assure a bio-safety environment around each palette. According to one or more embodiments of the inventive concept, a palette with a bio-safety environment, such as those described in these figures, can be utilized for radiopharmaceutical applications, but not limited thereto. For example, such a palette can be utilized for non-radiopharmaceutical applications, such as Immunoassays, blood analysis, and other in vitro diagnostic applications. Referring to FIGS. 2(A)-2(H), the gas can be connected to the palette or to a manifold below the palette that enables flow of gas through the palette once it is in place within the instrument and forms a gas blanket (i.e., a layer of gas) over the surface of the palette. In this case, rather than control the entire system (such as the palette with the samples on it and analytical instruments) by placing instruments in laminar flow hoods, a laminar flow micro environment is created at a specific location (without spatial confinement). FIG. 2(A) is a schematic illustration of a palette 200 with a plurality of containers 201 and an inlet 202 for gas to flow through the palette and around the containers, but not through (at least some of) the inside of the containers 201.

Figure 2B:
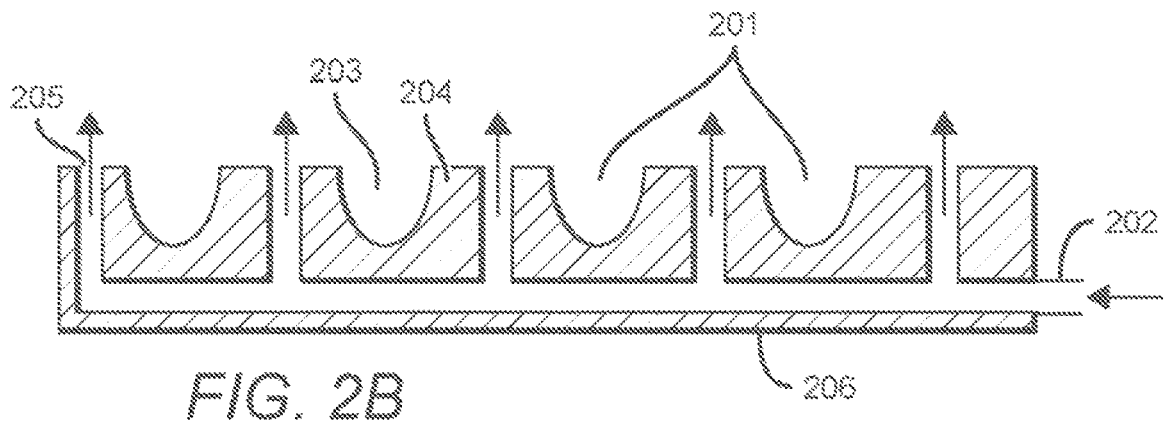

FIG. 2(B) is a cross-sectional view of the palette 200 of FIG. 2(A). Each container 201 has an internal space 203 for holding the reagents, surrounded by a wall 204. A gas channel 205 is formed between the walls 204 of neighboring containers 201 and/or between the containers 201 and the frame 206 of the palette.

Figure 2C:
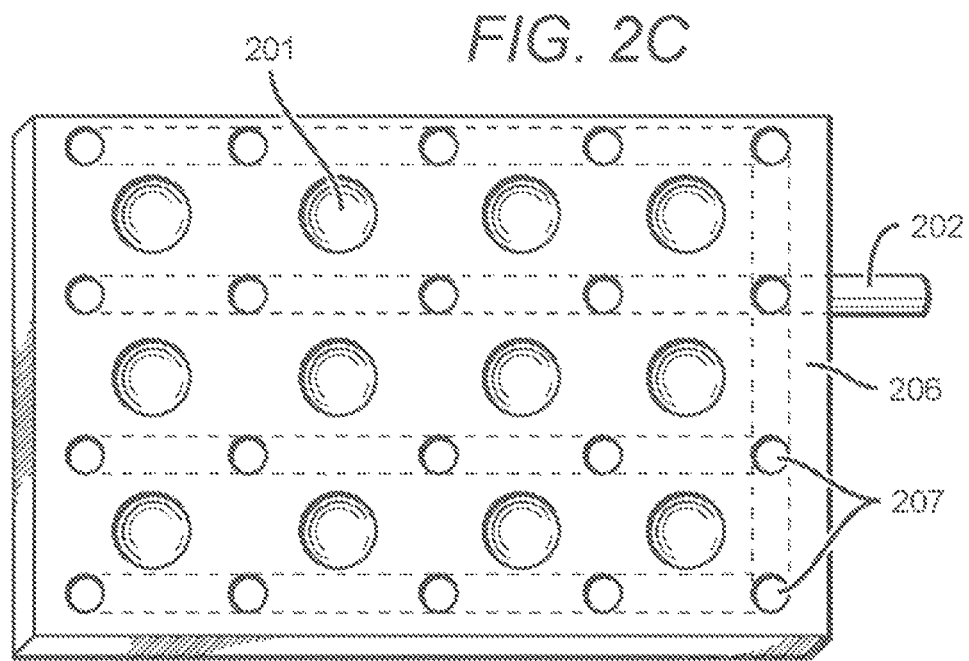
Figure 2G:
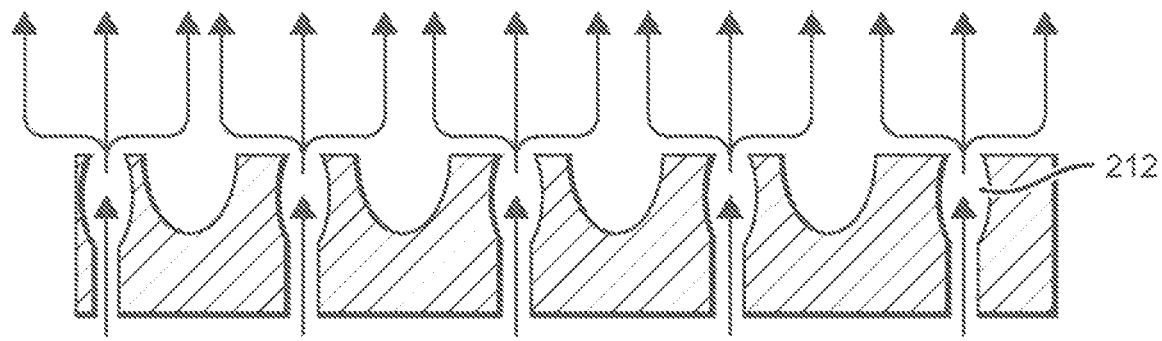
Figure 2H:
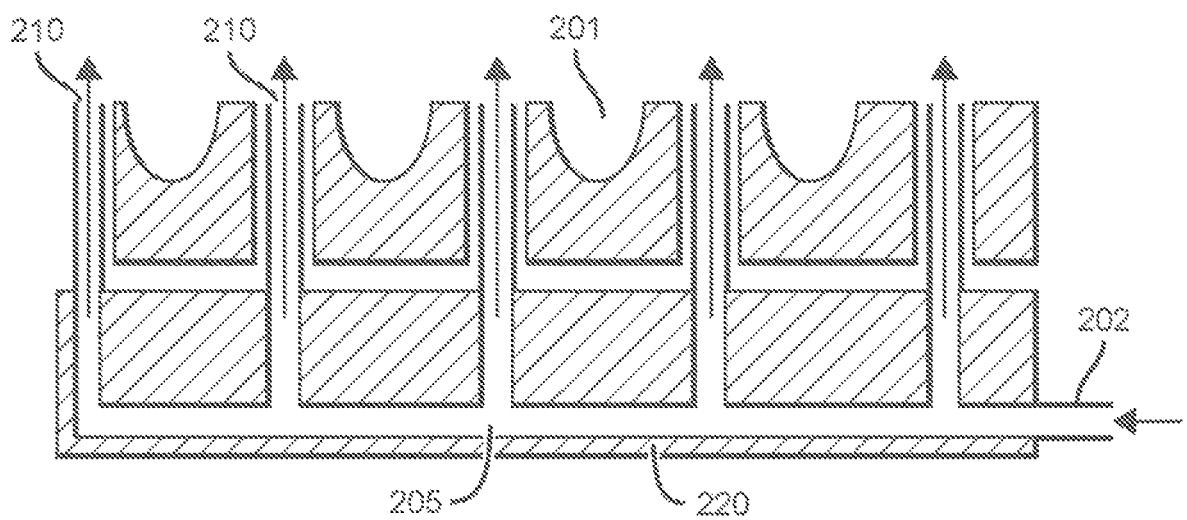

FIG. 2(C) is a top view of the palette 200 of FIG. 2(A). Each gas channel 205 can have a gas outlet 207 on the top surface of the palette. Referring to FIG. 2(D), the gas flow can be through vertical channels 205'. FIG. 2(E) illustrates an embodiment where the channels 205 within the palette 200 are connected to channels 208 of the permanent fixture 209 within the instrument to which the palette docks. Thus vertical gas flow through flow channels between adjacent containers 201 is a continuation of the gas flow and channels formed in the permanent instrument under the palette. Here, the gas can be introduced to the system through an inlet 210 located on the permanent instrument. The palette can be designed such that the openings where the gas leaves the palette are configured in such a way that they assure substantially laminar flow (as opposed to turbulent flow). For example, the shape of the flow channel, and/or the rate of the gas flow can be adjusted to ensure a laminar flow pattern. FIG. 2(F) illustrates a turbulent flow pattern, while FIG. 2(G) illustrates a laminar flow pattern. FIGS. 2(F) and 2(E) show some example features that can influence the flow pattern, but the features are not limited thereto and any suitable features to induce or enhance a laminar flow can be utilized. FIG. 2(H) shows a manifold with gas flow channel 205 and gas outlet 210 located on a permanent fixture 220 of the palette (such as the frame of the palette), to ensure laminar flow over the top of the containers.

Air routed to the palette can be passed through a high-efficiency particulate absorption (HEPA) filter to create an inert or sterile environment around the palette and in its contents. The gas can also be an inert gas.

In one embodiment as described earlier, a palette can have no walls or other vertical barriers to create wells or containers. The fluids and solids are confined to a location within a palette by means other than physical barriers. Such means can include (but are not limited to) surface tension, electrostatic means or thermal control. Surface tension, for example, can be controlled and not constant. Also materials can be moved along the palette by various means either involving caddies or not. Electrowetting techniques can be used as well.

Table 1 lists some features of a palette/caddy system described above that make it unique and distinct from other systems, for example, systems now used in production, analysis and dose dispensing of radiopharmaceuticals.

TABLE 1

Typical Distinctive Properties Of The Palette/Caddy System

Any container on the palette can be accessible at any time
All components can be fluidly isolated from one another
Processes can happen in any order or in parallel
Fluids can or can not be fully contained
Liquid losses are not dependent on the transfer distance
Material can be transferred from any one location to any other location in any volume
Precise metering of specific amounts of liquid sample can be enabled at any step in the process TABLE 1-continued Typical Distinctive Properties Of The Palette/Caddy System Fluid can not be required to flow in order to move between 2 locations within a palette
No electronic or fluidic connection with the instrument
The topology of the container is fixed, no change of the shape is mechanically actuated by the instrument
No valves, tubing junctions
No moving parts
In a 2-phase liquid-liquid mixture, any layer can be accessible at any time In some embodiments, the palette or its parts can be moved automatically providing for short and/or long-distance transfer of the palette. Long-distance transfer can be utilized in processes such as to deliver the palette behind shields for attenuating ionizing radiation. The "movable palette" mechanism can be, for example, useful in injecting new palettes or ejecting used ones from the system. It is also useful in the analytical applications where the liquid transformations within the palette are carried out via caddies in one part of the system for synthesis (such as one part of an instrument), but the analysis of the palette yielding measurements is carried in another part of the system for synthesis (such as another part of the instrument), requiring the entire palette to be moved from one location to another.

The containers within the palette can be configured to house various volumes of liquid, solid or gaseous reagents, or a combination thereof. It will be understood that virtually any reagents can be used with the present system. They can be delivered to the system within the palette and manipulated in a number of ways. In order to reduce or minimize the reliance on precise manual handling, the reagents can be delivered to the system in excess and the system will meter precise amounts as necessary for specific chemical reactions or analyses instead of pre-loading the precise amounts.

Material delivered to the system can be in the form of a pure chemical compound, a mixture of compounds, a solution of a compound, or a solution of a mixture of compounds. The material can be a radioactive compound. It can also be in a form of a compound reversibly adsorbed onto an inert carrier, or reversibly chemically bound to a carrier.

Delivered materials can play any role in the synthesis, analysis and dispensing process. Examples of typical delivered materials include: a reagent (liquid, solid or gas), a reactant, a catalyst, a phase-transfer reagent, an emulsifier, a pH buffer, an indicator, an intermediate, a product, a byproduct, waste, a solvent, and/or an absorbent. Some examples can include: $K_2CO_3$, Kryptofix-2.2.2™ (4,7,13,16,21,24-hexaoxa-1,10-diazabicyclo-(8.8.8)-hexacosane), acetonitrile (MeCN), mannose triflate (β-D-mannopyranose 1,3,4, 6-tetra-O-acetate 2-O-trifluoromethanesulfonate), acids, bases, water or any other gases or liquids.

It should also be understood that the system can be run by an operator via a computer and in some embodiments, can be automated. The system can include a computer and a computer-readable media for storing a program configured to operate the system.

In order to transfer materials from one location to another (from one container on a palette to another container on the same or another palette), a caddy can access a container on a palette and the material, or a fraction of thereof, can be transferred into the caddy. The caddy then moves to the destination and the material in the caddy, or a fraction of thereof, is unloaded. According to one embodiment of the inventive concept, unlike methods relying on fixed fluid transfer paths, the direction of the transfer can be determined during design and/or optimization of a specific operational program of an instrument, and is not determined by the design of the instrument. That is, the direction of the transfer can be determined after the design of the instrument. The direction of the transfer can even be determined (or even reversed) in real time during the instrument operation, for instance to adjust to new findings or correct for minor errors. If a content of a container needs to be delivered to several locations, it does need to pass through manifolds or distribution valves, but rather can be sequentially or simultaneously aspirated in caddies and delivered to the desired locations.

Further, in the caddy-palette design, the fluid path is previously unused and disposable for each transfer, thus eliminating a need for interim cleaning, or other limitations, such as having to follow a specific sequence of the reagents passing through a particular channel. In addition, each transfer can use a caddy best suited for that specific transfer in terms of material compatibility and/or volume being transferred. This is in contrast to other devices and systems, where tubes and valves are designed to be used with a predetermined (e.g., a specific) volume and are fixed on the instrument or on the disposable cartridge. Devices and systems according to embodiments of the inventive concept can operate a series of caddies, some used for smaller volumes, others used for larger volumes, thus reducing (e.g., dramatically reducing) losses during liquid transfer.

Using the palette-caddy approach, it is possible to transport material for greater distances than using the traditional tubing and valves. In the traditional devices and systems a longer fluid path is associated with a larger tubing surface that the transported material is exposed to; embodiments of the inventive concept provide for a constant surface area the transferred material is exposed to, thus constant and known losses of the material. Additionally, the surface-to-volume ratio can be kept low (e.g., to a minimum).

Additionally, the caddy-palette system allows precise metering of a material during any transfer, as long as the metering is allowed by the system operating the caddies. Other systems, for example, in the field of radiopharmaceutical production, described up to date only allow precise metering for a limited subset of the transfers within the system.

The palette-caddy system can be utilized to perform synthesis of a product, analysis of a product, or dose-dispensing and/or packaging of a prepared product. Such product can be a radiopharmaceutical. In yet another embodiment, a device or system can be used for all these purposes or any combination thereof: synthesis, analysis and dispensing. The processes occurring in each container are independent and, with simple precautions, any possibility of cross-contamination can be eliminated. Individual conditions can be created with one palette or for several palettes processed at the same time. In some embodiments, a portion of a system that is operating caddies can operate several caddies at the same time. These features can allow for parallel processing of several samples/performing several parallel syntheses, which is an enhancement over the fixed plumbing systems, which are only capable of performing one or very few processes at the same time. In another embodiment the system is configured to fill containers designated to deliver doses of product to specific patients at specific calibration times.

Existing instruments for the production, QC and dispensing of a radiopharmaceutical product do not facilitate integration of all these functions, since such integration would require connecting them physically with fluid paths and operatively with a program code. Within a system according to embodiments of the inventive concept, distinct hardware components would enable the 3 different processes. The system described here can use the same set of stationary hardware to accomplish all 3 processes (potentially even within the same palette).

In all of the embodiments listed above the amount of waste generated during the operation can be reduced or minimized. The main source of waste generated by a radio-chemistry instrument is the washing liquid used to clean a fluid path. As a liquid path does not need to be cleaned in the palette-caddy system, the chemical waste is limited to the reagents used in the synthesis/analysis. Thus the waste stays where it is generated and is disposed of together with the palettes and caddies.

Waste can be segregated according to the specific hazards, for instance radioactive waste and regular waste. Operational expenses can be reduced (e.g., significantly reduced) by reducing the amount of hazardous waste generated.

One palette can support one or more complete processes (synthesis of one product, analysis of one product, and/or another complete process) or sub-processes (a process that contains one or more operations where more than one palette is used for a complete process) whereas a caddy can support one operation (such as moving reagent from one location to another) before it is disposed. The rest of the system can be permanent. The only components that are exposed to reagents/samples are palette and caddy (both of which can be disposable).

In one embodiment, the system using palettes and caddies is self-sufficient, that is, performs a complete synthesis or analysis. In another embodiment, the system using palettes and caddies includes (or is integrated with) other machinery to complete the synthesis or analysis. This integration can be achieved via electronic data transfer and/or physical transfer of material between the machine using palettes/caddies and other machines.

In embodiments where the system is used for chemical (or radiochemical) synthesis, a palette loaded with all reagents can be inserted into the instrument. An auxiliary empty palette can also be loaded. Then via the use of caddies, the reagents are moved from one location to another in sequences and volumes predefined by a program being executed, in order to implement a series of chemical transformations.

In order to facilitate certain chemical transformations, temperature can be controlled in specific areas of the palette or over the entire palette. This can be accomplished by a heating/cooling element embedded in the part of a device that is in direct or indirect contact with the palette. For example, such a device can include a temperature controlled chamber in to which all or a portion of a palette is inserted. Alternatively, such a device can include a resistive element and/or a peltier element that is applied to a surface of the palette to raise or lower the local temperature. Individual caddies or portions of caddies can also be individually temperature controlled.

Separation of Chemical Compounds

Chemical transformations can include separation of chemical compounds. Separation (for example, for purification) of the chemical compounds in a palette-caddy system can be enabled through the utilization of filters, evaporation of liquids, liquid-liquid extractions, absorptions of selected molecules, and/or other suitable methods. For example, either the palettes or caddies can contain filters (or other forms of solid phase), operated in a way allowing the solution to be passed through a filter as it is moved into a caddy or moved to a new location on a palette. In some embodiments, evaporation (for example, for liquid removal and/or solute concentration) can be enabled via thermal control of specific locations within a palette and/or applying a flow of gas to a specific location to remove vapors.

Liquid-liquid extractions can be enabled by contacting two or more liquid phases within a location on a palette or within a caddy. In the former case, a caddy can (for example) transfer only one of the phases (for example, either of an upper or lower phase), while in the latter it can dispense one phase at one location and the second phase at a different location.

Absorption of selected molecules from solutions can be accomplished using palette containers filled with sorbent or caddies containing sorbent. The sorbent can, for example, be an ion-exchange resin for absorption of fluoride anion, C-18 modified silica for extraction of the non-polar solutes, polar resins for extraction of the polar solutes, affinity media, hydrophobic interaction media, dye interaction media, and so on. Other phase separation methods can be used within the inventive concept.

In some embodiments, a palette or a caddy can contain a preparative or analytical chromatographic fixture designed to support liquid chromatography (for example, HPLC, FPLC, or capillary chromatography), gas chromatography (GC), thin layer chromatography (TLC), and/or electrophoretic separations. For example, such a chromatographic or separation device can be dimensioned to have the capacity to provide preparative amounts (for example, an amount sufficient to act as a single dose) of a desired purified compound (for example, a radiopharmaceutical). In other embodiments such a chromatography or separation device can be dimensioned to provide separation of a fraction of a prepared sample for analytical purposes. In some embodiments such a chromatography or separation device can have both preparative and analytical functions, being dimensioned and supplied with a separation medium that provides sufficient separation resolution to distinguish the desired product from contaminants while also providing sufficient capacity for preparative purposes. In such an embodiment, the fluid path can contain a separation medium but is unencumbered (i.e. does not include valves or similar flow-modifying fixtures).

Exemplary Radiosynthesis Applications

Figure 6:
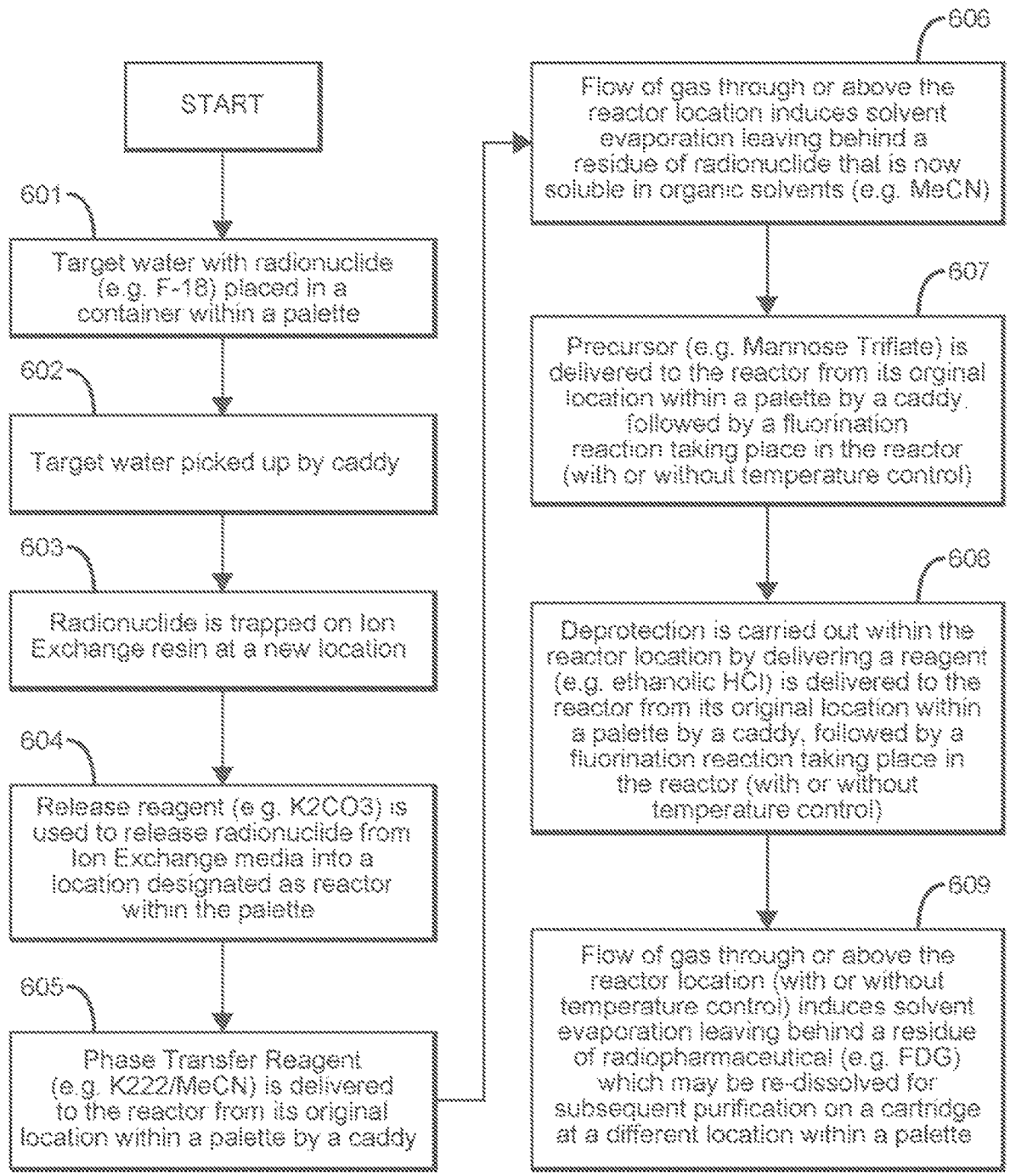
FIG. 6 depicts a flow chart showing a method of the inventive concept for synthesizing a radiopharmaceutical.

As an example, the present system can be used to synthesize a radiopharmaceutical. FIG. 6 is a flow chart illustration such a synthesis process. First in act 601, a target water containing a radionuclide can be placed in a container within a palette. Then in act 602, the container with the target water is picked up into a caddy and delivered at a new location on the same palette, or a different palette. The target water can then be passed through a bed of ion exchange resin to separate the radionuclide out of a dilute solution in act 603. A suitable compound, such as K2CO3 can then be used to release the radionuclide as a concentrated solution into another container or a reactor within the palette in act 604. Next, a suitable compound, such as a K222/MeCN solution, can be delivered from its container (for example, a container on a palette) to the reaction location in act 605. After the reagents have been mixed, nitrogen can be delivered to induce solvent evaporation (with or without concurrent heating) leaving behind a residue containing a complex containing the radio-active atom, for example, an [F-18]KF/K222 complex in act 606. Next, a precursor (for example, mannose triflate) can be delivered to the reactor in act 607. Deprotection can then be carried out by delivering a suitable compound, such as ethanolic HCl, into the palette container used as the reactor in act 608. Here, the reaction mixture can be heated. Then in act 609, the solvents can be evaporated, leaving behind a residue including the radiopharmaceuticals, which can be re-dissolved in water for subsequent manipulations such as cartridge purification. Alternatively, instead of evaporation, the solution including the radiopharmaceuticals can be diluted with water. Subsequent purification of the radiopharmaceuticals can be carried out by passing the crude solution through a series of cartridges. While the above example of a process used to synthesize radiopharmaceuticals using a palette-caddy system has been described with a set of acts, such a process can not include all of the acts, and the acts can not need to be executed in the specific order as described. Instead, one or more of the acts can be omitted, and one of more of the acts can be combined.

For example, a palette-caddy system can be utilized for the synthesis of fludeoxyglucose (18F) (FDG). First, [F-18] fluoride-containing target water can be placed in a container within the palette. Then it is picked up into a caddy and when it is being delivered at a new location, it is passed through a bed of ion exchange resin to trap [F-18]fluoride out of a dilute solution. K2CO3 can then be used to release [F-18]fluoride as a concentrated solution into another container or a reactor within the palette. Next, a K222/MeCN solution can be delivered from its container to the reaction location. After the reagents have been mixed, nitrogen can be delivered to induce solvent evaporation (with or without concurrent heating) leaving behind a residue containing an [F-18]KF/K222 complex. Next, the precursor (mannose triflate) can be delivered to the reactor. In processes where the volume of K2CO3 solution is substantially small, no evaporation can be necessary allowing direct addition of the solution of precursor and phase transfer reagent in an organic solvent to the concentrated aqueous K2CO3/[F-18] KF solution followed by fluorination reaction. This is an enhancement because such scenario avoids the need for evaporation steps which take time and can lead to some decomposition products. A palette-caddy system enables this scenario by the absence of the need for using larger volumes of water (required for long-distance transfer through tubes in conventional systems).

Deprotection is then carried out by delivering ethanolic HCl into the palette container used as a reactor. Once again, the reaction mixture can be heated. Then, the solvents can be evaporated, leaving behind a residue of FDG which can be re-dissolved in water for subsequent manipulations such as cartridge purification. Alternatively, instead of evaporation, the FDG solution can be diluted with water. Subsequent purification of FDG can be carried out by passing the crude solution through a series of cartridges.

Using the palette-caddy system, microliter samples can be synthesized in each container and ready for transferring to a desired location. Alternatively, a large volume of samples can be synthesized in a container of the palette, and microliter sized samples can be picked up from the container and transferred and dropped off at a desired location utilizing a caddy.

Analytical (Quality Control) Applications

Other embodiments of the inventive concept are directed towards systems, devices, and methods for assessing one or more quality control (QC) parameters of a radiopharmaceutical. In one embodiment of the inventive concept, one or more QC parameters is/are assessed using a palette that includes multiple wells. In another embodiment of the inventive concept, one or more QC parameters is/are assessed using a palette containing reagents on solid support. In yet another embodiment of the inventive concept, tone or more QC parameters is/are assessed with a palette being an assembly of individual containers.

In one embodiment a plurality of parameters being measured can include: sample color, clarity (i.e. turbidity), pH, phase transfer reagent content (for example, 4,7,13,16,21, 24-hexaoxa-1,10-diazabicyclo-(8.8.8)-hexacosane), radionuclidic purity, radioactivity concentration, pyrogen content, radiochemical identity, radiochemical purity, specific activity, organic solvent concentration, and sterility or any combination or subset thereof. In some embodiment of the inventive concept is directed to the method described above wherein when the outcome of one or more measurements is accepted, the sample is accepted on the criteria of one or more parameters. In other embodiments, a test pallet can be used to characterize 4, 5, 6, 7, 8, 9, 10, 11, and/or 12 of these parameters.

In an embodiment where the system is utilized for analysis, a palette is loaded with all the reagents necessary for multiple analytical procedures. An empty palette can also be loaded. Typically these are chemicals or materials whose interaction with the sample generates a signal that can be correlated to a specific chemical or physical property of that sample. The signal is an optical signal that is detected by a detector which is not in physical contact with the palette. In one embodiment, a light source and a spectrophotometer are used to generate and read optical signals. Using PET radiopharmaceuticals as an example, there are typically more than 10 parameters along which the product needs to be analyzed and the results accepted before the product can be used for human administration. In this case reagents that are contained at different locations within the palette are designed to yield signals corresponding to the required properties. The sample is the last material added to the palette before the latter is inserted into a stationary system, i.e., the analytical instrument. Alternatively, the sample can be distributed in specific amounts between different locations within the palette via the use of caddies after being inserted into the stationary system. In each of these locations a transformation takes place generating a signal that is correlated to a specific property. In some embodiments such signals are relayed to the stationary instrument without any part of the latter coming in contact with the sample or reagents. A separate set of locations on the same (or separate) palette can be used for calibration purposes, ensuring the calibration is always performed using the same batch of reagents as for the analysis. That value is then assessed against a limit or a range in order to deem that property acceptable or not acceptable according to pre-defined criteria. At the end of the process a multi-parametric report is generated and the palette can be disposed. In one embodiment the invention allows an operator to run several iterations of a process in parallel to assure increased accuracy or validity of the resulting measurement.

FIG. 1 is a flowchart of an operational process according to an embodiment of the inventive concept (for analysis applications). The sequence of operation can be stored on a suitable electronic storage medium, such as a computer-readable medium, which can be non-transitory, or RAM or ROM, or EEPROM or any other suitable electronic storage medium that can store electronic data. The operation can be object code, source code, or stored on a dedicated storage medium, either local to the user device or at a remote location and accessed as desired. Thus, the operation can be considered a module when stored and/or accessed and/or retrieved, regardless of the type of storage medium.

As shown in FIG. 1, the process can be directed to quality control of a sample along three parameters: A, B and C. It is though understood that the number of parameters can be less (e.g., two) or greater. At the start of the process, the system recognizes the palette that is inserted into the instrument, and pulls from the palette information about the product that needs to be analyzed. That is, the system can access the sample and the information on which parameters the sample needs to be assessed. For example, a recipe for analysis along parameters A, B and C is pulled up. The material is then transferred within the palette according to the recipe, and the analysis is conducted in a plate reader. The parameter C is assessed via a test, which yields a numerical value that is correlated to some sample property. If the value is within acceptable range, the sample is considered acceptable by parameter C. The parameters A and B are assessed similarly using a respective test, correlating some sample property to a numerical value. If the numerical value for each test falls within a predefined range, the sample is considered acceptable by both parameters, A and B. If the value of any of parameters A, B or C is outside of specified range, the sample is rejected.

It is also an embodiment of the inventive concept that disposable components can be identified and those components are discarded, or disposed of following the assessing of the sample (such as a radiopharmaceutical).

In one embodiment, a palette contains a receptacle configured to accept and retain a vial. This simplifies addition of an analyte sample to a palette with all the reagents already in it and eliminates the need to manually dispense the analyte (which can be radioactive). In other embodiments a receptacle for an analyte vial can be provided within a system in a location not associated with a palette.

In yet another embodiment the palette contains a plurality of wells with or without reagents and one or more receptacles where vials can be inserted. Such vials can be empty or filled. They can be capped or open and can contain reagents or analyte. It is possible to package a palette with all the reagents and an empty sealed vial (which can also be sterile). A user could then open this package shortly before the analytical application of the palette. The empty sealed vial can then be removed from the palette and placed within radiation shield where it would be filled with analyte sample. Then the vial can be placed back into the palette and the palette can be inserted into the system that uses it to analyze the sample. The sample can then be taken out of the vial and distributed to other locations within the palette by caddies. A vial can need to form a tight fit with the receptacle so that it does not fall out or cannot be accidentally pulled out of the palette by a caddy.

In another embodiment, the palette is designed in such a way that the insertion of a container (vial) triggers other events. An example of such an event can be breaking a well seal or mixing of reagents. In embodiments where the palette is installed in an instrument at the time of vial insertion, such insertion can trigger the start of the analytical process.

It should be noted that configuration of palettes to both permanently retain containers (e.g. wells) and removably retain containers (e.g. vials) is counter-intuitive. The prior art relies on either plates with wells or racks with vials but not combinations thereof.

In an analytical application that requires a plurality of reagents, not all the plurality of the reagents can be compatible with the same palette material. According to one embodiment of the inventive concept, a palette can have a plurality of regions and each of the regions can be made of different materials, each compatible with a set of reagents, to accommodate a diverse reagent set. The plurality of regions can be connected together through welding, gluing, one inserted into an opening or slot in the other, or any suitable connecting mechanisms. Other plates with reagents usually carry similar reagents which are all compatible with the material chosen for the specific plate. In one embodiment, a palette contains both organic and aqueous reagents. In another embodiment, the palette is made of a single material which is coated with a protective film (completely or partially) to protect the palette material from reagents which it is not compatible with.

In another embodiment a palette includes containers of different sizes and shapes. Size variability is dictated by the fact that different tests require different amounts of reagents. Whereas, shape differences can be necessary to optimize different detection methods used for different tests. Also, typically when multi-well plates are sealed, the seal covers the entire plate and seals all wells uniformly. In case of palettes, different locations can require different seals. Also some locations can be sealed while others are open. It is also possible to use a palette with standard/uniform well size but utilize inserts into wells that reduce the volume of different wells down to different final volume. Such inserts can be designed to hold a certain volume of liquid, solid, or gas or to displace a certain volume of liquid, solid, or gas.

In another embodiment, the palette can contain components that support chromatography or other separation-dependent analyses that are performed outside of the palette. For example, a palette can include a sample injection loop positioned to receive sample and for access by an external separation-based analyzer. Such a sample injection loop can be considered as one of the container, and in some embodiments can include a valve. In such embodiments its use would be the following. The sample loop is filled by a caddy with analyte while the palette is in one location. Then the palette is moved to another location where the loop ends up being in-line with the HPLC stream. This would allow the contents of the loop to be injected into a separation device that is external to the palette (for example an HPLC column, GC column, or electrophoretic system).

In another embodiment, a palette can include a septum-piercing device. Such a device can be used to pierce seals of individual locations (or containers) within a palette. It can also be used to add sealed vials to the palette in a way that deposits their contents into a location within the palette.

In another embodiment, a palette can have caddies packaged together with it or a palette can contain caddies. Such palettes can or can not contain reagents. The palette packaged with caddies (either within containers or next to them, either in 1:1 ratio or in other ratios) allows the analysis to be performed faster and for the user to control the cleanliness of the caddies to a greater extent.

In yet another embodiment, a palette includes hardware that plays a role in optical detection, for example a lens and/or waveguide. In another embodiment a light source or detection apparatus can be completely or partially contained within a palette. Such palettes can or can not be packaged with reagents. It is possible to use one type of palette to deliver the reagents and another type of palette to carry out the analysis.

In another embodiment, a palette can include a built-in mixer that effectively mixes liquids or a liquid and a solid. Such mixers can or can not be activated by one or more caddies. Such a mixer can be activated pneumatically, optically, magnetically, mechanically, thermally, and/or electrically.

In another embodiment, a palette designed for radioactive applications can include radiation shielding. Such shielding can serve to protect the user and/or to separate signals from different parts of the palette from one another to reduce noise in the measurements or "cross-talk". Such shielding can be permanently included in a palette or it can be removable. It is also possible that the shielding configured to protect a palette or part of it stays permanently mounted within the instrument while the palettes (standard or custom) can be inserted and removed without moving the shield. In other embodiments the system is designed such that cross-talk between radioactive signals from locations within the same palette is eliminated without using any shielding.

In some embodiments, palettes are designed in such a way that they can receive the sample of analyte without the use of an injection port, for example a sample can be added directly to a well or vial without using a port or tubing. The sample can also be delivered in a sealed vial. This is in contrast with prior art analytical systems, which require an injection port. It is also to be noted that any location within the palette can accept the analyte, whereas in traditional analytical instruments with ports there is only one specific location that can accept the sample injection.

In one embodiment, a palette is packaged with reagents that, when mixed with the analyte, produce measurable optical signals. In another embodiment, palettes are also designed to carry reference standards, which are known materials to which the analyte is to be compared. Such reference standards can be used to perform calibrations of various components of the system. They can also be used to perform daily system suitability testing. For example, a reference sample can be injected into an HPLC sub-system prior to the analyte, resulting in a chromatogram. This chromatogram is then evaluated to validate proper performance of the instrument prior to analyzing the real sample.

In one embodiment, there is a system of recognition between the instrument that operates palettes and caddies and the palette. The instrument can uniquely recognize the palette, for example through the use of unique indicia (for example a one dimensional bar code, 2 dimensional bar code, or RFID device) associated with the palette. Such a palette carries not only reagents but also information. This can be information about both the method that the specific palette is intended to use in its operation and information about the product/analyte being analyzed, date, user serial number and other sample-, method-, user- or facility-related information (or any other information).

As noted above, there can be a number of ways of carrying this information, while the palette is the carrier of both chemicals and information. The methods of carrying information include but are not limited to: (a) bar-code, (b) electronic media, optical signals and other information-carrying methods. Alternatively, such information can be encoded in the configuration of filled and empty wells, which can be used as a record of information that is interpreted by the instrument. The instrument can sense this information using an optical reader (for example, a microplate reader) or by caddy interaction. In such an embodiment the palette contains no extra features other than chemicals, but whether the chemicals are placed or absent in one or more given location can have a meaning that can be interpreted as information (e.g. regarding method, analyte, etc.).

Other configurations of a system can have separate palettes for liquid and solid reagents. Alternatively, these can be components of one palette. One part of the palette gets filled/sealed with solids in one process, while the other is filled/sealed with liquids in another process. Afterward these two (or more) components are combined to form one palette.

In some embodiments of the inventive concept, a method of using the palette to analyze sample is carried out such that some tests are performed immediately upon distribution of liquids/reagents while others are performed at a later time. During the time between liquid distribution and delayed reading, the palettes can be stored in a temperature and/or air controlled environment (e.g. an incubator).

Another method involves some of the tests to be performed on a palette within the instrument that distributes liquids while for other tests the palettes are sent to another facility which has different analytical equipment. In such embodiments the results of the remote analysis can be included in the complete report for a specific sample.

It should be appreciated that besides the enhancement of each individual test method described below, the palette technology uniquely enables further enhancements which include (but are not limited to): (a) multiple (replicated) readings for each test; and (b) replicated samples for each test, (c) reference standards, (d) calibration solutions for spectrophotometer, and (e) reference standards for HPLC, all pre-packaged on a palette. It is to be noted that methods according to embodiments of the inventive concept require no human judgment or subjectivity. The machine has a precise algorithm by which the sample is deemed acceptable or not even in borderline situations, which is not possible with subjective tests with human decision-makers.

A method of using a palette system for quality analysis according to one embodiment of the inventive concept is described in more detail below. Table 2 is a summary of the typical quality control tests for radiopharmaceuticals and the current existing method used. As shown in Table 2, all the tests use different test methods and require different devices and pieces of equipment in order to be carried out. Therefore, it is not possible to combine these tests in one system of the prior art. In contrast, by utilizing a suitable reagent that reacts with the radiopharmaceuticals and generate an optically detectable signal that can be correlated with one or more of the quality control parameters, embodiments of the inventive concept enable two or more of the quality control tests to be conducted utilizing a plate reader. A system according to one or more embodiments of the inventive concept allows a number of the quality control tests to be conducted simply utilizing one palette and one plate reader.

TABLE 2

| | Parameter | Current Test | Specification | Typical Result | Current Method |
|---|---|---|---|---|---|
| 1 | Color | Appearance test: color | visually colorless | visually colorless | Manual |
| 2 | Clarity | Appearance test: particulate | visually clear | visually clear | |
| 3 | pH | pH paper test | 5.0-7.5 | 6.4 | |
| 4 | Kryptofix 2.2.2 concentration | K222 Iodine vapor spot test | <50 μg/mL | <50 μg/mL | |

TABLE 2-continued

| Parameter | Current Test | Specification | Typical Result | Current Method |
|---|---|---|---|---|
| 5 Radionuclidic purity | Half-life measurement | 105-115 min | 108 min | |
| 6 Radioactivity concentration | Rad signal/volume ratio | 1-50 mCi/ml | 46.8 mCi/ml | |
| 7 Pyrogen concentration | Charles River endotoxin test | <22 EU/ml | <1 EU/ml | Endosafe reader |
| 8 Radiochemical Identity | HPLC % RSD of Standard | <10% | 1.70% | HPLC |
| 9 Radiochemical purity | Radio-HPLC AUC | >95% | 100% | |
| 10 Specific activity | HPLC UV/Rad AUC measurement | >0.4 Ci/µmol | 13.4 Ci/µmol | |
| 11 Organic solvents | GC analysis (% v/v) | EtOH: 4.0-10.0% Acetonitrile: <0.04% | 8.70% 0.00% | GC |
| 12 Sterility | 14-day post-injection culture test Sterile filter membrane integrity | no visible growth <40% | no visible growth 18% | Manual |

An example of conducting a quality control tests utilizing a palette-caddy system according to embodiments of the inventive concept is as follows.

Determination of the Radio-Pharmaceutical Sample as Being Either "Colored" or "Colorless"

Determination of the radio-pharmaceutical sample as being either "colored" or "colorless" can be accomplished according to embodiments of the inventive concept by filling one (or more) of test locations within a palette with diluted or undiluted sample of analyte and passing visible light through that test location, using a spectrophotometer or similar device to measure the absorbance of light by the sample at one or more wavelengths of visible or UV light (for example, light selected from the spectrum between 360 nm and 700 nm). In contrast, current colored/colorless determination is typically performed by visual inspection with a human eye. It has been determined experimentally that a human eye cannot detect color if a liquid sample with the thickness of 3 cm with optical density below about 0.01 AU/cm (absorption units) at any of the visible wavelengths is presented against a white background. Therefore if the sample does not absorb more than about 0.01 AU/cm at any wavelength it will be classified as colorless. Meanwhile, if absorption above 0.01 AU/cm is detected at any wavelength, the sample will be classified as colored and will fail the color test. Therefore the reliability of this method is better (e.g., superior) to current techniques. Unlike a human eye, this method yields a quantitative traceable result that has no variability between users. It is to be noted that while the assessment by human eye can detect the presence of color, it cannot quantify it. The method described here allows wavelengths and intensity of color absorption to be recorded. FIG. 13 shows UV-Vis absorbance versus wavelength for a set of three colored samples with various dilutions measured in a plate reader using a Synergy™ plate reader from BioTek™. As shown, the set of colored samples was diluted until no color could be detected by two observers. The samples were contained in a polystyrene (PS) flat bottom 96-well plate with 275 µl (microliters) of liquid in each well. Similar results were obtained using a PS flat bottom 384-well plate with 100 µl of samples in each well.

Determination of the Radio-Pharmaceutical Sample as being Either "Clear" or "Turbid".

Determination of the radio-pharmaceutical sample as being either "clear" or "turbid" is accomplished by filling one (or more) of the wells within a palette with a diluted or undiluted sample of analyte and passing visible light through that well, using a spectrophotometer to measure the absorbance of light by the sample at different wavelengths. These measurements are then compared to a series of turbidity standards with known concentrations of insoluble materials. It has been determined experimentally that a human eye cannot detect turbidity in a liquid sample below 0.1 AU (absorption units) at any of the visible wavelengths. Therefore if the sample does not absorb more than 0.1 AU at any wavelength it will be classified as clear. More to that, its absorbance measurement will be compared to standards with borderline concentrations of insoluble materials (just below and just above the threshold). All samples below the threshold will be classified as clear and pass the clarity test. While all samples with measurements above the threshold will fail the test. However, this test will provide more than pass/fail information. It will yield a measurement of insoluble materials and quantify it. This will allow the users to see trends in sample measurements and determine how close or far they are from the pass/fail threshold. Unlike a human eye, this method yields a quantitative traceable result that has no variability between users. It does not just distinguish clear samples from turbid, but provide a quantitative measurement of turbidity.

It should be appreciated that the tests for color and for turbidity (clarity) have similarities, but are distinct. For example, clarity and color can be determined at different wavelengths or sets of wavelengths. In some embodiments, clarity can be determined using the ratio between two different optical wavelengths (which provides a measure of light scatter), whereas color can be determined using a simple absorbance reading.

In some embodiments the color and clarity tests are combined. Traditional approaches to evaluation of liquid sample appearance rely on separate assessment of color and clarity. Color can be quantified via light absorption; clarity is normally detected via light scattering. These two measurements typically require two distinctly different optical schemes, one requiring detector in line with the light source (absorption) and another using detector at an angle to the light source (scattering).

Inventors of the present application found that the amount of light coming to the detector in line with the light source would be diminished in case of a clear, but scattering sample. In effect, an absorption measuring system will identify an apparent absorption in colorless but scattering liquid. Based on this observation it is possible to reject QC samples not conforming to the appearance standards, although this experiment alone will not determine whether color or clarity had failed.

Further investigation of the absorption spectra can determine if it is a result of absorption (color) or scatter (turbidity). The apparent absorption spectrum of a turbid liquid has a shape of exponential decay, while a colored sample spectrum inevitably has more features, corresponding to a preferentially absorbed wavelength(s). Simple fitting of absorption spectra with an exponential function will result in a good fit (chi$^2$~1) in the case of a scattering sample. In the case of a colored sample the fit will be poor (chi$^2$<<1, for example <0.5, <0.25, <0.1, or <0.05). A threshold for the fit quality can be determined (for example, >0.6, >0.7. >0.8, >0.9. or >0.95) to determine if the sample is only turbid, or it is also colored.

When the total absorption of light by a sample is measured across range wavelengths (for example, 300 nm to 700 nm), it is possible to set a threshold, for example, 0.10 AU, below which the sample can be considered both colorless and clear and one test can provide two results. FIG. 7 shows UV-Vis absorbance versus wavelength for a turbidity standard sample with various dilutions measured in a plate reader using Synergy™ plate reader from BioTek™. Here, the turbidity standards were diluted until solution was perceived as clear by two observers. The samples were contained in a PS flat bottom 96-well plate with 275 μl of liquid in each well. Similar results were obtained using a PS flat bottom 384-well plate with 100 μl of samples in each well.

Determination of the pH

Determination of the pH of the sample can be carried out by mixing the sample in one or more of the wells of a palette with a pH indicator such as (but not limited to) Methyl Red, although other pH indicators as appropriate for the desired pH range and detection system are also suitable. The acceptable pH range for a radiopharmaceutical sample is typically between 4.5 and 7.5. Typically, this is determined by manually spotting an uncontrolled amount of sample on a pH strip and comparing it to a reference visually. In an embodiment of the current inventive concept a volume of sample is mixed with a volume of indicator and the resulting color is measured on a palette, for example using a spectrophotometer, by passing light of an appropriate wavelength through the well and measuring absorbance. The intensity of the resulting absorbance, measured at a set (e.g., a specific) wavelength (e.g. 525 nm) is correlated with a precise pH of the sample. As in the other tests, this measurement is precise, subjective, traceable and user-independent. FIG. 8, left side (i.e. section A) shows normalized UV-Vis absorption versus pH value of a 200 μl sample with Methyl Red pH indicator; and FIG. 8, right side (i.e. section B) shows the pH value of a 200 μl sample with Methyl Red pH indicator (25 μl) versus normalized absorption at 520 nm. As shown in FIG. 8 section A, the normalized absorbance changes as the pH values changes from 2 to 9. As further shown in FIG. 8 section B, the pH value of a sample can be obtained based on the normalized absorption at 520 nm. A Spectramax™ reader from Molecular Devices™ was utilized and the samples were put in a PS flat bottom 96-well plate. Similar result was obtained using a Synergy™ plate reader from BioTek™ on a PS flat bottom 384-well plate with 5 μl indicator and 90 μl sample.

Transfer Catalyst Quantification

Transfer catalysts (i.e. phase transfer catalysts) are commonly used in the synthesis of radiopharmaceuticals. Transfer catalysts are typically quaternary ammonium salts, and include benzyltrimethylammonium chloride, benzyltriethylammonium chloride, methyltricaprylammonium chloride, methyltributylammonium chloride, and methyltrioctylammonium chloride. Kryptofix (2.2.2-cryptand)™ is often used as a phase transfer catalyst in the production of most fluorinated radiopharmaceuticals, including 18F-FDG. It is, however a toxic compound, and the FDA mandates testing of each batch for potential residual Kryptofix™. The upper QC limit is 50 mg/L, approx $1.3 \times 10^{-4}$ mol/L.

Current methods for Kryptofix™ quantification are poorly suited for automation. They typically rely on a reaction between Kryptofix™ absorbed on a solid support (TLC plate) and iodine vapor or other source of iodine. The method critically relies on a "revelation plate". A blue solid compound is formed and then an operator checks this color against positive and negative controls. As such, it is not possible to use such method for a solution-based measurement, for example, it is not possible to use the "indicator" (i.e., the blue solid compound) for a solution based measurement. The volume of samples is not controlled, the time or uniformity of iodine exposure is not controlled and the comparison is subjective. This method is difficult to automate due to the problems associated with measuring spectrum of reflected light, unstable color produced in the reaction and complex automation of the sample application to the solid support, unstable reading over time, confounding factors influencing spot intensity, and reflectance reading complicated by scattering and nature of support. Also, the current method is not really a method for determination of Kryptofix. Rather, it is a method for determination of tertiary amines with no selectivity to a particular amine.

An embodiment of the inventive concept uses a solution-based color test to circumvent the problems associated with the above referenced current method. The test is based on a competition for metal ion between Kryptofix™ and another chelator. If the competing chelator changes its spectral properties upon chelation, this will constitute the basis of analysis. The ratio between the free chelator and chelator-metal complex will define the absorption spectra of the solution. In the presence of Kryptofix™, metal ions will partially bind to Kryptofix™ increasing relative concentration of the free indicator. This will produce spectral shift detectable by the plate reader in the absorbance mode.

Kryptofix™ is known to bind three different types of metals, including Aluminium, Barium, Beryllium, Bismuth, Cadmium, Calcium, Cerium, Cesium, Chromium, Cobalt, Copper, Dysprosium, Erbium, Europium, Gadolinium, Gallium, Gold, Hafnium, Holmium, Indium, Iridium, Iron, Lanthanum, Lead, Lithium, Lutetium, Magnesium, Manganese, Mercury, Molybdenum, Neodymium, Nickel, Niobium, Osmium, Palladium, Platinum, Potassium, Praseodymium, Rhenium, Rhodium, Rubidium, Ruthenium, Samarium, Scandium, Silver, Sodium, Strontium, Tantalum, Technetium, Terbium, Thallium, Thulium, Tin, Titanium, Tungsten, Uranium, Vanadium, Ytterbium, Yttrium, Zinc, and Zirconium in any oxidative state to form complexes. In embodiments of the inventive concept such complexes can be detected colorimetrically, for example with the aide of an indicator. Such an indicator can, for example, provide a color or fluorescence emission indicative of the presence of a free metal ion that is subsequently lost on the formation of a complex of the metal ion with a phase catalyst.

Kryptofix™ was specifically designed to bind potassium preferentially over other alkali metals. One embodiment of the inventive concept utilizes this feature to provide a Kryptofix™ detection system that includes eriochrome black T, a color indicator for potassium, and potassium chloride. The analysis can be performed, for example, in a mixture of water with organic solvent such as ethanol or DMF, to stabilize eriochrome T in the solution.

In another embodiment, Xylenol orange can be used in combination with Ba and/or Sr cations. An added enhancement of this approach would be the absence of these cations in the original QC sample. An alternative approach might be using fluorescent indicators for Ca, such as FLURA-2 or INDO-1. This can require the use of fluorescent measurement, a common feature of the plate readers equipped with luminescent detector. Ca-fluorescent approach would offer a high (an extremely high) sensitivity and low background.

In an embodiment of the inventive concept, a set or specific amount of sample is mixed with a set or specific amount of metal salt and the respective metal indicator and the resulting color is measured on a palette by a spectrophotometer with light passing through the well and the absorbance being measured. The intensity of the resulting absorbance, measured at a set or specific wavelength (e.g. 540 nm) is correlated with a precise Kryptofix™ concentration in the sample. As in the other tests, this measurement is precise, objective, traceable and user-independent. It has been validated experimentally and demonstrated reproducible results in the range of Kryptofix™ concentrations between 0 and 5000 mg/L. The method is capable of determining exact concentration of Kryptofix™ and perform pass/fail assessments in the borderline cases with concentrations very close to 50 mg/L. FIG. 9 shows UV-Vis absorbance versus wavelength for various concentrations of Kryptofix™. In FIG. 9, series of absorption spectra of (Ba2+/Xylenol orange) mixture in the presence of various concentrations of Kryptofix™, from 0 mg/ml to 1000 mg/ml were shown. As the concentration of Kryptofix™ increases, the absorbance (vertical axis) at 425 nm decreases, while the absorbance at 575 nm increases. The absorbance at 475 nm is an isosbestic point. It can be observed that Kryptofix™ concentration is proportionate to absorption at 575 nm, when normalized by the absorption at 475. A Spectromax™ reader from Molecular Devices™ was used and the samples were held in a PS flat bottom 384-well plate with 12 µl indicator and 100 µl sample in each well.

Suitable metal ions can include, but not limited to, Li+ (lithium), Na+ (sodium), K+ (potassium), Rb+ (rubidium), Cs+ (cesium), Ag+ (silver), Mg2+ (magnesium), Ca2+ (calcium), Sr2+ (strontium), Ba2+ (barium), Zn2+ (zinc), Cd2+ (cadmium), Al3+ (aluminum), Bi3+ (bismuth), Cr2+ (chromium(II)), Cr3+ (chromium(III)), Co2+ (cobalt(II)), Co3+ (cobalt(III)), Cu+ (copper(I)), Cu2+ (copper(II)), Fe2+ (iron(II)), Fe3+ (iron(III)), Pb2+ (lead(II)), Pb4+ (lead(IV)), Mn2+ (manganese(II)), Mn3+ (manganese(III)), Mn4+ (manganese(IV)), Hg+ (mercury(I)), Hg2+ (mercury(II)), Sn2+ (tin(II)) and Sn4+ (tin(IV)).

Suitable indicators can include, but not limited to, Arsenazo III, 1H-Benzotriazole, Bismuthiol I, Calcein, Cal-concarboxylic acid, Calmagite, Chromeazurol S, o-Cresolphthalein Complexone, Diamine green B, 3,3'-Dimethylnaphthidine, 2,9-Dimethyl-5-picrylamino-o-phenanthroline, 1,5-Diphenylcarbazide, Diphenylcarbazone, Dithizone puriss, Eriochrome® Black T, Eriochrome® Cyanine, Glycine Cresol Red, Glyoxal-bis(2-hydroxyanil), Hematoxylin, Hydroxynaphthol blue, 3-Hydroxy-4-nitroso-2,7-naphthalenedisulfonic acid disodium salt, 3-(3-Hydroxy-4-nitroso-N-propylanilino)propanesulfonic acid, 2-Mercaptobenzothiazole, Methylthymol Blue, Morin hydrate, Murexide, Naphthol Green B, 4-Nitroaniline, 4-(4-Nitrophenylazo)-1-naphthol, N-Phenylanthranilic acid, N-Phenyl-α-(4-nitrophenyl)nitrone, Purpurin, 1-(2-Pyridylazo)-2-naphthol, 4-(2-Pyridylazo)resorcinol, Pyrocatechol Violet, Pyrogallol Red, 8-Quinolinol, Sodium rhodizonate, Thorin, Thymolphthalexon, Tiron, o-Tolidine, Xylenol Orange tetrasodium salt, Xylidyl blue I, and Zincon monosodium.

Pyrogens

Pyrogens are byproducts of bacterial activity that can cause a fever in humans or other mammals. It should be understood that pyrogens can be present in a sample that has no live bacteria and cannot be detected by sterility tests. Pyrogenicity is a measure of the presence/concentration of pyrogens in a sample. There are 2 main existing methods for determining it, both relying on a reaction of an enzyme (LAL) with a pyrogen, yielding a visible change in the sample. The acceptance criteria for the pyrogen test are that the entire dose administered to a patient has less than 175 Endotoxin units (EU). The acceptance criteria for a batch of product depend on the size of the batch and volume of each dose. One conventional method relies on a visual signal in a test tube assessed by human eye. Another conventional method relies on an assessment done in a microfluidic chip with a spectrophotometer (for example, a PTS reader). The method according to embodiments of the inventive concept is different from both. As the rest of the methods described herein, it is performed on a palette. An analyte sample is mixed with the LAL reagents in a well of a palette and the resulting color or rate of color change is detected by a spectrophotometer. The difference of the method according to embodiments of the inventive concept from microfluidic method is that the latter requires a microfluidic chip and relies on motion of liquids through channels in the chip while the method according to embodiments of the inventive concept relies on a well in a test palette (for example, a well of a microwell plate) and does not require liquids flowing through the palette. Another distinction is that a microfluidic chip is specific for endotoxin testing while a palette in the method according to embodiments of the inventive concept contains one or more other tests in addition to endotoxin. The latter is an enhancement since current approaches have been unable to combine an endotoxin test with other tests. One reason is because all channels have been eliminated in a palette system and it does not require liquid flow. If liquids flow through channels to get to the endotoxin testing site, one would have to assure absence of endotoxins in all channels upstream of the test site, which is not practical.

In addition, use of the LAL testing reagent can require temperatures that differ from ambient temperature (typically being elevated) and constancy of temperature throughout a majority of the performance of the test. As a result, simply adding an LAL reagent to a well of a typical microwell plate and placing the plate in an incubator does not yield satisfactory results, due at least in part to the relatively slow temperature equilibration of the microwell plate. In some embodiments of the inventive concept, a pyrogen test is performed in a region of the test palette that has a low thermal mass and that is thermally isolated from the remainder of the test palette. On introduction into an environment with a different temperature such a low thermal mass test well rapidly comes to thermal equilibrium with the environment and can provide a suitably stable temperature for performance of a pyrogen test.

Figure 10:
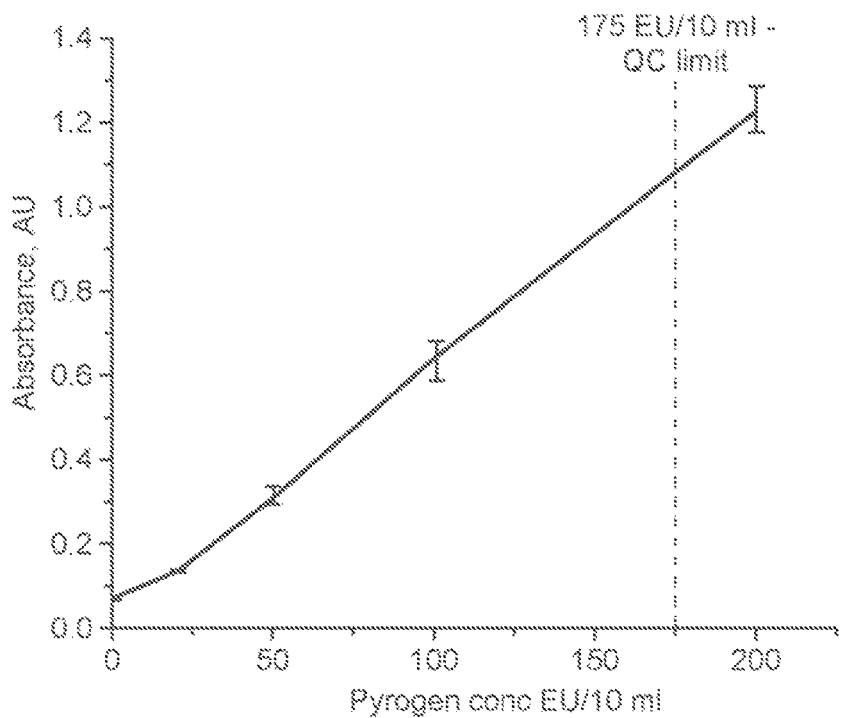
FIG. 10 illustrates a typical change of UV-Vis absorbance versus pyrogen concentration.

The method according to embodiments of the inventive concept of pyrogenicity assessment has been validated in the range of 0-200 EU/microliter. FIG. 10 shows the change of UV-Vis absorbance versus pyrogen concentration using a Synergy™ plate reader from BioTek™. The samples were held in a PS flat bottom 96-well plate with 50 µl sample and 200 µl other reagents.

Radionuclidic Purity

Two QC parameters require quantification of the radioactive isotope in the sample: radioactivity concentration and radionuclidic purity. Radioactivity concentration can be calculated from the radiation intensity measured for a sample aliquot. Radionuclidic purity is typically established via measurement of apparent half-life, calculated from two consecutive measurements of the radiation intensity in the same sample. Due to the inherently high variability of determination of exponent lifetime based on just two close data points, QC limits for this parameter are typically set widely: 105-115 min in case of $^{18}$F ($t_{1/2}$=109.7 min).

The common approach is measurement of the half-life of radioactive decay of the sample and comparison to the known half-life of the desired radio-isotope. The common way of calculating half-life is by measuring the level of radiation emitted by the same sample at two (or more) points in time and correlating the change with the rate of decay. Current standard practice has a person performing two measurements 10 minutes apart using a dose-calibrator and then calculating half-life manually.

Figure 18:
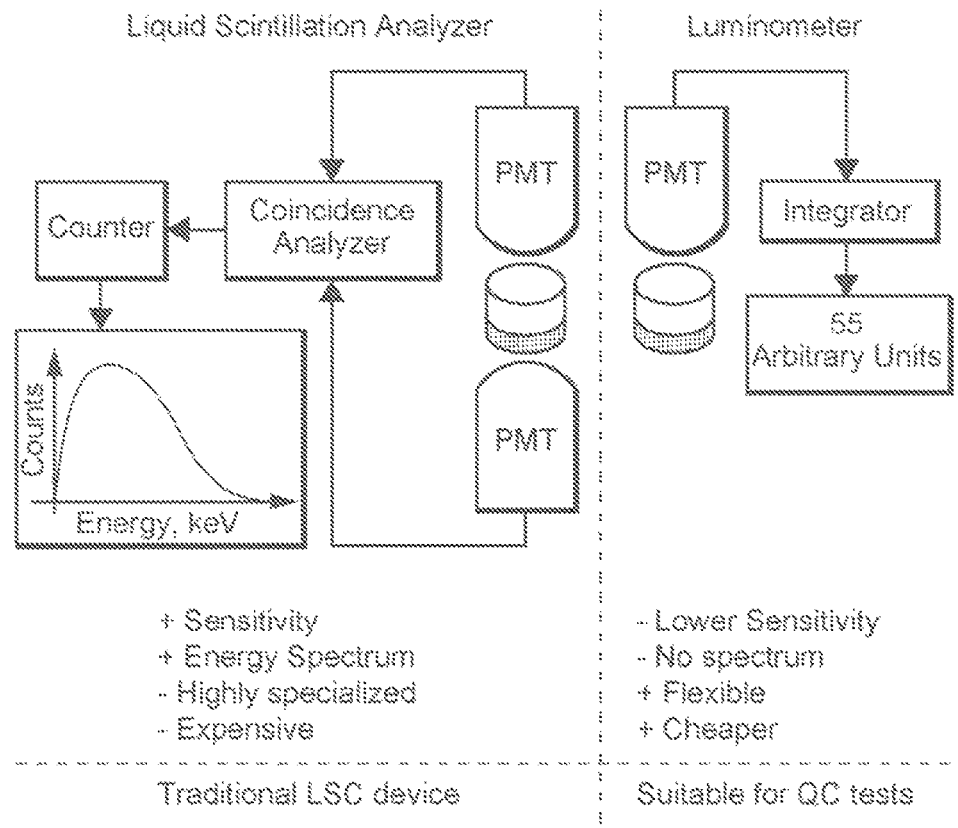
FIG. 18 shows a comparison between a traditional liquid scintillation counting (LSC) device and a QC test utilizing a luminometer according to an embodiment of the inventive concept.

By definition, positron emitting isotopes produce positrons during the decay. One embodiment of a method of the inventive concept utilizes scintillating liquid to convert the energy of the emitted positron to light detectable by a luminometer (for example, a plate reader with a luminescence mode). Typically, a specialized instrument called Liquid Scintillation Analyzer (LSA) is used to determine the intensity of radiation associated with positron emitting isotopes. FIG. 18 shows a comparison between a traditional Liquid Scintillation Counting (LSC) device and a QC test utilizing a luminometer according to one embodiment of the inventive concept. As shown in FIG. 18, an LSA is a complex instrument designed to detect faint scintillations originating from weak beta emitters such a $^3$H (0.018 MeV). To discriminate true nuclear events from background noise, these instruments have two light detectors working in sync or one detector. As a result an LSA is a highly specialized instrument not capable of other measurements required for QC of radiopharmaceuticals.

Luminometers, or plate readers with luminescence reading capability, are typically equipped with only one light detector, operating in the integral mode. As opposed to LSA, measuring individual bursts of light, these machines continuously measure light coming out of the sample. According to one or more embodiments of the inventive concept, a plate reader in luminescence mode is utilized to detect the light originating from the sample. The high energy of positrons originating from $^{18}$F and high activity typically used for medical imaging result in strong signal. Therefore, extreme sensitivity of LSA is not needed for QC of radiopharmaceuticals.

According to one embodiment of the inventive concept, positron emitting isotopes can be quantified by liquid scintillating counting using specialized counters. The levels of activity typical for QC samples of FDG (5 mCi/ml in one embodiment) provide a very strong signal. Conventional plate readers lack the high sensitivity and spectral resolution of specialized instruments, however the high intensity of the signal associated with typical QC samples allows for a sufficient signal-to-noise ratio to provide suitable results. One or more radiation measurements on positron-emitting radionuclides (required for different parameters) can be achieved by luminescence measurement of the total light output from a location where a radioactive sample is interacting with a scintillating reagent. This measurement is precise, does not rely on subjective timing or the position of a sample within a dose calibrator. Also, this method allows collection of a continuous reading of the light emission, which means a precise signature of the decay rather than sampling it at only two data points. The half-life is also calculated automatically based on the decay monitoring.

Examples of radio-isotopes that can be analyzed according to embodiments of the inventive concept include, but not limited to $^{18}$F, $^{11}$C, $^{13}$N, $^{82}$Rb, $^{15}$O, $^{99}$Tc, $^{123}$I, $^{131}$I, $^{111}$In, and $^{68}$Ga. Table 3 summarizes the measurement result of the half-life of sample FDG. In the measurement, 100 µl of sample FDG dose were mixed with 200 µl of scintillating liquid. The first measurement was taken at time=0, and the second measurement was taken at time=9.2 minutes. A Synergy™ plate reader from BioTek™ was used in luminescence mode. The samples were held in a PS flat bottom 384-well plate.

TABLE 3

| Sample # | I (t − 0) | I (t − 9.2) | $T_{1/2}$, min |
| --- | --- | --- | --- |
| 1 | 7830 | 7402 | 113 |
| 2 | 8039 | 7582 | 108 |
| 3 | 7744 | 7290 | 105 |
| 4 | 7139 | 6732 | 108 |

In other embodiments of the inventive concept, the inventors have surprisingly found that Cherenkov radiation resulting from positron emission can be detected directly from such samples. Such Cherenkov radiation can be detected, for example, using a luminometer or other suitable optics suitable for detection of low intensity light. Since Cherenkov radiation is directly detectable, such methods can advantageously be performed in the absence of a scintillant or scintillating material. In addition, the high degree of localization provided by Cherenkov radiation effectively prevents cross talk between adjacent test sites used for characterizing radioactive samples, even when such sites are closely spaced and in the absence of specialized shielding.

Radioactivity Concentration

Figure 11:
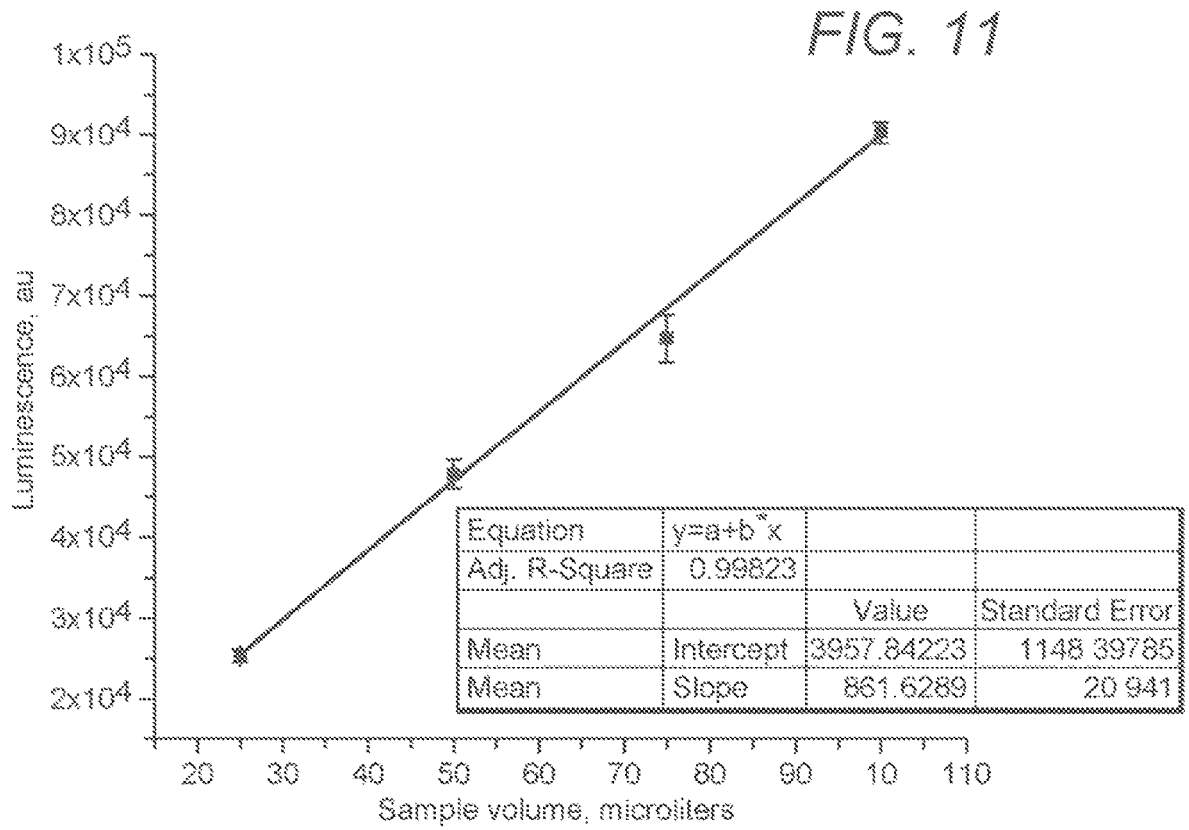
FIG. 11 shows the luminescence of a sample observed as a measure of radioactivity in that a sample, where the optical signal is a result of the response of the scintillating liquid to radioactive material).

Radioactivity concentration is a measure of the amount of radiation (or radioactive material) per unit volume. The radiation measurement is performed in a fashion similar to that of the half-life assessment, however readings are correlated with the volume of the sample rather than change over time. FIG. 11 shows the luminescence of a sample versus the sample volume, where the luminescence intensity roughly depends on the radioactivity concentration in a linear relationship. Here, the samples were contained in a PS flat bottom plate with 384-wells and analyzed utilizing Synergy™ plate reader from BioTek™. Table 4 is a summary of radioactivity concentration measured on a 384-well plate, where radioactive samples were placed in wells that are shaded and the rest of the wells were left empty. One batch of radioactive material was used for the whole experiment while different amounts of it were mixed with the scintillating liquid as indicated by the ratios on the left side of the first column. Wells of the same shade have the same amount of radioactive material. Wells of different shades differ in the ratio of the amount of radioactive material with the amount of the scintillating liquid. The numbers in the wells represent the luminescence readings. As can observed from Table 4, the readings from the filled wells are 3 orders of magnitude higher than readings from the adjacent wells, confirming that no cross-talk between wells and no interference between different radioactive samples even in the absence of any radiation shielding.

TABLE 4

| Sample | | | | | | | | | | | | | | | | | | |
|---|---|---|---|---|---|---|---|---|---|---|---|---|---|---|---|---|---|---|
| 100 MKL Sample + 900 mkl ScintLiq | E | 89672 | 136 | 27 | 188 | 92568 | 123 | 23 | 143 | 88993 | 122 | 18 | 141 | 90574 | 130 | 21 | 121 | 90759 |
| | F | 130 | 45 | 15 | 42 | 135 | 45 | 16 | 46 | 130 | 45 | 12 | 39 | 152 | 45 | 17 | 43 | 152 |
| | G | 17 | 16 | 13 | 16 | 16 | 20 | 14 | 35 | 16 | 13 | 21 | 11 | 16 | 13 | 10 | 10 | 18 |
| | H | 71 | 30 | 14 | 39 | 99 | 46 | 17 | 36 | 94 | 31 | 13 | 42 | 103 | 49 | 11 | 28 | 84 |
| 75 mkl Sample + 925 mkl ScintLiq | I | 60029 | 69 | 16 | 100 | 66541 | 93 | 17 | 117 | 65807 | 85 | 17 | 110 | 67069 | 94 | 23 | 104 | 64603 |
| | J | 85 | 24 | 15 | 45 | 107 | 42 | 22 | 29 | 114 | 40 | 15 | 40 | 122 | 41 | 13 | 34 | 114 |
| | K | 14 | 10 | 11 | 15 | 15 | 17 | 11 | 21 | 12 | 19 | 8 | 12 | 11 | 10 | 10 | 9 | 13 |
| | L | 55 | 24 | 14 | 31 | 66 | 23 | 10 | 39 | 55 | 26 | 13 | 27 | 81 | 34 | 14 | 24 | 75 |
| 50 mkl Sample + 950 mkl ScintLiq | M | 45029 | 59 | 13 | 70 | 49138 | 73 | 23 | 73 | 47779 | 64 | 28 | 74 | 49541 | 74 | 17 | 79 | 486462 |
| | N | 79 | 22 | 13 | 26 | 87 | 28 | 16 | 29 | 99 | 25 | 8 | 24 | 99 | 24 | 11 | 30 | 89 |
| | O | 38 | 12 | 12 | 15 | 37 | 20 | 11 | 21 | 42 | 22 | 12 | 19 | 61 | 18 | 19 | 19 | 47 |
| 25 mkl Sample + 925 mkl ScintLiq | P | 24268 | 40 | 8 | 54 | 25129 | 30 | 9 | 45 | 25958 | 49 | 11 | 55 | 26071 | 43 | 14 | 46 | 25943 |

In other embodiments of the inventive concept, the inventors have surprisingly found that Cherenkov radiation resulting from positron emission can be detected directly from such samples. Such Cherenkov radiation can be detected, for example, using a luminometer or other suitable optics suitable for detection of low intensity light. Since Cherenkov radiation is directly detectable, such methods can advantageously be performed in the absence of a scintillant or scintillating material. In addition, the high degree of localization provided by Cherenkov radiation effectively prevents cross talk between adjacent test sites used for characterizing radioactive samples, even when such sites are closely spaced and in the absence of specialized shielding.

Organic Solvents

It is important to measure the concentration of organic solvents in the sample because they are toxic (above a certain concentration). Organic solvents such as acetonitrile (MeCN) can originate from the synthesis procedures. Meanwhile, ethanol (EtOH) is used to formulate the sample for injection, but it too cannot exceed a certain limit. Traditionally concentrations of these solvents are measured with a gas chromatograph (GC) which is an expensive multi-purpose instrument requiring sophisticated maintenance and extreme precision of sample injection (which is frequently done manually). A method according to an embodiment of the inventive concept eliminates the need for GC and can rely on one of several options, which are described below.

Option 1—spectrophotometric detection with an indicator. A suitable indicators can react with each specific organic solvent (starting with MeCN and EtOH) and result in an optically-detectable change that can be correlated with the concentration of that specific solvent in the sample being tested. In one embodiment a set or specific amount of sample is mixed with a set or specific amount of indicator and the resulting color is measured on a palette by a spectrophotometer with light passing through the well and the absorbance being measured. The intensity of the resulting absorbance, measured at a set or specific wavelength is correlated with a (precise) solvent concentration in the sample. As in the other tests, this measurement is precise, objective, traceable and user-independent.

Option 2—HPLC. A method according to another embodiment of the inventive concept relies on separating solvents on an HPLC column and detecting them upon exit from the column using a refractive index detector. Each solvent will have a known retention time and the Analytical Ultracentrifugation (AUC) in a chromatogram can be correlated with the concentration of that specific solvent. This method relying on palette and caddies allows high precision of injection volume and time while eliminating any need for manual handling or analysis of results. A caddy picks up a known volume of sample from a palette and injects it into HPLC, simultaneously triggering the start of a chromatogram. FIG. 12(A) shows the result measured using a Refractive Index detector versus the concentration of ethanol and acetonitrile; and FIG. 12(B) shows an HPLC chromatograph versus retention time for ethanol and acetonitrile. As can be observed in FIG. 12(A), the result of the RI detector has excellent sensitivity and linearity over the entire range of concentrations tested. As can be observed in FIG. 12(B), the polymeric columns using Hamilton PRP-1 and DI water as the mobile phase have excellent separation efficiency over the entire range of concentrations.

Option 3—Colorimetric Detection. For colorimetric detection, the organic solvent (for example, acetonitrile) is reacted with an amine (for example, ammonia, hydroxylamine, ethanolamine, etc.) to produce a product that absorbs visible and/or UV light. Alternatively, the reaction product of such a reaction can be mixed with a metal complex to either generate a visible or UV light absorbing modified complex or to alter the UV or visible light absorbing characteristics of the metal complex.

Determining Radiochemical Purity, Chemical Purity, and Radiochemical Identity

Radiochemical and chemical purity and radiochemical identity are measures of contamination of the radioactively-labeled product by radioactive and non-radioactive contaminants and confirmation that the main product is indeed the desired product, for example by comparison to a non-radioactive standard. Traditionally these are performed in combination by TLC or HPLC. The conventional method requires daily preparation of standards that cannot be stored in solution and require extreme precision, which is difficult to achieve manually with small sample size. Then multiple standards are injected and multiple chromatograms are acquired and analyzed by a person.

In some methods according to embodiments of the inventive concept this assessment is performed using HPLC with UV-Vis and radiation detectors. While the chromatography component is similar to current methods, the infrastructure around it is different. First, the injection in the method according to embodiments of the inventive concept is automated and delivers precise volume of sample picked up by a caddy from the palette and injected at a precise time concurrently or simultaneously triggering the start of a chromatogram. Also this method allows for the inclusion of the results of this test in the complete over-arching report on all QC parameters. In all current methods HPLC is run independently of all other tests. In addition, the difference and benefit is in the daily system suitability testing and calibration. Traditionally, the latter processes require preparation of multiple standard samples followed by their individual injections into HPLC, generation of multiple chromatograms and their analysis (with a lot of manual handling). The method according to embodiments of the inventive concept allows all standards and reference samples to be pre-packaged on a palette in precise amounts, which are stored dry as powders. Solvents can be stored in different locations on a palette. As the process starts, the solutions can be made automatically with high precision using caddies and injected automatically. For example, an automatic injector can take samples directly from a palette. Or a caddy can be utilized to transfer samples from the palette to the HPLC injection port. Further, the method according to embodiments of the inventive concept allows chromatographic programs and analysis algorithms to be programmed into the instrument. So all the user has to do is to insert the palette and start the program. The instrument will then execute a sequence of calibrating/suitability chromatograms, analyze their respective reports and signal that system is ready for the injection of the analyte sample without any user interaction (which now requires hours of work every day and has very poor traceability or reference standard amounts, concentrations, injection times and other data in the conventional method).

In alternative embodiments of the inventive concept separation of sample components is performed on the palette. In such embodiments the palette incorporates a separation device. For example, a bed of chromatographic stationary phase can be deposited within a palette having a substantial length. This can be a TLC plate coated with mobile phase or a small column packed with a stationary phase. The sample is delivered to one end of the plate/column and moves to the other end driven by a flow of solvent. In case of TLC or use of a small column solvent can move via absorption and/or capillary forces. For example, in embodiments employing a small column or capillary the solvent can impelled by pressure, vacuum, capillary action, or centripetal force (e.g. induced by rotation of the palette). Once the first components of the sample have travelled the full length of the stationary phase, an assessment is performed on the components of the mixture separated along the stationary phase based on their affinity for the latter. Alternatively, movement of sample components along the separation device can be followed in real time. The assessment can be performed by shining UV light onto the stationary phase and measuring its absorption on different locations (indicative of the type and amount of material deposited at that location and yielding a chromatogram), observation of fluorescence or phosphorescence, or observation of Cherenkov radiation. This chromatogram can, for example, be obtained on a plate reader. It can be digital (for example, reading at positions corresponding to individual wells of a microwell plate as they would be positioned near the chromatographic bed) or continuous (for example, with measurements obtained at all locations using an imaging system). Similar approach can be taken for the radioactive trace with scintillating liquid deposited underneath or in close proximity to the stationary phase such that the radioactive emission from the various radioactive components deposited on the stationary phase triggers signals from the scintillating liquid at the corresponding locations. It is to be noted that such assessment is not reflective of a single point being monitored upon separation of mobile phase from solid phase. Instead it allows to observe live separation on the solid phase while it is in progress.

Yet another embodiment requires no chromatographic separation for the assessment of chemical purity. It requires a known absorbance spectrum of the 100% pure product as a reference. Such spectrum can be obtained on a plate reader from a single well/position within a palette without moving the sample or separating it on stationary phase. For example this can be a UV absorbance spectrum, with absorbance measured at each wavelength of the spectrum. Once this complex pattern is obtained for a product with 100% purity, the spectra obtained from analyte absorption measurements within the same spectrum can be compared to this reference. If the difference between the standard and analyte absorption spectra reaches a certain percentage at any one wavelength, the analyte can be classified as impure. However, if the analyte spectrum falls within pre-defined error bars around the standard spectrum, the analyte will be considered to be of acceptable purity. The width of error bars should be determined experimentally for each product. The width of error bars can be uniform or can vary between different wavelengths. The absorbance spectrum can be measured within any range of detectable wavelengths. Visible, UV, and IR ranges are just examples and are not meant to limit the application of this invention.

In some cases, the analyte can have poor absorbance in all ranges of the spectrum. In such a situation, the analyte can be combined with a reagent that enhances its signal and allows to quantify the amount/concentration of the analyte.

A method according to another embodiment of the inventive concept utilizes palette-based method to assess radiochemical purity. Typically small radioactive contaminants have no absorption in any spectral ranges (they are below the detection limit). Thus to determine the presence of radioactive impurities that have no optical signal, one can either rely on a separation-based method as described above or filter an analyte sample through a portion of stationary phase that is designed to trap either the impurities or the desired product. By comparing the radioactivity measurement in the portion of stationary phase to that of the treated liquid, one can assess the ratio of desired product to impurities. Alternatively, specific activity can also be assessed using an absorption spectrum from a single test site and comparing it to the radioactive measurement from a single test site. This allows specific activity determination without any chromatographic methods.

Sterility

Sterility testing is the confirmation of the absence of any living organisms (e.g. fungi, yeast, bacteria) in the sample. However, such tests do not yield a result within a time-frame compatible with the decay of the radionuclides used in PET. A typical sterility test involves providing a culture in which bacteria can grow and replicate to the point when colonies become visible—a process that takes 14 days. Meanwhile a typical radionuclide used in PET ($^{18}$F) has a half-life of 110 minutes and $^{18}$F-labeled products have a maximum shelf-life of 6 hours. Therefore the currently acceptable test relies on having the results of 14-day sterility test after the product has been administered to patients and assuring sterility on the front end by passing the entire volume of product through a sterilizing filter, followed by confirmation that the filter is intact following the filtration procedure. There are really 2 tests required for sterility (1) 14-day culture test with post-injection results and (2) pre-injection filter integrity test. A method according to embodiments of the inventive concept offers 2 options for sterility assessment:

A traditional culture test can be performed with a palette system, and requires a smaller volume of reagents, and provides both a shorter time for culture development and an exact measure of bacterial activity (versus presence/absence confirmation). In an embodiment of the inventive concept a set or specific amount of sample is mixed with a set or specific amount of growth culture and placed into an incubator (e.g. at 37° C.). Periodically, the palette containing mixed sample and culture is taken out of the incubator and assessed optically in a plate reader (spectrophotometer) to monitor changes in the optical properties of the wells of interest. This method allows detection of bacterial colonies at a much smaller size (and therefore earlier time point) than current method relying on visual assessment by human eye after 14 days. It also allows measurement of the density of colonies and their growth rate. The results are available earlier than 14 days, human interaction and error is reduced or eliminated and measurements are quantitative. In embodiments where this data is available after administration of product to patients the filter test will still be required. For the latter, a sub-system of the synthesis/analysis system will be placed inside the radiation shielding where the filter is located. The filter will be connected to a pressure line and the instrument will monitor a pressure drop across the filter which can be correlated with its integrity. The way this method differs from the current manual assessment is that it allows to measure (measure exactly) what pressure the filter can hold and how close it can be to break-through point. Traditional methods relies on a visual assessment and do not yield a quantitative result.

Alternatively, an instantaneous assessment of sterility can be performed in a palette using a spectrophotometer. This method does not rely on the growth of colonies and therefore does not require the time necessary for such growth. It allows detection of live cells (with a limit of detection being 1 cell) in a sample. It relies on reagents that react with cell membranes yielding an optically detectable signal allowing to quantify the number of live cells present in the sample. Since the results of this test will be available prior to administering products to patients, the need for the filter test will be eliminated. The intensity of signal arising from the well is proportional to the number of live cells in that well (and the speed of the test does not rely on the speed of formation of bacterial colonies). Alternatively, such a method can utilize UV irradiation of a sample in a test site of a palette accompanied by detection of autofluorescnce associated with protein components of living cells.

In another embodiment of the inventive concept, a rapid test is performed within the palette requiring no reactions but instead relying on a solvent or buffer flow. In such an embodiment the palette is provided with a flow channel between two wells and a pair of electrodes placed across the flow channel. The diameter of the channel is comparable in scale to the size of live bacterial, yeast, and/or fungal cells, or includes a membrane or other separator having an aperture of comparable diameter. The electrodes measuring resistance (or any other signal) across the channel (or, alternatively, across the aperture) to produce different signals in the presence of pure solution versus having a cell (pass) between these electrodes (or through the aperture). Once the entire sample volume is passed through this channel from one well to the other, the number of spikes (or signal changes) detected by the electrode corresponds to the number of live cells in the sample. In order to make this method fast and practical, a number of channels can connect the two wells instead of one with electrodes on each channel. This way a volume of the sample that is on a much larger scale than the cross section of a channel can be processed within a short time period. The number of channels can range from 1 to several million, limited only by the maximum channel density allowed by manufacturing techniques.

In another embodiment, a combination of the two above methods can be used to determine sterility. One or more channels connect two locations fluidically. Each channel has a physical trap for living cells at a specific location. The trap can be a filter or a constriction in the channel. In case of a filter, once the cell is trapped, the liquid keeps flowing around it. In case of a constriction once the cell is trapped, the channel is plugged and the flow stops. These traps can be used to detect live cells by different means. In one embodiment the cells are labeled with materials that bind to their membranes and produce optical signals. These signals can be detected by a spectrophotometer monitoring a specific location (or locations in the embodiment with multiple channels). The enhancement of this method over the one with cells in a well is that the cells become immobilized, which allows attenuation of the optical signal.

In another embodiment, the test palette includes a plurality of channels (having a diameter similar to that of the cells to be detected) through which the sample is passed. Flow is measured in all channels. The channels that have cells trapped in them will have reduced flow. Thus the change in flow in a given channel or the number of channels with reduced flow can be correlated with the number of live cells in the initial analyte sample. Constrictions and filters are only examples of cell traps. Other embodiments are possible. It is also possible to carry out this method without a trap. If the optical detector placed above the channel is sensitive enough to recognize moving cells, than the trap is not necessary.

It is to be noted that cell trapping and analysis described above can be achieved with an unencumbered flow path (e.g. one having no valves). It is also to be noted that certain embodiments of the above invention can operate with forced flow while others without forced flow. It is also possible to realize this invention with or without palettes and caddies. In one embodiment of the inventive concept, the sterility-testing system according to embodiments of the inventive concept is packaged as a stand-alone device not including any other tests described above. Such device can or can not have disposable components.

In another embodiment the sterility measurement based on detection of individual cells assures such detection by labeling live cells with radioactive markers, which are much easier to detect than optical signals.

In another embodiment the liquid can be pulled through channels by a vacuum. In yet another embodiment the liquid can be pushed into a channel towards the end of the channel or another reservoir that is closed by a gas-permeable liquid-impermeable membrane. It is also possible to assemble such a device from materials that have hydrophilic surfaces that pull the aqueous sample from the source to the sink without any extra motive force. It is possible to have the liquid move by capillary force.

In another embodiment it is possible to use the above methods for sterility detection not only to detect and quantify all live cells, but to distinguish between the types of cells (For example, detecting bacteria in whole blood and/or differentiating between different blood cell types.)

In a live-cell-detection embodiment as described above the number of sources and sinks is not limited. It can be 1:1 or 1 to many or many to 1. The source can have the same volume as the combined volume of all channels. Thus the channels themselves become the sink. The source can be a container in the center of a device with channels radiating like wheel spokes away from it, while the sink is a tube along the circumference where all the spoke channels lead to. These are just examples and can other embodiments can be either possible or more practical.

In some embodiments, sterility can be determined for an entire produced volume of radiopharmaceutical (or other product of chemical synthesis) through the use of a flow cell that is incorporated into a flow path that is at least partially external to a radiosynthesis system and that provides a fluid connection between the radiosynthesis system and a vial or similar container used to collect and retain the radiopharmaceutical for later use. Such a flow cell can be positioned within a fluid flow path such that the entire volume or nearly (e.g. greater than 90%) of the entire fluid volume of a radiopharmaceutical intended for therapeutic use passes through the flow cell. Such a flow cell can be an optical flow cell, and provide an observation window that is transparent to UV and/or visible wavelengths. In such embodiments the optical flow cell permits characterization of all or essentially all of a fluid volume to be administered. Suitable optical characterization methods include absorbance, scatter, refractive index detection, polarization, and fluorescence (for example, autofluorescence of bacterial and/or fungal proteins on UV illumination). Alternatively, such flow cell can utilize electrical fields for characterization of microbial contamination. For example, such an electrical detection flow cell can include a pair of closely spaced electrodes (for example, having a spacing hat approximates the dimensions of a bacterial and/or fungal cell) that lie within the flow path and demonstrate changes in conductance or capacitance when bacteria or fungal cells pass between them. Similarly, such a flow cell can include a membrane or similar barrier that is placed within the flow path and between a pair of electrodes and that includes one or more openings with dimensions that approximate that of bacterial and/or fungal cells. Passage of microbes through such openings can be detected by changes in conductance and/or capacitance across the membrane. In some embodiments such flow cells can be incorporated into tubing or fluid lines associated with a palette or radiosynthesis system. In other embodiments such flow cells can be incorporated into a vial used for capture and storage of synthesized compounds, or, alternatively, incorporated into a cap or similar sealing device for such a vial. In preferred embodiments, such an optical flow cell or electrical detection flow cell is a disposable, single use item. Use of such flow cells advantageously permits characterization of the entire fluid volume to be delivered, thereby eliminating sampling errors. In some embodiments such an optical flow cell is used to assess analyte characteristics other than or in addition to sterility (e.g. color or clarity). In some embodiments such an optical flow cell can be assessed by a system that can be brought in to communication (for example, optical and/or electrical communication) with the flow cell externally (thereby avoiding contact with the sample) and/or temporarily.

Figure 20A:
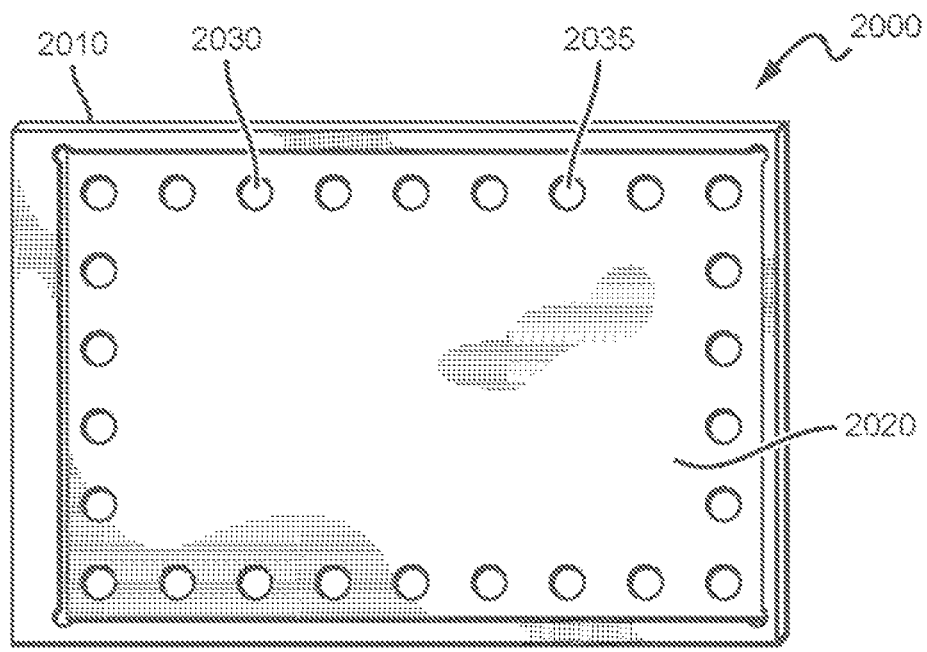
Figure 20B:
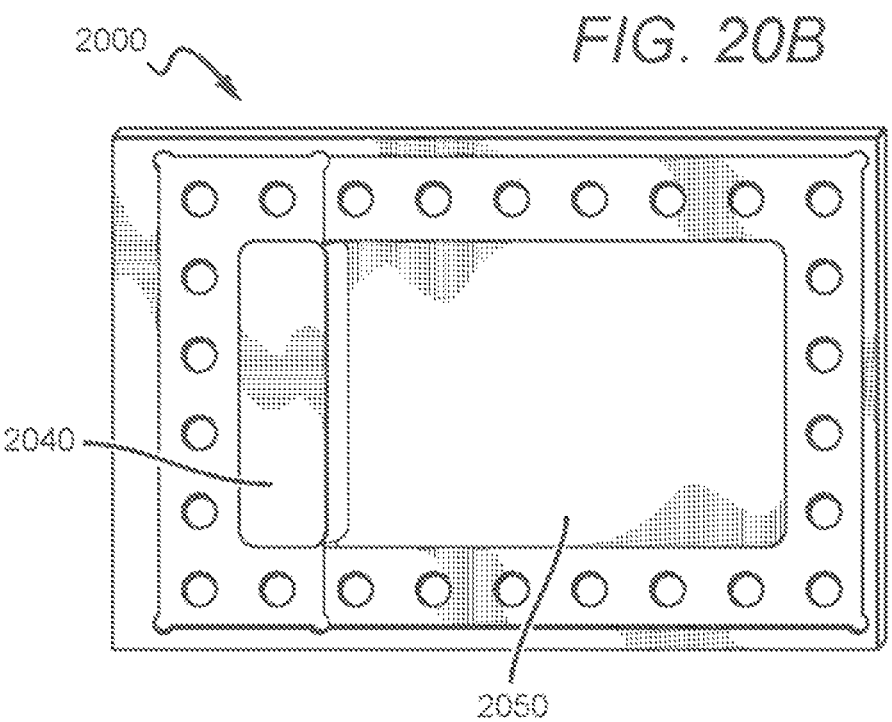

In still another embodiment, a test palette specifically configured for culture and observation of contaminating bacteria, yeast, and/or fungi is provided. In such an embodiment, a sample is transferred to such a dedicated test palette, which is then incubated at an appropriate temperature and periodically observed for growth. An example of such a test palette is shown in FIGS. 20A to 20D. FIG. 20A shows an external view of an upper surface of such sterility test palette 2000. As shown, the palette includes a body 2010 that provides primary structural support, and can be configured to correspond to or be compatible with equipment designed to work with the dimensions as described in ANSI/SLAS 1-2004: Microplates—Footprint Dimensions. Such a palette can also include a cover 2020 that can be secured to the body 2010 by one or more securing devices 2030, 2035. Suitable securing devices include screws, rivets, and adhesives. Alternatively, such a cover 2020 can be secured by material blending techniques, for example welding. FIG. 20B provides a similar view with the cover removed, and shows the relative positions of a media chamber 2040 and a gas collection chamber 2050. Such a media chamber 2040 can contain a culture media suitable for bacterial, fungal, and/or yeast culture, and include one or more optically transparent walls that permit observation of chamber contents. Such a gas collection chamber 2050 can retain a gas mixture that facilitates culture. For example, a gas collection chamber 2050 can include an oxygen containing gas mixture (for example, air) that supports the culture of aerobic microorganisms. Alternatively, such a gas collection chamber 2050 can include an oxygen-depleted or oxygen-absent gas mixture (for example, nitrogen) that supports culture of anaerobic and/or facultatively anaerobic microorganisms. In addition, such a gas collection chamber 2050 can be utilized to collect gases generated during microbial growth in the media chamber 2040. Towards that end, the gas collection chamber 2050 is in fluid communication with the media chamber 2040. In addition the gas collection chamber 2050 can be displaced (either vertically, horizontally, or both vertically and horizontally) from them media chamber 2040, such that the interface between the gas mixture and the culture media (i.e. the gas/liquid interface) is retained away from observation regions of the media chamber 2040.

FIG. 20C shows a horizontal cross section of an exemplary sterility testing palette. As shown, such a sterility testing palette 2000 can include a body 2010 that includes an access passage 2042 that provides access to the media chamber 2040. Such an access passage 2042 can accommodate a seal 2044 that reversibly prevents access to the media chamber. In some embodiments the seal 2044 can be a threaded device (for example a screw or threaded rod) and the access passage 2042 can include complementary threads. Alternatively, the seal 2044 can include any suitable device that reversibly prevents fluid access to the media chamber 2040, for example, a valve, stopper, plug, or pierceable membrane. FIG. 20D shows a vertical cross section of an exemplary sterility testing palette, showing horizontal and vertical displacement of gas collection chamber 2050 relative to a media chamber 2040, and additionally showing an observation region or window 2060 that provides optical access to the media chamber for characterization of microbial growth. Such an observation window 2060 can be, for example, an optically transparent wall or wall portion of the media chamber 2040.

In some embodiments, such a sterility testing palette can be a multi-use device that can be cleaned, sterilized, and reprovisioned for repeated use. In other embodiments such a sterility testing palette can be a single use, unitary device that can be sealed and disposed of following a single use. It should be appreciated that while the features of a sterility testing palette have been described above in terms of a separate and distinct testing palette, that such features can be incorporated into a test palette that also incorporates reagent wells, testing wells, and/or a separation device.

While a palette can include containers for each of the above described test methods, a palette can not necessarily have all of them. For example, a palette can include containers for only two of the above described test methods. According to one embodiment of the inventive concept, a palette can include at least one container for a reagent that requires sterile environment and at least one reagent that does not require a sterile environment. For example, a palette can include a container for detection of LAL reagents and a container for one of the other reagents, such as pH indicators, and both being packaged in a sterile environment. In an existing system, the LAL reagents are not combined with the pH indicators in the same environment, because while LAL reagents require a sterile environment, a pH reagent does not.

Integrated Devices and Methods for Production of Imaging Tracers

An aspect according to embodiments of the inventive concept is directed toward a system that can receive raw radioactive isotope (for example directly from accelerator) and perform radio-synthesis, quality control and dose dispensing without any user interaction. According to embodiments of the inventive concept, one system performs all 3 tasks and does not rely on the integration of 3 separate systems into one.

Figure 3:
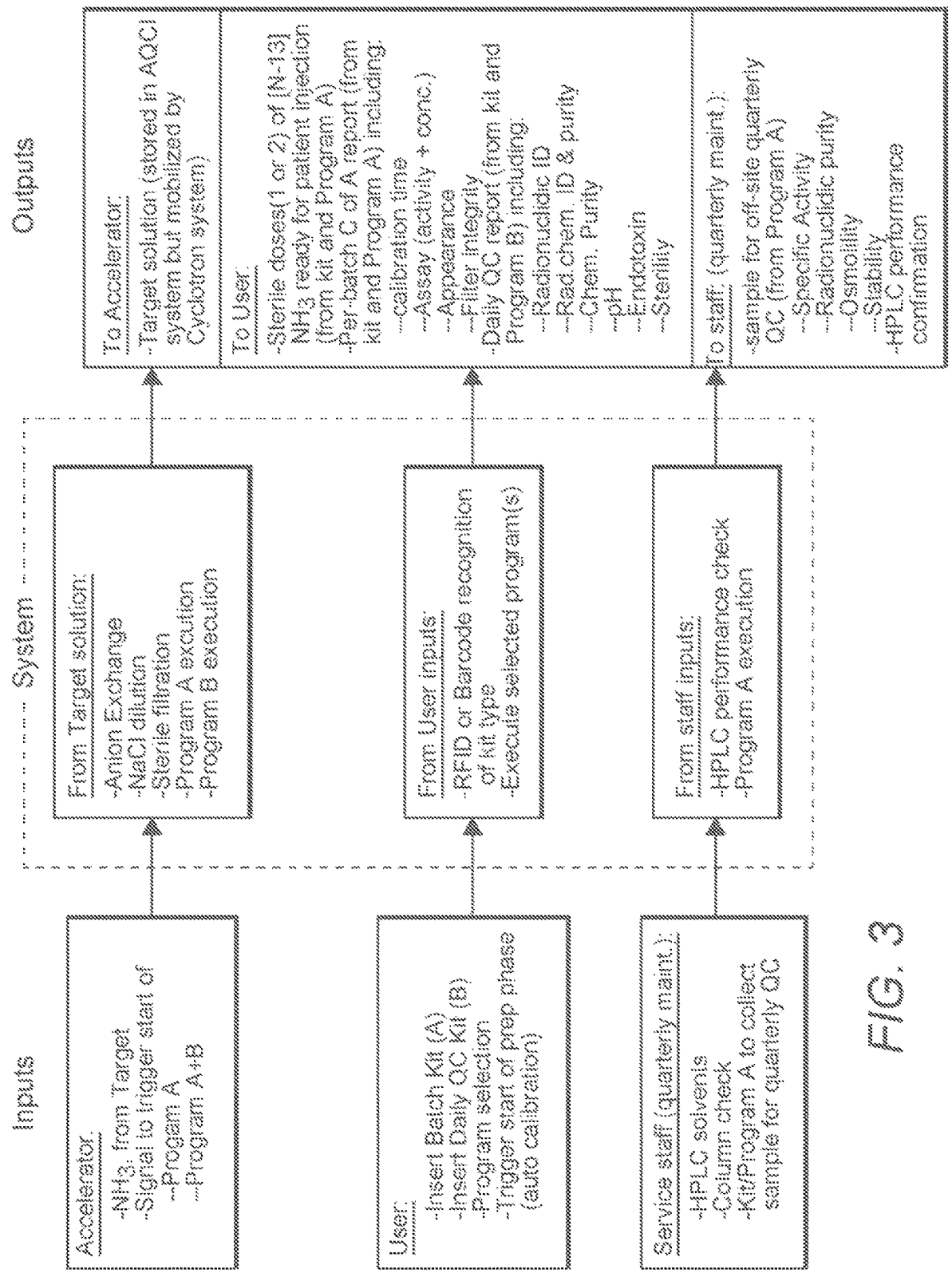
FIG. 3 is a schematic illustration of the inputs and outputs of a 13N-13 adduct synthesis, QC, and dose-dispensing system according to an embodiment of the inventive concept.
Figure 4:
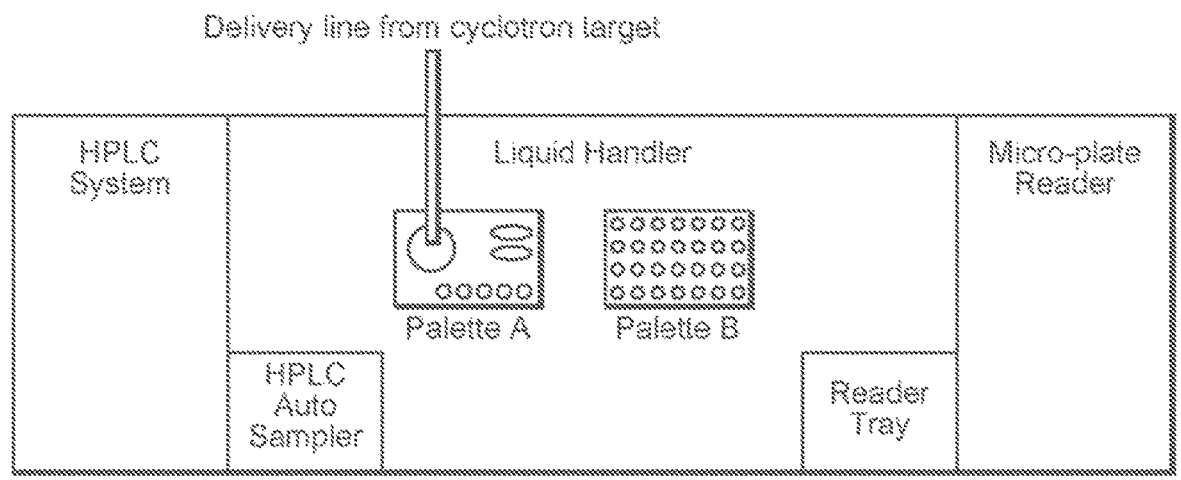
FIG. 4 shows a schematic illustration of a system according to one embodiment of the inventive concept.

The system described herein is designed to receive raw isotopes form the accelerator, carry out synthesis, QC and dose dispensing and yield radioactive imaging tracers in the form suitable for IV administration to patients. FIG. 3 illustrates the concept of an all-in-one system. Meanwhile, FIG. 4 represents one of the embodiments of such a system that is designed for the production of 13N-ammonia, which is a PET tracer used in cardiology.

In the latter embodiment the system is designed to carry out all functions of synthesis, dose preparation, quality control and dose dispensing while relying on (a) a stationary instrument including combination of a liquid handler, a plate reader and/or an HPLC interconnected with one another; and (b) single-use palettes (referred to as Kit A and B). Kit A is designed to enable all of the following: dose production, dispensing and per-dose quality control. Meanwhile, Kit B enables periodic (daily) quality control, which does not need to be performed for every dose. Therefore, the frequency of use of Kits A and B can be different. All reagents and standards are included within the kits. The user only needs to supply an HPLC solvent specified.

For example, Kit A (FIG. 4) is designed to receive raw $^{13}$N-ammonia directly from the accelerator target. It has an on-board filter 431 that assures sterility and can be tested after filtration for its integrity without being removed from the system. Kit A also contains other synthesis components such as Ion-exchange column 432 and chemicals such as saline. It also has optical detection compartments 435 which enable analysis in a plate reader (such as in a palette-caddy systems). It also has a container 433 that can be removed from the kit with final product in it and can be used for patient IV administration. Finally, Kit A has a feature 434 that makes the product accessible via a caddy, which can take a product sample to other locations within Kit A as well as to Kit B (when needed).

In one embodiment of Kit B, it receives a sample via a caddy and performs quality control tests such as described in previous embodiments. Table 5 lists all testes required for $^{13}$N-ammonia along with their frequency and outlines the enablement of these QC tests by Kits A and B.

TABLE 5

| | Measurement | Frequency of measurement | Handling |
|---|---|---|---|
| 1 | Appearance | Every Dose | Kit A |
| 2 | Assay (radioactivity yield and concentration) | | |
| 3 | Membrane filter integrity | | |
| 4 | Radionuclidic identity | Every Day | Kit B |
| 5 | Radiochemical identity & purity | | |
| 6 | Chemical purity | | |
| 7 | Acidity (pH) | | |

TABLE 5-continued

| | Measurement | Frequency of measurement | Handling |
|---|---|---|---|
| 8 | Bacterial endotoxin | | |
| 9 | Sterility | | |
| 10 | Radionuclidic purity | Periodic (quarterly) | Off-site |
| 11 | Osmolality | | |
| 12 | Specific activity | | |
| 13 | Stability | | |

It is to be noted that although $^{13}$N-ammonia is used as an example, the system is not limited for the production of this tracer. It is suitable for other PET and SPECT tracers as well as for an extended range of applications including non-radioactive products.

The other system aspects/embodiments are summarized below:

The system can be integrated (e.g., completely integrated) with accelerator and operate as one instrument with a single user interface. The system can need accelerator to send a signal that indicates isotope delivery. The system can require the user (hospital staff) to insert a combination of Kits A and B for the first (analytical) production run of the day and only kit A for each subsequent (dose) production run. The system can require the user to select a program (from menu) for either the analytical run or the dose run. The system can deliver to the user individually packaged sterile doses (using $^{13}$N-ammonia as an example).

The system can perform (a) synthesis, (b) per-dose QC, (c) aseptic daily QC, (d) dose labeling, and (e) dose dispensing functions. The system can provide a daily QC report from analytical production run (first run of each day), a Certificate of Analysis for each dose run (every batch), and individually packaged sterile doses of $^{13}$N-ammonia ready for patient administration (1 or 2 per production dose run).

User Interface

In one embodiment of the inventive concept, there are two main modes in which the host institution personnel will interact with the system: (1) quality control mode and (2) clinical mode. A third mode—(3) maintenance mode—can only be available to service personnel. It can require single-use kits (palettes) and executable programs "B" for mode (1) and executable programs "A" for mode (2).

Figure 5:
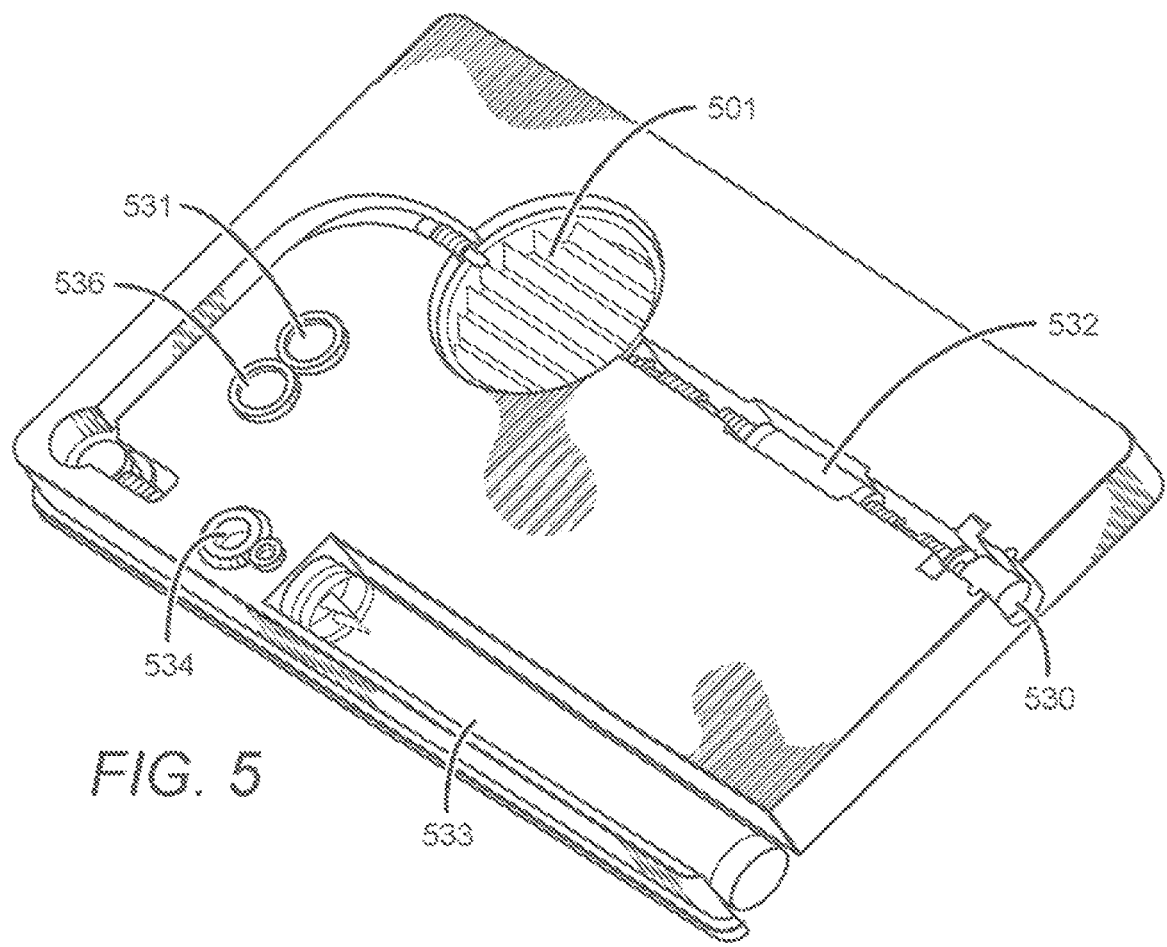
FIG. 5 provides a more detailed illustration of a kit A of FIG. 4.

The following description illustrates one example synthesis process for manufacturing $^{13}$N-ammonia. $^{13}$N-ammonia is produced in the target, so the synthesis system is fairly simple and includes mainly of filtering and dilution steps accomplished within the system. Referring to FIG. 5, the irradiated water delivered from an accelerator is introduced to kit A through an entry port 530 and passes through an anion exchange column 532 located within kit A; the irradiated water is mixed with water and sodium chloride supplied via Kit A; the mixture is passed through the filter (biological membrane) 501 located within kit A.

Dose Production and Clinical Mode

Kit A (FIG. 4) is placed within the liquid Handler. A liquid handler can be any suitable device that can perform the function of injecting, aspirating, or moving a liquid sample from one container or location to another container or location. For example, a liquid handler can include an automated pipette with exchangeable pipette tips (that function as caddies), connected with a source container of a liquid sample, to inject a given amount of the sample into the wells of micro titer plates that function as palettes. The liquid handler can further include a sample platform for moving the palettes from one location to another location, and/or moving the pipette to fill the sample in desired locations on a palette. Delivery line from cyclotron is connected to Kit A. According to one embodiment of the inventive concept, the system first performs a self-check and reports "ready to receive raw product from target" status. The target is then unloaded by accelerator pushing raw unfiltered product to Kit A within the system through the delivery line. The accelerator then gives a 30 second pulse of 50 psi gas pressure into the delivery line. During the delivery the following processes happen within Kit A. Raw product is passed through an anion exchange resin 532. Resulting solution is passed through the sterile filter 501, installed downstream from the ion exchange cartridge. Filtered product is added into the saline stored within the syringe cartridge 533. Upon delivery, the dose preparation and analysis begins. An auto sampler pipette tip aspirates 200 ul of the filtered product through a duck-bill valve 534 installed in the fluid path. Auto-sampler then dispenses this product into two wells within the Kit A: assay well 536 and clarity well 537 with 100 ul in each well. The shaker installed on the liquid handler deck shakes Kit A to mix the saline with the dose delivered. According to embodiments of the inventive concept, the system further includes a gripper that can move the entire palette from one location to another. Here, the liquid handler gripper transfers the palette to a plate reader for analysis. The plate reader reads optical parameters in three locations: assay well 536, clarity well 537 and optical cell 535 downstream of filter. Assay well is read for luminescence, clarity well is read for absorption and scattering, presence of bubbles in optical cells is determined based on the light refraction.

The readings are translated into numerical values for color, clarity and radioactivity yield and concentration. Filter integrity is reported as pass/fail value. A Certificate of Analysis (CoA) report is populated along with acceptable ranges and pass/fail results.

Kit A is then moved back to the Liquid Handler deck. Once the measurement results are available and acceptable, the user can remove syringe(s) from Kit A and use them to administer doses of $^{13}$N-ammonia to the patient.

Daily Quality Control Mode

Kit B is placed within the liquid Handler alongside with Kit A for the first production run of the day (sacrificial QC run). QC program is started including HPLC equilibration and standard injection. Once the preparation of HPLC is completed, the system is ready to accept raw product from the target.

All operations described in the Clinical Mode are carried out within Kit A, but the sample taken for analysis is also added to a specified location in Kit B.

Kit B is moved to HPLC auto sampler where the HPLC injection takes place. The HPLC runs autonomously yielding integrated chromatograms that provide the results of radiochemical identity, radiochemical purity and chemical purity (along with acceptable ranges and pass/fail results).

After the start of the HPLC analysis, the liquid handler takes samples of the product and mixes them with various reagents in different wells: for example, pH indicator(s) for pH measurement; LAL reagents for bacterial Endotoxin; and Growth media for sterility. The palette is moved to the plate reader to perform optical measurements. Once measurements have been performed, the palette is sealed and placed within the 37-degree incubator. Once all results except sterility are available and acceptable, the Certificate of Analysis is officially completed and the system can start producing clinical doses.

The palettes stored in the incubator will be taken out (automatically) once a day for 14 days (or less) and assessed in the plate reader. After 14 days of data have been collected, it is evaluated to conclude whether the sample was sterile. The results are then added to the original CoA report. If the sample fails the sterility test, the system generates an alarm.

User Interface

Software is provided by having the level of access that allows process modifications by the developer. The end user will have a level of access that allows them to choose a program and collect the CoA report.

User Perspective

In Clinical Mode, the run time is about 20 min from cyclotron to packaged product. The consumables include Custom Kit A (custom developed hardware and reagents) including ion exchange column filter, dose syringe, and analytical cells (for appearance and assay). Tasks performed include sterile filtration, per-dose tests (appearance, assay, filter integrity), dose dispensing into final container (syringe or part of syringe) and dose acceptability report (CoA).

The skill level needed is that of a technician. The software is integrated with accelerator software. In Daily QC mode, the run time is about 40 min from sample to report. All results are in one report including pass/fail information. The consumables include Kit A (custom) and B (standard HW, proprietary chemicals), and HPLC solvents. The passing criteria for clinical doses of $^{13}$N—NH3 include:

Radionuclidic ID: Half-life between 9.5-10.5 min;
Radiochemical ID: Retention time within 10% of standard;
Radiochemical purity: Product rad. peak AUC>90% of total;
Chemical purity: Product conductivity peak AUC>90% of total;
Specific activity: >10 Ci/mmol;
pH: between 4.5 and 7.0;
Bacterial Endotoxin: <175 EU/dose;
Sterility: no detectable growth.

The skill level needed is that of a technician.

Embodiments of the inventive concept include an integrated system includes a Liquid handler, a Plate reader and an HPLC, operated by a single control interface. Two types of disposable kits (palettes) designed to support the system operation: "Kit A" for Clinical mode: enables per-dose QC tests and dispensing of the dose into an injection container (syringe); and "Kit B" used together with "Kit A" for QC mode: enables daily QC tests. Methods enabled using Kit A include: Ion Exchange; Sterile filtration; Formulation; Appearance test; Assay test; Filter integrity test; and Dose packaging into syringe. Methods enabled using Kit B include: Radionuclidic identity test; Radiochemical Identity and purity test; Chemical purity test; pH test; Bacterial Endotoxin test; and Sterility test.

The consumables include Kit A (FIG. 5) and Kit B. Kit A yields doses suitable for clinical administration, and yields test results for all per-dose QC tests; Kit B (used in conjunction with Kit A) yields test results for all daily QC tests. In this embodiment, Kits A and B encapsulate all supplies for production and QC except for HPLC solvents and pipette tips (packaged separately).

The system can also include an injector accepting an injection container (syringe) of Kit A and enabling IV injection.

A system (and method) capable of accepting radioactive isotope directly from accelerator target and yielding clinically-acceptable radioactive tracer ready for human administration has been described. The system can include palettes and caddies. All reagents can be pre-packaged in a palette. The consumable contains a filter and a final product container. The filter within the disposable kit can be tested for its integrity automatically after it has been used.

While embodiments of a consumable system within which all actions of synthesis, formulation, QC and dose dispensing can be carried out (within one consumable device) has been described, the inventive concept is not limited thereto and various modifications can be made. According to some embodiments, a palette-caddy system supporting any combinations of radiosynthesis, quality control and radiopharmaceutical dose dispensing can be enabled by a combination of a liquid handler and a plate reader. According to another embodiment where the system for carrying out any one or combination of radiosynthesis, quality control and dispensing of a radiopharmaceutical product relies only on a combination of the above described liquid handler, plate reader and a liquid chromatograph interconnected with one another (and does not require traditional chemistry modules or individual analytical equipment).

According to another embodiment, QC and dose dispensing processes are inter-related in a system. An example of the latter is the determination of radioactivity concentration in the QC process is dictating the parameters of drawing individual patient doses automatically. The user requests desired doses (as amount of radioactivity at a specific time) and the system draws the volume necessary based on the concentration that it (the system) determines without the user interaction. An inter-linkage between synthesis and QC is the filter test where the same hardware used for the filtration of the product is used for the assessment of filter integrity.

Dose Dispensing

In dose dispensing applications, parallel drawing of multiple doses of radiopharmaceutical product, for example, where the doses differ from one another, can be realized according to embodiments of the inventive concept. For example, a container with the radiopharmaceutical product can be accessible simultaneously by two or more, five or more, or ten or more individual dose containers (which can or can not be syringes).

Figure 15:
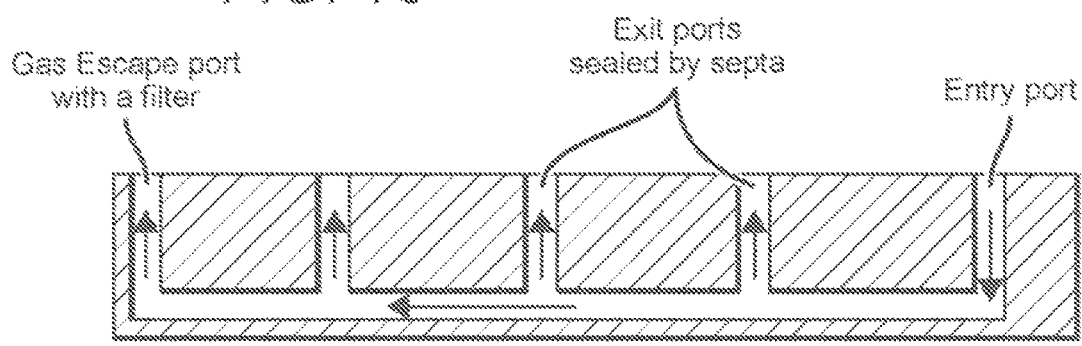
FIG. 15 illustrates an example system for parallel multiple dose dispensing according to an embodiment of the inventive concept.
Figure 16:
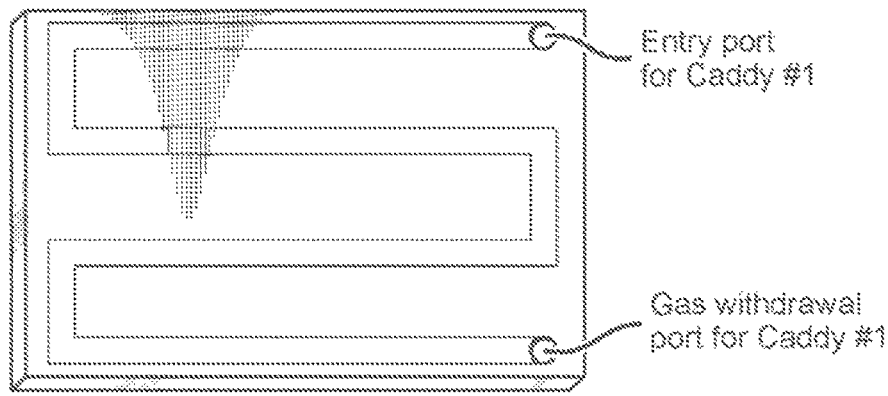
FIG. 16 illustrates an example system for parallel multiple dose dispensing according to another embodiment of the inventive concept.
Figure 17:
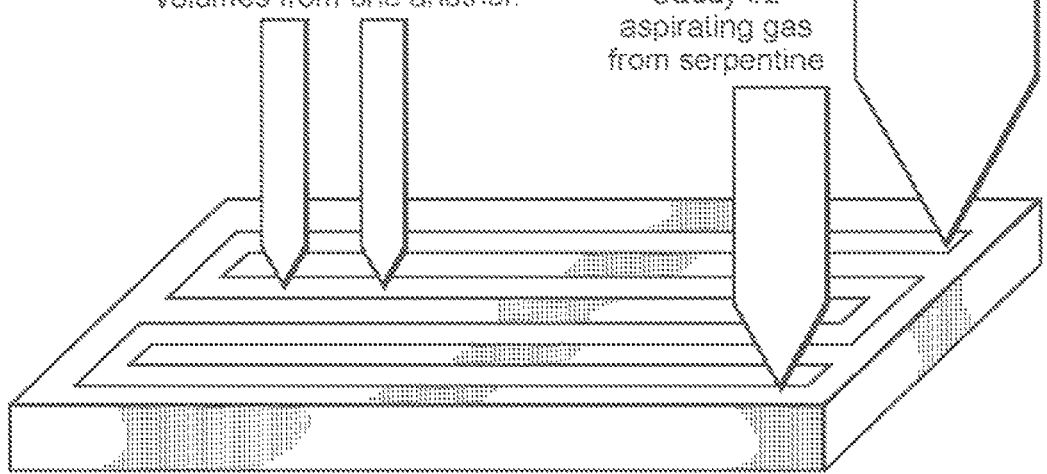
FIG. 17 illustrates an example system for parallel multiple dose dispensing according another embodiment of the inventive concept.

FIG. 14 illustrates an example system for parallel multiple dose dispensing according to one embodiment of the inventive concept; FIG. 15 illustrates an example system for parallel multiple dose dispensing according to one embodiment of the inventive concept; FIG. 16 illustrates an example system for parallel multiple dose dispensing according to another embodiment of the inventive concept; and FIG. 17 illustrates an example system for parallel multiple dose dispensing according to one embodiment of the inventive concept.

According to one embodiment of the inventive concept, a liquid handler can include removable syringes used as caddies instead of pipette tips. Prior to dose dispensing, individual dose parameters are entered in a graphical user interface (GUI). Then that data is translated into the volume each syringe needs to draw. The syringes just need to access the source container all at the same time. The latter has not been possible so far in the existing systems because the source container is a vial accessible through a septum by one syringe at a time. Embodiments of the inventive concept allow filling a flat palette with the volume of product that can be accessible to multiple syringes at the same time through a sealed horizontal surface. In one embodiment, referring to FIG. 14, the palette contains a serpentine channel of small total volume that is filled with product pressurized from a larger container or one of the caddies (which can or can not be a syringe). The larger container or one of the caddies can transfer the entire volume of product including multiple patient doses of radiopharmaceutical product by piercing a septum at the entry port of the palette. All syringes pierce the serpentine at different locations at the same time. As they pull the liquid in, the serpentine is refilled by pressurized product from the larger container/caddy. This way the total volume of the product aspirated by all syringes is much larger than that of the serpentine. The serpentine can be fully enclosed within the palette with only specific locations accessible through pierce-able septa to aspirating caddies (exit ports) as shown in FIG. 15, or the serpentine can be formed without a ceiling within a palette (like a maze or labyrinth) and then sealed on the top at once with a flat sheet, as shown in FIG. 16. Here, the palette can include an entry port for a large container or caddy with the product, and a gas withdrawal port for another caddy to aspirate gas that is trapped in the serpentine, thereby filling the serpentine with products that flows unrestricted from the caddy at the entry port. For example, caddy #1 can dock at one location at the start of the serpentine and pierce the seal. Meanwhile caddy #2 can pierce the serpentine at its end and aspirate precisely the volume of gas that is trapped in the serpentine, therefore filling it with product that flows unrestricted from caddy #1. The aspirating caddies can pierce the top seal at other locations and draw doses. Two or more caddies can aspirate in parallel and aspirate different volumes from one another.

Alternatively, the final product container can be a pierceable bag. As multiple syringes pierce it concurrently or simultaneously at multiple locations and start aspirating liquid, the bag shrinks or flattens. The volumes drawn by each syringe can be determined on the go automatically after concentration data is available from QC. Two options exist for sample dilution if needed. Either the entire product batch is diluted and syringes draw from the diluted batch container; or the syringes draw concentrated product followed or preceded by aspiration of saline from a different source. In contrast, all prior art and conventional wisdom suggest sequential dose aspiration because everyone aspirates from vials with a septa. Also, dose dispensing refers to not only drawing patient doses into syringes, but also placing syringes into individual shielded containers (commonly known as "pigs" in the radiopharmaceutical industry). So overall the user just enters what doses they want to get out of the process in the graphical user interface and receives doses in syringes inside pigs ready for shipment. The system can also label both syringes and pigs with unique identifiers referring to specific patient doses. The label can include barcodes and RFID tags for sample tracking. Embodiments described above with regard to dose dispensing can be part of the system that combines synthesis, QC and dose dispensing together, or can be a system alone just for dose dispensing, or a system that combines dose dispensing with one of synthesis and QC.

In addition, the following embodiments are all included in the scope of the inventive concept.

All surfaces touched by a sample after its delivery form the target and until final dose package in a system are single-use and disposable. The sample does not touch any multi-used cleanable surfaces. One or more kits can be enabled by palettes and caddies.

One consumable contains components needed for synthesis, formulation, QC and dose dispensing. One or multiple consumables in combination cover all aspects of synthesis, formulation, QC and dose dispensing. System can include on-board air handling and/or on-board radiation shielding.

The system allows assurance of sterility of the final dispensed product. The system can deliver sterile product starting with non-sterile isotope delivered from the accelerator target. The reagents are pre-packaged in a disposable kit. The analytical reference standards can be pre-packaged in a disposable kit. Both reagents and analytical standards can be pre-packaged in one disposable kit.

Disposable kits designed for one or more or any combination of: formulation, QC, dose dispensing, and synthesis have been described. The system can be mobile. System can produce a product and generates a batch record. The system can also include the accelerator and can start the process with non-radioactive substances leading to a radioactive product ready for patient administration.

A system can use target pressure to drive parts of the synthesis, formulation, QC, dose dispensing or the entire process. The sterile filter can be attached to the final dose container/integrated with it.

One kit, package, cartridge or palette including filter, final dose container and analytical functions has been described. The system can also carry reagents and/or standards. The system can or can not have on-board electronics.

Embodiments of this system include but are not limited to systems for the production or PET and SPECT tracers, method and system where the consumable (or choice of consumable kit) determines the process parameters.

The consumable is the carrier of part or all of information that determines the process to be executed (including accelerator, synthesis, formulation, QC and dispensing).

In the system according to embodiments of the inventive concept, all the user needs to do is turn it on and select a consumable kit to insert into the system and the rest is done automatically yielding an injectable product at a known time.

The consumable that has all components necessary for the generation of the product is also the carrier of the recipe or triggers a choice of recipe within the system that recognizes this consumable automatically.

A system can include a storage sub-system with multiple types of consumables on board. So the user only has to input what product needs to be delivered and when, and the system does the rest including starting the accelerator at the right time and choosing the right consumable to be used. Consumables can be stored in a controlled (air and temperature) environment within the system.

The system can include input means, such as buttons, for selecting the tracers, such as $[^{18}F]$-FDG, $[^{18}F]$-FLT, $[^{11}C]$-Choline, $[^{13}N]$-ammonia, $[^{18}F]$—NaF, $[^{18}F]$-Florbetapir (Amyvid) etc., leaving the user just to input the time when the product is needed.

A system where sterility of the sample is assessed without direct contact between sample and the detector has been described.

A system according to the present embodiment can have a continuous fluid path between the sterile filter and final dose container. The dose dispensing palette has at least one quality control function/feature.

Separate Pharmacy from the Manufacturing Site of Radiopharmaceuticals

Traditionally, facilities that produce PET tracers also operate as pharmacies that fill the prescription for each patient. One of the main reasons for such an arrangement is that the quality assessment on the final product relies on physical inspection by the pharmacist, who cannot fill the prescription unless he/she personally verified the product as suitability for human use.

Automated instruments that can assess all parameters of quality of a radiopharmaceutical with quantitative measurements and without human input according embodiments of the inventive concept, offer a unique opportunity to separate the manufacturing of PET tracers from the pharmacy and allow various combinations and ratios between pharmacies and manufacturing sites.

In one embodiment, a PET tracer (or another radiopharmaceutical) is subjected to automated multi-parametric analysis. The results of such analysis are captured and stored electronically. These results can also be viewed remotely allowing a pharmacist to review the test results without being co-located with the sample of the product. The pharmacist who reviews product quality remotely can then also release it for patient delivery remotely using secure electronic signature. Once such an arrangement is enabled, one pharmacist can be able to support multiple production facilities.

In one embodiment, the workflow could proceed as following. PET tracer is produced at a manufacturing facility. A sample of the product is drawn by a technician at that facility and injected into an automated QC instrument (located on-site). Once the instrument processes the sample and yields the results on all QC parameters, a report is sent securely to the pharmacist at a remote location. The pharmacist reviews the report and if all results are acceptable, releases the product for patient use via secure electronic approval/signature. The Technician on-site can then package and ship product (PET Tracer) to the imaging center where it will be administered to a patient.

According to one embodiment of the inventive concept, a single pharmacy offers its services to multiple production facilities at different locations (using automated instruments). This pharmacy will employ one or more pharmacists and eliminate the need for having a licensed pharmacist physically present at each production facility.

There are arrangements where production and dose dispensing are separated. The remote pharmacist will get the report from the production facility and then send his/her approval to the dose dispensing facility. This way both of those types of facilities do not need to have a pharmacist on their staff.

Having thus described in detail various embodiments of the inventive concept, it is to be understood that the invention defined by the above paragraphs is not to be limited to particular details set forth in the above description as many apparent variations thereof are possible without departing from the spirit or scope of the inventive concept.

At least the following embodiments have been described. A palette system is configured to hold one or more vials. The palette can have permanent fixtures for holding liquids, solids or gases. The palette can have a plurality of wells and one of the wells does not have a floor and is effectively an unrestricted see-through opening.

A method includes insertion of a container (vial) into the palette or instrument and the insertion of a container (vial) into the palette or instrument triggers other events. The palette can be made of more than one kind of materials. The palette can have some (permanent or removable) liquid containers that are made of one material and others of another material. The palette can contain both organic and aqueous reagents. The palette can contain non-compatible reagents. The palette can be coated with a protective film (completely or partially). The palette can have different size containers placed in a regular arrangement or randomly. The palette can have containers of various shapes. The palette can be sealed by one type of seal in some locations and by a different type of seal (and/or some unsealed) in other locations. The container volume can be reduced via an insert. The palette can have inserts that hold fluid/solid/gas. The palette can have inserts that displace liquid/solid/gas. The palette can contain chromatographic components. The palette can include stationary phase. The palette can include mobile phase. The palette can include TLC components. The palette can allow motion of liquid. The palette can allow motion of mobile phase along solid phase. The palette can include channels. The palette can include an injection loop. The palette can include a septum. The palette can include a septum-piercing device. The palette can include one or more caddies in presence or in absence of other features. The palette can include containers with or without reagents and/or seals. The palette can include optical features. The palette can include features that modify light. The palette can include sources of light. The palette can be utilized with devices that detect and/or quantify light or other optical signals. The palette can include a built-in mixer that effectively mixes 2 liquids or a liquid and a solid. The mixer can or can not be activated by one or more caddies. The mixer can be activated pneumatically, optically, mechanically or electrically. The palette can include radiation shielding. The shielding can protect the user or protect one signal from another or signal from noise. The palette can include a removable or permanent shielding. The shielding can be within a caddy. The palette can have no port. The palette can be configured to receive a sample without a port. The palette can be configured in such a way that any container can receive the analyte or any container is accessible at all times. The palette can include no channels and or valves. The palette can have all containers isolated from one another. The palette can have no fluid path(s). The palette can have no optical cells. The palette can be packaged with a combination of 2 or more of liquids/solids/gases. Each container within a palette can be sealed individually with different seals broken at different times in the process. The seals can be broken in any order (not in a rigidly defined sequence). The containers within a palette can be accessed in any order (once or more than once). The palette can have no movable components.

A palette can include reference materials to which the analyte can be compared along one or more properties. The palette can include all materials necessary for performing daily system suitability tests of an instrument (automatically). There can be a recognition system between the instrument and palettes (and/or caddies). The palette can include reagents and/or information (about reagents, methods, analytes or other aspects). The palette where the pattern of filled and empty (or variably filled) containers can be used to convey information. The palette can be made of two components that are filled/sealed individually.

A method where analyte is delivered to a palette in a syringe has been described. A palette and/or caddy system configured to draw/package doses for individual patients has been described. Some tests can be performed within a palette immediately after receipt of analyte while other tests can be delayed. Methods can require incubation of the palette prior to reading optical signals from it. The palette can be configured for performance of one or more tests in one instrument and another set of one or more tests in another instrument (or another facility). The results from one palette tested in different instruments can be combined into one report for the same analyte.

A palette can have gas flow enabled through it. The palette can have laminar gas flow through it. A palette can have a bio safety environment around it. A palette can have such environment only around the palette but not within the rest of the instrument. A palette can have part of it under the laminar flow or bio-safety system. A palette can have no walls. Fluids/solids/gases can be confined by methods other than physical barriers. Palettes can have designs represented in the figures and methods of using them. A palette can have inert or sterile atmosphere created just above the palette and protecting only its contents. A palette can have permanent fixture under the palette that assures inert environment above or around the palette. The fixture above can or can not penetrate the palette. Air routed to palette can pass through a HEPA filter. A HEPA filter can be incorporated into a palette. Caddies can create an inert/sterile environment around and within the palette.

A device can be capable of assessing two or more quality control parameters from a single introduction of sample into a palette. A palette can have reagents for one or more tests required for quality control. The quality control can be performed for a radiopharmaceutical. The device can include a liquid handler. A device can include a spectrophotometer. A device can include a plate reader. A device can include an HPLC. The device can include a spectrophotometer and an HPLC. A device can be capable of accepting a palette with reagents and a single well with analyte and distributing analyte between test locations within palette. A device can be capable of assessing optical signals corresponding to chemical properties resulting from reactions within a palette. A device can be capable of routing a fraction of analyte to HPLC. The routing can be performed via a caddy.

A method of assessing quality control parameters of analyte can be by reacting the analyte with various reagents and the reactions producing an optically detectable signal. The signal can be correlated with a specific measurement of a chemical, physical or nuclear property. A method of determining whether the sample is colored or colorless can utilize continuous spectrum absorption measurement and a threshold that is preset for a specific range of wavelengths. The wavelengths are in the visible range of the spectrum (360-700 nm.)

A method of measuring exact Kryptofix™ concentration in a sample can be via an absorption measurement at one or more wavelengths of light being passed through the mixture of sample and indicator in a palette. The indicator can include a transition metal salt and a colorimetric indicator for measuring of this metal. Whether the sample is of acceptable quality can be determined by comparing the measurement against a preset value or range of values.

A method of measuring exact pH of a sample can be via absorption measurement at one or more wavelengths of light being passed through the mixture of sample and indicator in a palette. Whether the sample is of acceptable pH can be determined by comparing the measurement against a preset range of values.

A device and a method for Pyrogen testing without the requirement of liquid flowing through a channel have been described. The device for Pyrogen testing can be in combination with other tests. The device can be a palette. The Pyrogen testing can be conducted in a device combined with other tests. The Pyrogen testing can be conducted in parallel with other assessments.

A method of assessment of radioactive sample half-life and radionuclidic purity without a dose calibrator has been described. A method of continuous measurement of radioactive decay for determination of half-life and radionuclidic purity has been described. A method of determination of half-life and radionuclidic purity without shielding the sample from other sources of radiation or other samples has been described. A method of assessment of radioactivity concentration can be conducted without a dose calibrator. A method for determination of the radioactivity concentration can be conducted without shielding the sample from other sources of radiation or other samples.

A method of measuring exact solvent concentration in a sample can be via an absorption measurement at one or more wavelengths of light being passed through the mixture of sample and indicator in a palette. A method of determining whether the sample has acceptable solvent concentration can be conducted by comparing the measurement against a preset value or range of values.

A method of performing chromatography within a palette has been described. A device capable of performing chromatography within a palette has been described. A device for Radio-TLC or radio HPLC within a palette has been described. A method for Radio-TLC or radio HPLC within a palette has been described. A device for TLC assessment in combination with scintillating liquid has been described. A method for TLC assessment can be in combination with scintillating liquid. A method using scintillating liquid for chromatography has been described. A method for chromatographic separation using a media-filled small column or capillary on a palette has been described.

A device and method for delivery of sample to analytical HPLC via a palette/caddy system have been described. A device/method where an HPLC sample is yielded by a caddy on a palette have been described. A method for HPLC injection and results integrated with sampling and reporting for other QC tests has been described.

A device can have all calibration samples required to be processed prior to analyte pre-packaged on a palette. A device and a system that perform system suitability testing and sample analysis in one process and using the same package. A package can be a pre-loaded palette. A method where a single injection into HPLC allows analysis of chemical and radiochemical purity as well as organic solvent concentration or any other combination of these tests has been described. A palette can contain chromatographic media. The media can be a TLC plate. The media can be a packed column. A device can be utilized for separating chemical mixtures. The components of a separated mixture can be detected. The components can be identified. The amounts of components can be quantified. The radioactive components can be detected by their radioactive signal. A method can utilize a scintillating liquid. Such a scintillating liquid can be in very close proximity to the stationary phase, but not in contact with the stationary phase. Alternatively, a scintillating liquid can be a component of the mobile phase.

A device and a method for performing chromatography using a stationary phase and mobile phase where mobile phase contains scintillating material have been described. A device for performing chromatography using a stationary phase and mobile phase where stationary phase contains scintillating material has been described. A device for Sterility assessment with a spectrophotometer has been described. A method for Sterility assessment can include a spectrophotometer. A method of Sterility assessment can be conducted in a palette (with all options for it). A quantitative sterility assessment can be conducted according to the rate of colony growth. A method of filter test with data/results feeding directly into an overall QC report automatically, and leaves no room for human judgment.

Although the above description discusses implementations of the inventive concept within the framework of an automated or semi-automated system, it should also be appreciated that another aspect of the inventive concept is the arrangement of reagents and test sites that facilitate the characterization of a compound (for example, a radiopharmaceutical) within one or a small number (e.g. 3 or less) test fixture (such as a microwell plate), and thereby permit the characterization tests noted above to be performed by an individual technician using limited laboratory space. In a preferred embodiment of the inventive concept, the results of such testing can be determined using a single optical instrument.

As noted above, characterization of radiopharmaceuticals prior to clinical use requires testing for a wide variety of factors, including color, clarity, pH, residual 5,6-Benzo-4,7, 13,16,21,24-hexaoxa-1,10-diazabicyclo[8.8.8]hexacos-5-ene (Kryptofix™), radionuclide identity, radioactive content, residual organic solvent (e.g. acetonitrile, ethanol, etc.), and/or sterility. In some embodiments of the inventive concept all testing is carried out utilizing reagents, preparative regions, and testing regions encompassed within a single palette. In other embodiments testing is carried out using reagents, preparative regions, and testing regions distributed over two or more palettes. In still other embodiments, all reagents used for testing can be stored on a reagent storage device (for example, a reagent palette) and all tests can be performed on a testing palette. In a preferred embodiment, a testing palette and a reagent storage device carrying appropriate reagents are provided together as a kit.

A palette of the inventive concept can include one or more reagent regions, utilized for storing reagents utilized in assays. Such reagent regions include wells (defined volumes molded into the body of the test palette) and/or holders for vials, tubes, or similar devices. In some embodiments, a palette can include both wells and holder for vials and tubes. Wells used for storage of reagents can be covered with a sealing material (for example, a polymer or foil). In some embodiments such a sealing material can be penetrated by a fluid handling device (for example a pipette tip, hypodermic needle, etc.) without the need for removal. Wells used for reagent storage can be dimensioned to enclose volume ranging from less than 1 µL to 5 mL or more. Similarly, vials or tubes used for reagent storage and configured to be held by the palette can be dimensioned to enclose volume ranging from less than 0.1 µL to 10 mL or more. Such wells, vials, and/or tubes can be configured to retain solids, liquids, or gases. The number of wells, vials, and/or tubes designated for reagent storage can range from 1 to 100 or more, and preferably number between 10 and 30. Such vials or tubes can be open or sealed by a number of different options including polymer, foil, or screw-tops.

Wells used for the performance of optically read tests can have any suitable configuration. Such a well has an opening that is parallel with the upper surface of the palette (through which materials can be added to the well), a wall or set of walls extending downwards from the opening, and an observation window connecting the lower portion of the wall or walls at the bottom of the well. In some embodiments the walls subtend towards the central axis of the well as they descend, such that a vertical cross section of the well shows a decreasing diameter and the observation window has a smaller diameter than that of the opening. It should be appreciated that such a shape advantageously increases the optical path length of the well while maintaining a wide opening that simplifies alignment of fluid transfer devices (such as pipettors), while also reducing the required volume of fluid relative to a well having a conventional rectangular or square vertical cross section. In such embodiments the observation window has a diameter that is less than about 50%, 40%, 30%, 25%, 20% 15%, 10%, and/or 5% of the diameter of the opening. In a preferred embodiment, the profile of the subtending walls is curvilinear (for example, describing a portion of a parabola), which advantageously directs fluid flow to improve mixing on fluid addition. In some embodiments, a horizontal cross section of such a well is circular. In still other embodiments the wall may extend substantially vertically (i.e. within 10° of vertical) for a distance before subtending centrally to provide a loading region within which a dispensing fluid handling device can move relatively freely.

Figure 21A:
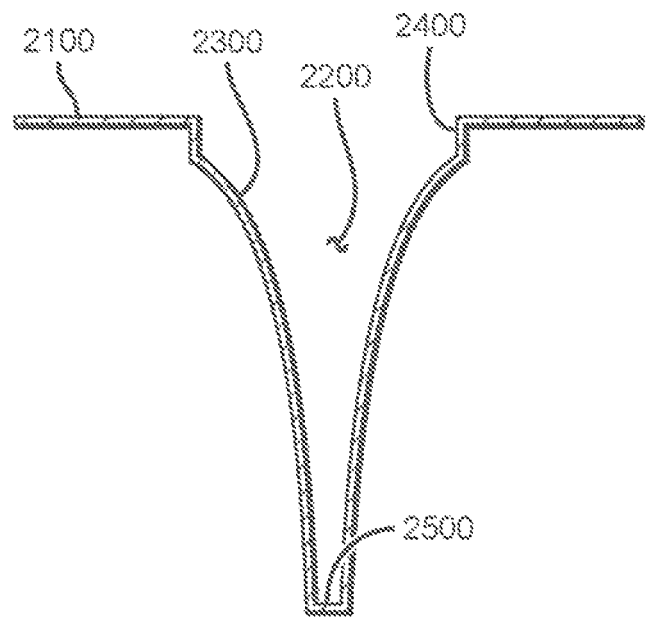
FIGS. 21A and 21B depict various views of an exemplary test well of the inventive concept.
Figure 21B:
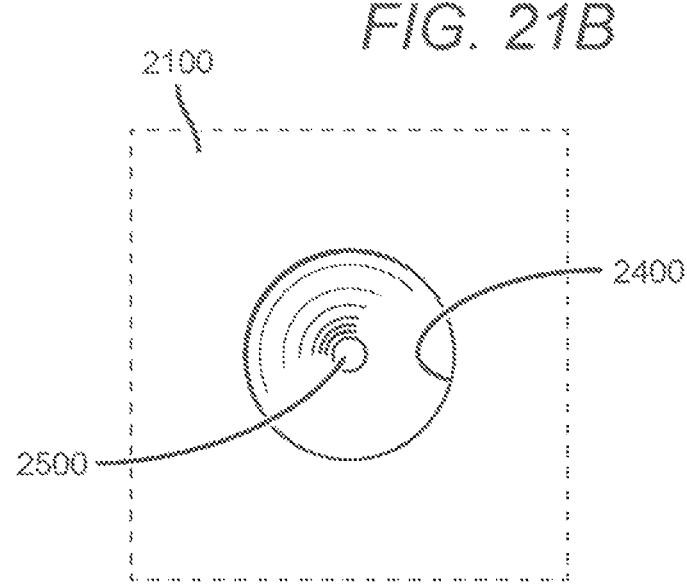

An example of such a test well is shown in FIGS. 21A and 21B. FIG. 21A depicts a vertical cross section of an exemplary test well, depending downwards from the surface 2100 of a test palette. Such a well has an opening 2200 through which materials are introduced to the interior volume of the well. Depending downwards from the opening 2200 are one or more wall 2300. As shown, such a wall 2300 can have a profile that subtends toward the center of the test well as distance increases from the opening 2200. In a preferred embodiment this profile is curvilinear (for example, as a parabola or a portion thereof). Typically fluids are delivered to such wells vertically; such a profile impels such vertically moving fluids laterally and serves to improve mixing. The wall(s) 2300 terminate in an observation window 2500, through which light can be introduced to well contents and/or measured from well contents. Optionally, such a test well can include a loading region wherein the wall 2300 is essentially (i.e. within 10 degrees of) vertical for a portion of the well depth. Such a loading region can permit partial insertion of a fluid delivery device, such as a pipette, into the well in order to improve the accuracy of fluid delivery. FIG. 21B provides a top-down view of a test well of the inventive concept. Although depicted as having a circular cross section, such a well can have an oval, square, rectangular, and/or polygonal cross section. In some embodiments of the inventive concept the cross section of a test well can vary at different positions along the depth of the well.

A palette of the inventive concept can include one or more test regions. Such test regions can be characterized as preparative regions and/or assay regions. Preparative regions are utilized for intermediate steps of an assay process (i.e. steps that do not result in a readable signal). Such preparative regions can be wells or vials/tubes held by the palette. In some embodiments, a portion of a preparative step can take place away from the palette. For example, a vial held by a palette can be removed, mixed and/or centrifuged, then returned to the palette (at either the same or a different position).

Assay regions are utilized for generation of a readable result, and can receive test sample materials directly or following treatment in one or more test regions. Some test regions are represented by wells that serve as areas for optical characterization. Such test wells can be transparent to permit gathering of absorbance data. Other test wells can be opaque but with open tops to permit gathering of emitted light (for example, fluorescence, phosphorescence, luminescence, and other EM radiation). In some embodiments a test well can have a composition and/or optical properties that differ from those of surrounding material (for example, transmission of a different range of optical wavelengths) in order to facilitate gathering data from a test performed in or read from such a well.

In some embodiments of the inventive concept, the test region includes a separation device or feature, for example a plate, column, or capillary. Such a plate, column, or capillary can support or enclose a separation media, for example a gel or chromatography media. Suitable separation gels include agarose, polyacrylamide, and mixtures thereof. Suitable chromatography media include silica, ion exchange media, reverse phase media, hydrophobic interaction media, size exclusion media, affinity chromatography media, dye affinity chromatography media, and aminophenylboronate media. Preferred chromatographic media include silica, modified silica, silica-impregnated paper or other fibrous support, silica modified with polar or nonpolar functional groups including alkyl chains; or support featuring large grafted molecules such as antibodies or other immunoreactive species. Acceptable chromatography modes include normal or reverse phase. Solvents for use in chromatographic separations are selected to be compatible with the species to be characterized, the chromatographic separation media, and the chromatographic separation mode. Such solvents can be aqueous solvent systems, polar organic solvents, nonpolar organic solvents, and/or mixed solvent systems. Preferred solvents include acetonitrile, hexane, ether, methylene dichloride, methanol, water or mixtures thereof.

Such separation device can include an observation region, through which optical data is collected. In some embodiments the observation region can be an optically transparent window that occupies a portion of the separation device. In other embodiments the separation device has an exposed region (or, in the case of a coated surface is essentially entirely exposed) that serves as the observation region. In still other embodiments a wall and/or supporting surface of a separation device, and the entire separation device can act as an observation region.

Embodiments of pre-chromatographic derivatization chemistries include conjugation of analytes to molecules assisting in detection of analytes, e.g. fluorescent hydrazines, hydroxylamines, carboxylic acid derivatives and other examples. Such a plate, column, or capillary can be arranged parallel to the major plane of the palette, for example within a trough or series of interconnected wells running along the long axis of the palette.

Assays performed in such a test region include separation of the components of a mixture across such a device. For example, a sample containing a mixture of compounds can be applied to one end of a column packed with a separation media and induced to move along its length (for example, by movement of a solvent and/or application of an electrical field). Components of the sample separate from one another as they move along the column, and can be observed doing so. In some embodiments of this separation is observed using a microplate reader, where positions associated with the wells of a conventional microplate correspond to points along the separation device at which optical data is gathered. In some embodiments of the inventive concept the microplate reader can be configured to scan along the separation device is increments smaller than those corresponding to the spacing of a conventional microwell plate, thereby providing a continuous or nearly continuous body of positionally coded optical data. In some embodiments, such data can be gathered at a single time point. In other embodiments, such data can be gathered at multiple time points, thereby permitting estimation of an end point and/or of a rate of travel along the separation device.

Figure 19B:
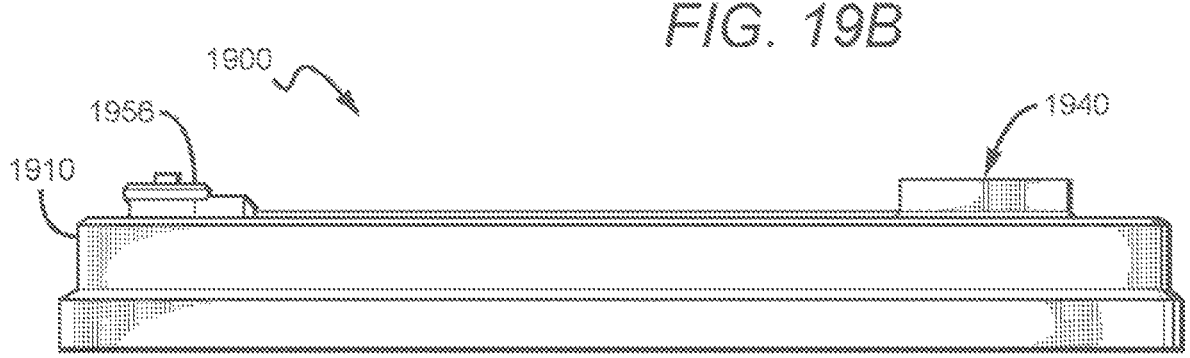
Figure 19C:
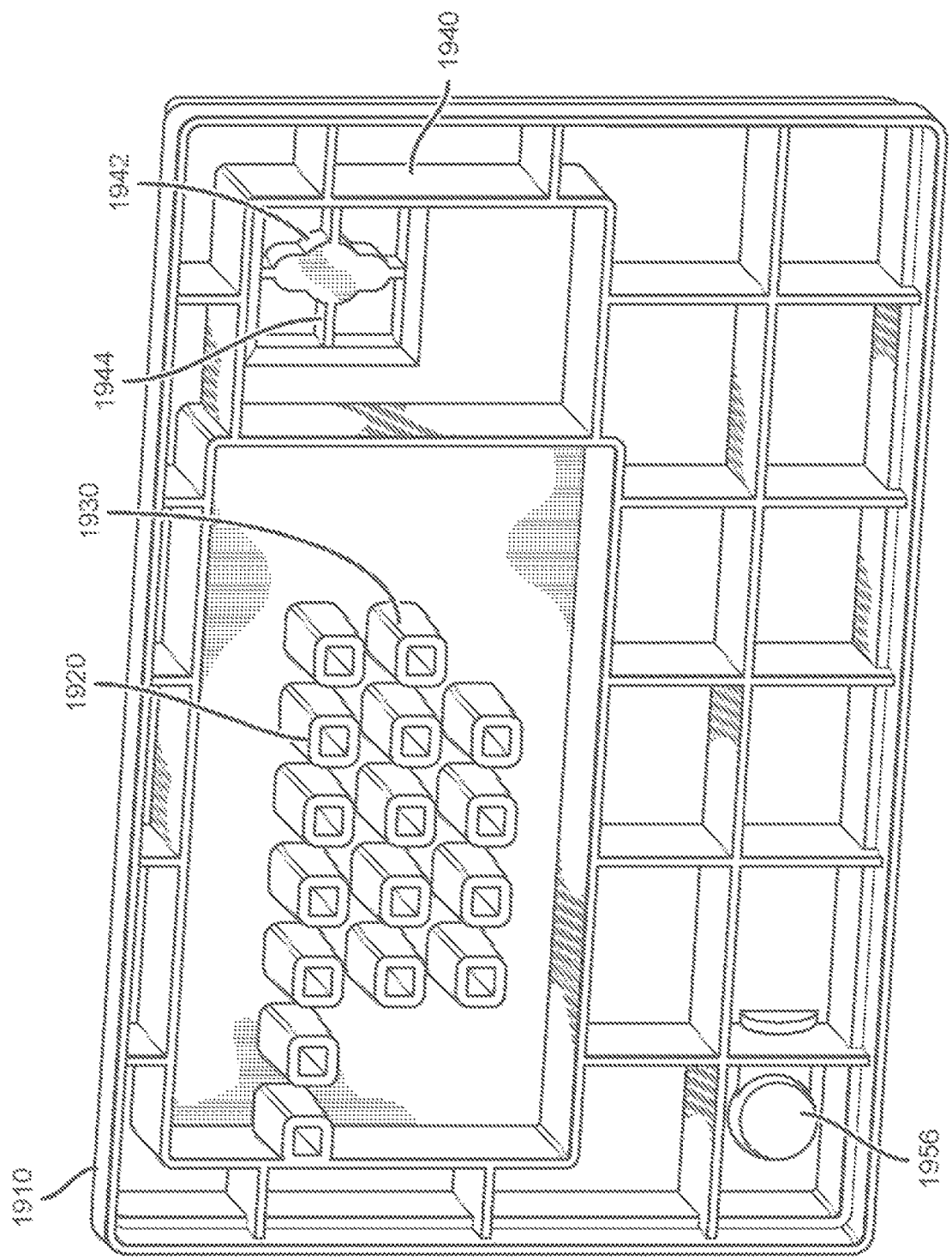

An example of a test palette of the inventive concept is shown in FIGS. 19A to 19C. FIG. 19A shows a view of the top of a test palette 1900 of the inventive concept. Such a palette includes a body 1910 that provides structural support and can serve as a heat sink when temperature differentials are applied. In preferred embodiments, such a body 1910 conforms to or is compatible with the 2002 SPS/ANSI proposed standard for microplates. As shown, such a palette can include one or more well(s) 1920, 1930. Such wells can be used for performance of one or more steps of a test and/or can be used for storage of reagents used in such tests. Such a test palette can include a thermally isolated region 1940. Such a thermally isolated region 1940 can include a thermally isolated well 1942 that is connected to the test palette by one or more ribs or supports 1944. Such a thermally isolated well 1942 can have a low thermal mass, for example by being composed of a thermally conductive material and/or having walls 1945 of reduced or minimal thickness. Such ribs or supports 1944 can have low heat conductivity, for example by being composed of a thermally insulating material and/or having a reduced or minimal cross section.

In embodiments of the inventive concept the thermally isolated region 1940 is arranged and composed such that the thermally isolated region and/or the thermally isolated well 1942 reach thermal equilibrium in less than about 50%, 40%, 30%, 25%, 20% 15%, 10%, and/or 5% of the time required for one or more test regions 1947 located outside of the thermally isolated region 1940 to equilibrate to a new temperature. This advantageously permits test methods with incompatible temperature requirements to be performed on a single test palette. For example, a test method that is sensitive or otherwise incompatible with varying temperature during the course of the method can be performed in a thermally isolated well, whereas a second test method that is tolerant of varying temperature can be performed outside of the thermally isolated region. On transferring the test palette to at temperature controlled region with a temperature different from that of the initial temperature of the test palette (for example, an incubator or a refrigerator), the thermally isolated well rapidly equilibrates to and maintains the new temperature, whereas the remainder of the test palette equilibrates to this new temperature slowly. As a result, the temperature sensitive method rapidly reaches a relatively constant temperature. This advantageously reduces the time required for performance of such assays while permitting testing of reagents with differing environmental tolerances on the same testing fixture (e.g. in parallel or at the same time).

As shown in FIG. 19A, such a test palette can also include a separation region 1950, which includes a separation device 1952. Although depicted as a microcolumn or capillary, as noted above such a separation device 1952 can have a variety of configurations, including both enclosed columns or capillaries that include separation media and open beds or plates that support exposed separation media. In embodiments of the inventive concept, such fluid flow paths can include separation media, but are unencumbered (i.e. do not include valves or similar impediments to fluid flow). As shown, the separation region 1950 can include separation device support, which can be continuous (for example, a groove) or discontinuous (for example, a series of columns, pillars, and/or clamps). In some embodiments, a separation region 1950 can include a sample loading area 1956 associated with an end of the separation device 1952. Such a sample loading region 1956 can include a volume for retaining a sample to be loaded onto the separation device 1952, and can include a device for applying a pressure differential along the separation device (for example, a deformable membrane or a region that can be pressurized by the introduction of a gas or liquid).

FIG. 19B depicts a side view of such a testing palette. As shown, the thermally isolated region 1940 can be elevated above the body 1910 in order to provide increased exposure to the ambient environment. Similarly, a sample loading region 1956 can be elevated in order to improve access to automated and/or manual fluid delivery devices). FIG. 19C shows a view of the lower surface of such a test palette.

In some embodiments of the inventive concept, the optical data gathered originates from an observable label (for example, a fluorescent dye) that is attached to a radiopharmaceutical compound and/or a reference compound for purposes of observation. In some of such embodiments, different tags can be associated with different compounds to permit differentiation.

In other embodiments of the inventive concept, the radiopharmaceutical can provide sufficient light for detection while within the separation device, for example through the generation of Cherenkov radiation. It should be appreciated that such an embodiment is particularly suitable for detection of radiopharmaceuticals that include positron-emitting radionuclides (such as $^{18}$F).

Surprisingly, the inventors have found that Cherenkov radiation of radiopharmaceutical compounds within a column packed with chromatographic media is of sufficient intensity to permit reliable detection using a microplate reader having a luminescence mode. In the prior art radiation measurements from such materials required the sample to be exposed to a scintillating material. This was accomplished by either mixing the sample with a scintillating liquid or by placing it in contact (or close proximity) with a scintillating solid (e.g. plastic) material. Such requirements limited the utility of the test as they limited material choices and required additional reagents. In contrast with that approach, the new method requires no additional materials beyond those found in the sample itself in order to perform measurements as the observed Cherenkov emission originates from the disintegration event itself. Cherenkov radiation is related to the fact that some particles formed in the disintegration effect carry sufficient energy that they would have velocities faster than light if this energy was not released in some form. The excess of energy is dissipated in the form of broad spectrum (i.e. UV to visible) light. The amount of light observed depends on the media where disintegration occurs. Under achievable conditions measurements of Cherenkov emission can be captured by luminescence detectors, for example luminescence detectors available on commercial microplate readers. The inventors have found that such measurements correlate with the amount of radiation in the samples. These measurements can be used successfully used in a wide variety of sample characterizations, including position and/or speed along the separation media, determination of radioactivity concentration, and determination and half-life of $^{18}$F-FDG or other radiopharmaceutical samples.

This direct characterization of radioactivity through direct observation of Cherenkov radiation in real time permits effective radio-chromatography within the confines of a palette compatible with devices that handle microwell plates (i.e. dimensioned in accordance to ANSI/SLAS 1-2004: Microplates—Footprint Dimensions) as part of a set of radiopharmaceutical characterizations performed in parallel on the same palette. In an exemplary radio-chromatography method of the inventive concept a capillary packed with stationary phase is permanently (or, alternatively temporarily) mounted within a palette. The sample is added to one end of the capillary, and is either pulled or pushed into the capillary (for example by capillary action and/or a pressure differential). The motive force can have multiple options including vacuum, gas pressure, liquid pressure, adsorption, etc. A mobile phase can then be applied to the same end of the capillary as the sample. The motive force then moves the mobile phase through the capillary, picking up the sample and separating it into bands or spots based on the interaction of the sample components with the stationary phase. Once the passage of the mobile phase through the column has progressed sufficiently, Cherenkov emission can be measured along all or part of the length of the column using luminescence detector of the plate reader. The measurement intensity is plotted against the measurement position along the column resulting in a radio-chromatogram. Alternatively, multiple reads can be performed as the mobile phase travels through the capillary and velocities of one or more observable sample components calculated. The new invention enables radio-chromatography with direct measurement of Cherenkov emission from the column and does not require any scintillating materials (unlike earlier inventions).

Test palettes that include such separation devices can also include wells or similar recesses that are configured to support sample application and/or solvent provision to the separation device (i.e. a loading well). For example, a well can be provided at a position proximal to a loading terminus of a column or capillary that includes a collar or seal in one lateral wall, which serves to position the open loading terminus of the column or capillary at a point below the opening of the well. Application of a sample and/or a buffer or solvent to such a well results in application to the opening of the column or capillary. In some embodiments, such a loading well can include additional features to facilitate such loading, for example an additional recess immediately proximal to the opening of the capillary or column that is dimensioned to receive a small volume of sample, leaving the remaining (relatively large) volume of the loading well to act as a reservoir for solvent or buffer.

In another embodiment of the inventive concept chromatographic separation within the palette is performed using an open bed of chromatographic stationary phase media deposited within the palette, rather than being enclosed within a column or capillary. Absence of an enclosure that surrounds the stationary phase provides a number of benefits: (1) a detector can get closer to the source of signal, leading to improved signal intensity, (2) chromatography performed in such a manner is independent or at least less dependent on the solvent in which the sample is originally dissolved, as such a solvent can be removed by evaporation prior to application of the separating solvent, (3) such an arrangement permits post-separation manipulation of the chromatographic material, which can enhance visualization of the bands of separated material. For example, if the bands do not provide sufficient absorbance in the visible spectrum the entire bed of stationary phase can be treated with a reagent that makes the bands visible (similar to methods utilized with thin layer chromatography (TLC) plate). Such visualization is difficult to achieve when the separation media is enclosed. Similarly, in some embodiments such a bed of stationary phase chromatography media can be functionalized to provide or enhance visualization of separated materials. For example, chromatography media in such an embodiment can include a UV-active material which will lack fluorescence in areas where UV absorbing species are located. The latter embodiment is also possible with columns enclosed in transparent materials such as glass.

In some embodiments where chromatographic separation is used, the test method can include a step of derivatization of the analytical sample mixture with fluorescent molecules (e.g. tags) prior to chromatographic separation. Such a tag reagent can be selected to react with the desired product (and, in some embodiments, one or more impurities) allowing quantification of corresponding bands during and/or after their separation along the stationary phase, for example by characterizing emission upon excitation with UV light.

The inventors have found that a characteristic of Cherenkov radiation measurements is that, while the excess of energy is dissipated in the form of broad spectrum (i.e. UV to visible) light, the amount of light detected by the plate reader is dependent upon the media wherein initiating radioactive disintegration occurs. This interaction with the media is in turn highly dependent on temperature. At stable temperatures readings are not expected to change. However, in case of performing [F-18]FDG quality control tests, there are methods that require incubation at non-ambient temperatures (for example, a pyrogen test can require a 37° C. incubation). The inventors have determined that while a palette is equilibrating to such an elevated temperature, Cherenkov measurements are likely to be unstable and can not produce results suitable for calculation of half-life and radioactivity concentration. In order to enable both tests to be performed concurrently in the same palette, some embodiments of the inventive concept utilize a palette design wherein the compartment designated for radiation measurements is thermally isolated from the remainder of the palette. The palette essentially acts as a heat sink and reaches thermal equilibration slowly.

In such a palette an isolated compartment with thin walls, minimal sample volume and minimal connections to the rest of the device comes to temperature and equilibrates rapidly and can produce stable results much earlier than if such a test site were located within slowly equilibrating regions of the palette. In preferred embodiments temperature equilibration is achieved within such a thin-walled, isolated compartment is under 5 minutes while the equilibration times with wells that have the entire palette a heat sink can take up to an hour to equilibrate. In other embodiments temperature equilibration of such a thin walled compartment occurs in less than 10 minutes, less than 15 minutes, less than 20 minutes, less than 25 minutes, or less than 30 minutes. In other embodiments of the inventive concept the thermally isolated region of the test palette can reach thermal equilibrium with its surroundings in less than 50%, 40%, 30%, 20%, 10%, and/or 5% of the time required for the remainder of the test palette to do so.

In some embodiments such a thermally isolated region can be provided by a thin walled, isolated well or compartment that is placed on a corner or outer edge of the palette. Alternatively, such a thermally isolated region can be joined to the remainder of the palette by one or more thin connections, which provide little to no heat transfer between the thermally isolated region and the remainder of the test palette. In some embodiments such a thin walled, thermally isolated compartment is sealed on all sides. In still other embodiments such a thin walled, thermally isolated compartment is completely filled with liquid and sealed in such a way that it is having no liquid-air interface (in the path of optical measurement). In still other embodiments such a thin walled, thermally isolated compartment is substantially flat having a depth which is substantially smaller than the width.

Similarly, in some embodiments the layout of the positions within a palette is optimized to reduce or eliminate cross-talk between measurements. In preferred embodiments there are 3 groups of features that are spatially separated for optimal performance: a separator (for example a microcolumn, capillary, or plate), a fast thermally equilibrating compartment for measurements requiring thermal stability, and a group of compartments that are designed for non-radioactive measurements (such as pH or pyrogens) that are performed on a radioactive sample. Such separation of features uniquely enables most accurate measurements of all radiation-related parameters. It should also be appreciated that the use of Cherenkov radiation for determination of radioactivity greatly reduces the spatial separation required for reduction of crosstalk between test sites.

In addition to spatial separation, further functional separation can be provided by including shielding materials (such as tungsten or lead) within the palette to isolate radioactive signals originating from different locations within the test fixture. In one embodiment such shielding is accomplished by the use of a wax, plastic, resin, or similar material that incorporates lead or tungsten powder. In another embodiment shielding can be positioned around the detector in such a way that it can only detect signals from the compartment that it is currently monitoring.

Test palettes of the inventive concept can be made of any material with suitable optical properties and chemical resistance. Suitable materials include polystyrene, polycarbonate, polypropylene, polyethylene, glass, and quartz. In some embodiments a palette can include more than one material, for example incorporating specific test regions constructed from materials with different chemical or optical properties from the rest of the palette. For example a palette can include a preparative or test region with improved chemical resistance. In another example, a palette can include a testing region that includes a "window" or similar inclusion of an optical material that has improved transmission of an optical wavelength that is not well transmitted by surrounding material of the palette. In a preferred embodiment, the configuration and external dimensions of a palette of the inventive concept correspond to those of a conventional 96-well microplate, and permit the palette to be used with a microplate reader. It should be appreciated that such a configuration advantageously supports automated pipetting. In combination with the use of a movable tray (such as a tray manipulation mechanism incorporated into a plate reader, a method can be implemented in which no direct user interaction is required to perform the analytical reactions and read the results. In some embodiments automated pipetting can be performed on a palette while the latter is located on the tray of a plate reader. Such arrangement allows analysis of the palette to start automatically after the pipetting has been finished without the need for the user (or robotic mechanism) to move the palette from pipetting location to the analysis location.

Kits of the inventive concept can include one or more palette(s). In some embodiments of the inventive concept, reagents and features necessary to perform the analytical reactions are incorporated into the same palette. In other embodiments, reagents are provided in one or more containers, cartridges, plate(s), or palette(s) that are distinct and separate from a palette(s) in which the analytical reactions are performed. In a preferred embodiment (i.e. for practical application) reagents are packaged in individually sealed vials first and the filled vials are assembled into a rack. This allows each vial to be filled under conditions that are optimal for that particular reagent rather than under a set of conditions that are potentially less than optimal for at least some of the reagents. This advantageously simplifies manufacture of reagent vials (e.g. pH reagents) that do not have stringent requirements (such as sterility), while more complex manufacturing methods can be reserved for those reagents that require them. Assembly of sealed vials into racks can take place in non-sterile conditions, which also simplifies production. Finally, different reagents can be packaged at different facilities, advantageously supporting decentralized manufacturing.

In one embodiment a kit can include a rack of sealed vials and an empty palette. In such an embodiment reagents are transferred to the empty palette by the user immediately before use, followed by dispensing of sample. In another embodiment a single palette contains individually sealed vials/containers with reagents and empty wells/compartments for analyses. In yet another embodiment a palette has, in addition to these two potential arrangements, a chromatography column or capillary within the same palette.

Another embodiment of the inventive concept is a method for characterizing acetonitrile content of a sample. Acetonitrile is a solvent widely used in production of radiopharmaceuticals. It is a class 2 toxic solvent and manufacturers are mandated to test final product for residual amount of acetonitrile. Due to its toxicity, typical QC limit for this compound is very low. Concentration of acetonitrile in the final dose should not exceed 400 ppm. The current compendial method for this test is Gas Chromatography (GC). While highly sensitive and specific, this method requires the use of a complex instrument and highly trained personnel. GC machines require a supply of high purity gases, for which the associated infrastructure includes storage, purchasing and daily monitoring of high pressure gas cylinders.

In one embodiment of the inventive concept metal complexes (such as ruthenium, cobalt or other metal complexes) are provided that exhibit a change in optical behavior on exposure to acetonitrile. Depending upon the metal complex selected, measurable fluorescence and/or a measurable spectral shift between the species bound with acetonitrile and free complex can be observed.

In another embodiment of the inventive concept, acetonitrile is reacted with a reactive amine (for example hydroxylamine, ammonia, ethanolamine, hydrazine, hydrazone, and/or hydroxylamine), a thiol, or another reagent to generate a chromophore, lumiphore, or a fluorophore (either as a product of the reaction itself or as a result of complexation of reaction products with another species such as a metal) to produce a change in optical density/absorbance, luminescence, or fluorescence. Suitable metals include Aluminium, Barium, Beryllium, Bismuth, Cadmium, Calcium, Cerium, Cesium, Chromium, Cobalt, Copper, Dysprosium, Erbium, Europium, Gadolinium, Gallium, Gold, Hafnium, Holmium, Iridium, Iridium, Iron, Lanthanum, Lead, Lithium, Lutetium, Magnesium, Manganese, Mercury, Molybdenum, Neodymium, Nickel, Niobium, Osmium, Palladium, Platinum, Potassium, Praseodymium, Rhenium, Rhodium, Rubidium, Ruthenium, Samarium, Scandium, Silver, Sodium, Strontium, Tantalum, Technetium, Terbium, Thallium, Thulium, Tin, Titanium, Tungsten, Uranium, Vanadium, Ytterbium, Yttrium, Zinc, and Zirconium in any oxidation state.

As noted above, another aspect of radiopharmaceutical testing is determination of sterility. In some embodiments, such a test can be performed by providing a tube or vial containing a bacterial growth media, which is in turn incubated following the addition of a sample and assessed after being placed (for example, horizontally) within a palette. In an alternative embodiment for such sterility testing, a palette is provided having two or more compartment(s) for sterility testing. One such a compartment can be an incubation compartment, which has an observation window. Such a palette can also include a gas collection compartment that joined to the incubation compartment by displaced both horizontally and vertically from it. The volumes of these compartments can be such that the volume of growth media provided together with sample fills the entire volume of the incubation compart and a portion of the gas collection compartment, such that the liquid-gas interface does not contact the observation window and interfere with measurements. This design enables testing for aerobic bacteria which require air (oxygen) for their growth, but removes such air from the optical path during the assessment. The incubation compartment can be scanned within a plate reader for detecting bacterial growth while the gas collection compartment contains enough air to sustain such growth (if it does occur) without interfering with measurement.

Another embodiment of the inventive concept is a direct measurement method that permits characterization of Kryptofix® within the sample. Uncomplexed Kryptofix™ exhibits negligible light absorption, making it difficult to quantify its concentration with optical methods. Upon complexation with heavy metal ions (such as lead or mercury), however, a strong charge-transfer absorption band appears in the ultraviolet region of the spectrum (approx. 260 nm). This absorption permits direct quantification of Kryptofix™ by formation of a heavy metal ion complex followed by characterization of UV absorption (for example, using a plate reader). In typical characterizations using such a method Kryptofix™ could be accurately quantified at concentrations down to $10^{-5}$ mol/L. Surprisingly, this direct method is relatively insensitive to interference from other species competing for the metal ion.

It should be appreciated that the relatively short wavelength of the absorption band requires using special UV-transparent plastics for the consumable palette. The inventors contemplate that complexation with other metals, known for stable charge-transfer complexes, such as Ru, Pd or Pt should present absorption bands at longer wavelength, potentially compatible with conventional plastics. Alternatively, a hybrid plastic consumable can be provided that incorporates a small piece of UV transparent material (for example, as a window) within a palette made of different material for observation at UV wavelengths.

At least the following embodiments of a method have been described:

A method of sterility testing based on labeling live cells with reagents that allow quantification of the number of cells by optical detection in a palette. A device where optical signal from labeled live cells can be detected and translated into the number of live cells in the sample; a device for sterility assessment comprising a channel where the channel has one or more electrodes; the channel is connected to a reservoir; the channel is connected to two or more reservoirs; the cross-section of the channel is comparable to the size of a living cell; the electrodes perform a measurement; the signal is different in presence and in absence of live cells in proximity to electrode(s); the signal can be used to count live cells; more than one channel can be included; all channels run in parallel; all channels have the same originating container; all channels have the same final container; a palette containing any combination of the following reagents: pH indicator, Kryptofix™ indicator, scintillating liquid, and LAL reagents; a palette containing both solids and liquids; a palette containing solids in the 0.1 mg range; a palette containing solids and solvents that from mixtures that are unstable for prolonged periods of time (such as LAL reagents); a method of using a palette for the assessment of a gamma spectrum (MCA); a method of using palettes for QC or radiopharmaceuticals; the palette is a standard microwell plate; the palette sealed with reagents; the palette can contain HPLC references and standards either in solid or liquid form; a method of performing self-calibration of HPLC using only the contents of one palette; a method for radiation detection using a spectrophotometer; a method for radiation detection using a plate reader; a device for radiation detection comprising a palette and a plate reader; the device including a sub-system capable of chemical synthesis; the device enabling radiosynthesis or a radiopharmaceutical; the device including a sub-system capable of dispensing product; the product can be dispensed as single patient doses; a device and method for optical detection of any of the following or any combination thereof: color, clarity, pH, Kryptofix™ concentration, endotoxin concentration, radioactivity concentration, radionuclidic identity, radiochemical identity, radiochemical purity, concentrations of organic solvents, sterility.

A method of using palettes where solute includes a radionuclide; a device and method for Optical detection using a palette; a device and method where LC injection is performed form a palette; the palette can be placed in an optical path between the source of an optical signal and detector; the device and method can include and utilizing a plate reader; a method of assessing all QC parameters of a radiopharmaceutical using a palette but without flowing any liquids from one location on the palette to another at any time; a method of assessing all QC parameters of a radiopharmaceutical using a palette allowing flow of liquids from one location on the palette to another; a method of QC assessment relying on measurement of an optical property; a method of QC assessment relying on measurement of a change in optical property; a method of QC assessment relying on measurement of a rate of change in optical property; a method and device for full assessment of QC or radiopharmaceuticals without running any liquids through any channels; a method and device for full assessment of QC or radiopharmaceuticals without running any liquids through any valves; a method and device for full assessment of QC or radiopharmaceuticals required for administering product to a human patient; a method and device for partial assessment of QC or radiopharmaceuticals without running any liquids through any channels; a method and device for partial assessment of QC or radiopharmaceuticals without running any liquids through any valves; a device and method for QC assessment of radiopharmaceutical having no injection port; a device and method for QC assessment of radiopharmaceutical having no network of channels and/or valves; a device and method for QC assessment of radiopharmaceutical having internal or external radiation shielding; a device and method for QC assessment of radiopharmaceutical where all results are quantitative; a device and method for QC assessment of radiopharmaceutical where all results are quantitative and compiled in a single report produced automatically; a method of measuring exact turbidity of a sample using continuous spectrum absorption measurement; a method for determining whether the sample is of acceptable turbidity by comparing the measurement against a preset threshold; a device and method where all materials necessary for full QC assessment are packaged on a palette; the device and method can include HPLC solvents; a device/method with a combination of transition metal and transition metal-sensitive indicator for detection/quantification of Kryptofix™ in a sample; the device can have two or more reagents mixed with each other (Pre-packaged palette contains these reagents as a mixture prior to use); a palette containing only solids (solvents can be stored as stock within the instrument or come separately); a method relying on two palettes where one has all the reagents and the other is used for detection; a method where the reagents are pre-packaged on a palette in excess, but are metered by the caddy in specific amounts for use in the tests; a method of performing QC of a radiopharmaceutical having a "cold phase" (prior to injection of radioactive analyte) and a "hot phase" after the injection of the latter (with optimization concentrating on minimizing the latter phase and moving as many manipulations as possible from hot phase to cold); a method and device for Assessment of radioactive signals arising from different wells within a palette without shielding those wells from one another; a method where the distinction between colored sample and a turbid sample is made based on the fitting of the absorption spectrum with a mathematical equation; such equation can be an exponential function; the fitting with $chi^2$ above certain threshold deemed a signal for the sample being colorless; a device for organic solvent concentration assessment with HPLC; HPLC injection driven by a system of caddies and palettes without human interference; full report on all QC parameters generated automatically from 1 injection of analyte without user interaction with the instrument; chemical purity assessment without chromatography; chemical purity assessment by comparing an absorption spectrum to a reference absorption spectrum at multiple wavelengths; specific activity assessment without chromatography; sterility assessment by counting cells in a channel between two electrodes; sterility assessment device having two wells connected by multiple channels and electrodes measuring an electrical signal across each channel; a method of using the device described above to assess sterility or presence of live cells; devices for electrode or absorption-based sterility measurements that are either completely based on palettes and caddies or do not involve them at all.

The following are additional embodiments of the inventive concept:

A system for performing manipulations with radioactive materials, relying for the transfer of materials on the palettes and caddies; an integrated system that includes a part that relies on palettes and caddies and another part that utilizes other means for the material transfer; A system where the manipulations are used to asses quality control parameters of a radiopharmaceutical sample; a system where the chemical manipulations are used in the synthesis of radiolabeled molecules; a system where the transfer of materials is performed as a part of dispensing, that is preparation of existing material for shipping and use by an end-user; A system where the aforementioned chemical manipulations are used in any combination of synthesis, analysis and/or dispensing of radioactive materials; an aforementioned system designed to manipulate the amount of radioactive material not requiring special radiation shielding; An aforementioned designed to manipulate radioactivity in such a manner that 2 inch lead shielding or its equivalent is sufficient for safe operations; an aforementioned system that collects all liquid waste material within palettes and caddies; a system for manipulation of radioactive material where the material only comes in contact with the disposable surfaces, that is surfaces only used for one operation (with examples including but not limited to synthesis/analysis/transfer/mixing/extraction); a system where the same palette is shared between the processes performed in the system: synthesis, analysis, dispensing or any combination of thereof; A system where each process uses a designated palette; a system that can be portable, that is sufficiently small to be moved from one location to another and only rely on external power supply for its operation; a system which provides for temperature control for the entire palette of a portion thereof; an aforementioned integrated system that uses caddies to transfer material form the palette-caddy part of the system to the parts of the system operating based on different principles, such as chromatographic equipment.

A palette, that is a disposable component used in the radiochemical synthesis, analysis or dispensing, includes plurality of containers not interconnected with each other used in synthesis, analysis or dispensing of radioactive materials; palettes made out of single piece of homogeneous material. Palettes can be made out of multiple pieces of material and linked to each other, inserted in each other or otherwise mechanically connected. Such combinations can include combinations of disposable and re-usable components. Other embodiments include palettes where containers can be moved within a palette and a palette that incorporates radiation shielding.

Other embodiments include a caddy that is a disposable component used as a temporary container to transfer material between containers of a palette or from a palette outside of the system; caddies designed to deliver material (final product, analyte sample or other) to the end user and used directly, without further transfer of material enclosed; caddies designed to be docked to hardware other than the palette; a caddy that incorporates radioactive shielding; palettes and caddies that contains silica, modified silica, ion exchange resin or any other sorbent in one or more containers;

A radiochemistry system designed to perform periodic sampling of the reaction mixture and analysis of the samples (obtained at different time-points throughout the synthesis process and not limited to sampling the end-product) within the same system. A system of that is designed to automatically receive the palettes from a storage location and automatically eject used palettes and caddies into a receptacle (potentially a shielded one in some embodiments), thus permitting continuous operation with no human interference. A system that performs quality control of a radiopharmaceutical along a plurality of parameters, including, but not limited to clarity, pH, a phase transfer reagent concentration, pyrogenicity, radio-isotope half-life and radioactivity concentration. The aforementioned system that measures several parameters in one test and reports several parameters to meet specifications if the test results are satisfactory.

The methods relying on the aforementioned systems and components are also embodiments of the invention. Such methods include an automated method for separation and/or purification of radiopharmaceuticals relying on liquid-liquid extraction performed by means of palettes and caddies and a method for performing quality control of radiopharmaceuticals that relies on use of palettes and caddies;

In one embodiment, the system is configured to synthesize, analyze or dispense chemicals used in diagnostic imaging, such as PET; These chemicals comprise at least one radionuclide, which can be selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$. Other embodiments include a system for performing manipulations with radioactive materials, relying for the transfer of materials on the palettes and caddies; an integrated system that consists of a part that relies on palettes and caddies and another part that utilizes other means for the material transfer; systems where the transformations are used to assess quality control parameters; systems where the chemical transformations are used in the synthesis of radiolabeled molecules; systems where the transfer of materials is performed in order to prepare an existing material for shipping and use by an end-user; a system including a combination of the afore mentioned systems or a subset of thereof; a system for performing of manipulation of radioactive material where the material only comes in contact with the disposable surfaces, that is surfaces only used for one operation, including but not limited to synthesis/analysis/transfer; a system where the manipulations are directed toward synthesis, analysis, dispensing of radiopharmaceuticals or combination of these processes or subset of these processes; and a system where the same palette is shared between the processes performed in the system: synthesis, analysis, dispensing or any combination of thereof; a system where each process uses a designated palette.

Disposable components, such as palettes, can include of plurality of containers that are not interconnected with other palettes used in synthesis, analysis or dispensing of radioactive materials; palettes made out of single piece of homogeneous material; palettes made out of multiple pieces of material and linked to each other, inserted in each other or otherwise mechanically connected; and palettes where containers can be moved within a palette A disposable component can be used as a temporary container to transfer material between containers of the palette. A disposable component used as a temporary container to transfer material outside of the system. A disposable component can be designed to be used by the end user. A disposable component can include a caddy with a radiopharmaceutical ready for injection. A disposable component can be designed to be docked to hardware other than the palette.

Other embodiments include a system designed to manipulate the amount of radioactive material not requiring special radiation shielding; a system designed to manipulate radioactivity in such a manner that 2 inch lead shielding or its equivalent is sufficient for safe operations; a palette that incorporates radiation shielding; a caddy that incorporates radioactive shielding; a system that collects all liquid waste material within pallets and caddies; a system that can be portable, that is sufficiently small to be moved from one location to another and only rely on external power supply for its operation; a system which provides for temperature control for the entire palette of a portion of thereof; a system that uses caddies to transfer material form the palette-caddy part of the system to the parts of the system operating based on different principles, such as chromatographic equipment; a disposable component that contains silica, modified silica, ion exchange resin or any other sorbent in one or more containers; a disposable components that contain silica, modified silica, ion exchange resin or any other sorbent; an automated method for separation and/or purification of radiopharmaceuticals relying on liquid-liquid extraction performed by means of palettes and caddies; a radiochemistry system designed to perform periodic sampling of the reaction mixture and analysis of the samples within the same system; a system that is designed to automatically receive the palettes from a storage location (inside or outside the system) and automatically eject used palettes an caddies into a receptacle, thus permitting continuous operation with no human interference; a system that performs quality control of a radiopharmaceutical along a plurality of parameters, including, but not limited to clarity, pH, a phase transfer reagent concentration, pyrogenicity, radio-isotope half-life and radioactivity concentration; a system that measures several parameters in one test; a system that reports several parameters to meet the specifications if the result of this one test is acceptable; a system that relies on a palette with solid support or absorbent embedded in one or more containers of a caddy; a machine that allows complete assessment of the quality of a radiopharmaceutical without any part of the analysis relying on human senses; a device that generates a report that can be reviewed remotely; a device that allows quality assessment of a sample without the reviewer of results being co-located with the sample; a system where the reviewer of the report can review such reports from multiple production facilities and release products at multiple locations for human administration; and a business model where a pharmacy offers its services to multiple radiopharmaceutical production facilities, where such pharmacy can or can not be affiliated with an individual production site.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps can be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for determining a concentration of a synthesis component in a radiopharmaceutical sample, comprising:
   providing a metal complex as a liquid solution;
   contacting the radiopharmaceutical sample in the form of a liquid solution with the metal complex for a period of time sufficient to form a modified metal complex;
   measuring an optical characteristic of the modified metal complex; and
   determining a concentration of the synthesis component in the radiopharmaceutical sample based on the measured optical characteristic via mathematical calculations.

2. The method of claim 1, wherein the measured optical characteristic is selected from the group consisting of fluorescence, absorbance, optical density, scatter, turbidity, refractive index, optical polarization, phosphorescence and luminescence.

3. The method of claim 1, wherein the synthesis component in the radiopharmaceutical sample is an acetonitrile.

4. The method of claim 1, wherein the metal complex comprises a metal selected from the group consisting of Aluminum, Barium, Beryllium, Bismuth, Cadmium, Calcium, Cerium, Cesium, Chromium, Cobalt, Copper, Dysprosium, Erbium, Europium, Gadolinium, Gallium, Gold, Hafnium, Holmium, Indium, Iridium, Iron, Lanthanum, Lead, Lithium, Lutetium, Magnesium, Manganese, Mercury, Molybdenum, Neodymium, Nickel, Niobium, Osmium, Palladium, Platinum, Potassium, Praseodymium, Rhenium, Rhodium, Rubidium, Ruthenium, Samarium, Scandium, Silver, Sodium, Strontium, Tantalum, Technetium, Terbium, Thallium, Thulium, Tin, Titanium, Tungsten, Uranium, Vanadium, Ytterbium, Yttrium, Zinc, and Zirconium.

5. The method of claim 1, wherein an acetonitrile in the radiopharmaceutical sample interacts with the metal complex, wherein measuring an optical characteristic of the modified metal complex includes measuring a change in the absorbance spectrum between a first optical behavior of the metal complex and a second optical behavior of the modified metal complex that interacts with the acetonitrile in the radiopharmaceutical sample.

6. The method of claim 5, further including determining a ratio of acetonitrile-bound and acetonitrile-unbound metal complexes based on changes in the absorbance spectrum and determining the concentration of the acetonitrile in the radiopharmaceutical sample based on the ratio.

7. The method of claim 1, wherein the synthesis component includes a phase transfer reagent.

8. The method of claim 7, wherein the phase transfer reagent is 4, 7, 13, 16, 21, 24-hexaoxa-1, 10-diazabicyclo-(8.8.8) hexacosane and wherein the measured optical characteristic includes light absorbance or optical density.

9. The method of claim 8, further comprising interacting the 4, 7, 13, 16, 21, 24-hexaoxa-1, 10-diazabicyclo-(8.8.8) hexacosane with the metal complex.

10. The method of claim 9, further including providing an indicator for the metal complex, the method further comprising interacting the indicator, the metal complex and the 4, 7, 13, 16, 21, 24-hexaoxa-1, 10-diazabicyclo-(8.8.8) hexacosane, wherein the 4, 7, 13, 16, 21, 24-hexaoxa-1, 10-diazabicyclo-(8.8.8) hexacosane competes with the indicator for the metal complex, wherein a concentration of the indicator interacting with the metal complex decreases in the presence of 4, 7, 13, 16, 21, 24-hexaoxa-1, 10-diazabicyclo-(8.8.8) hexacosane and the measured optical characteristic includes a change in a measured absorbance spectrum, wherein determining the concentration of 4, 7, 13, 16, 21, 24-hexaoxa-1, 10-diazabicyclo-(8.8.8) hexacosane in the radiopharmaceutical sample is based on the changes in the measured absorbance spectrum.

11. The method of claim 1, further comprising mixing a specific amount of the metal complex and a metal indicator with the radiopharmaceutical sample in a well and measuring an absorbance or optical density with a spectrophotometer with light passing through the well such that an intensity of absorbance is measured, the method further comprising correlating the intensity of measured absorbance with a concentration of 4, 7, 13, 16, 21, 24-hexaoxa-1, 10-diazabicyclo-(8.8.8) hexacosane present in the radiopharmaceutical sample.

12. The method of claim 7, wherein the phase transfer reagent is a quaternary ammonium salt and wherein the measured optical characteristic includes light absorbance or optical density.

13. A method for determining a concentration of a synthesis component in a radiopharmaceutical sample, comprising:
providing an indicator as a liquid solution;
contacting the radiopharmaceutical sample in the form of a liquid solution sample with the indicator for a period of time sufficient for interaction of the synthesis component with the indicator;
measuring an optical characteristic of the indicator and synthesis component after their interaction; and
determining a concentration of the synthesis component in the radiopharmaceutical sample based on the measured optical characteristic.

14. The method of claim 13, wherein the synthesis component includes a phase transfer reagent.

15. The method of claim 7, further comprising conducting a 2-phase liquid-liquid extraction.

16. The method of claim 15, further comprising determining optical characteristics of at least one of the two phases that change as a result of phase transfer reagent interaction with the metal complex.

17. The method of claim 15, wherein any layer of the 2-phase liquid-liquid extraction is accessible at any time.

18. The method of claim 15, further comprising transferring one of the two phases from one location to another.

19. The method of claim 15, wherein a separation of sample components is performed on a palette.

* * * * *